US008288147B2

(12) United States Patent
Keasling et al.

(10) Patent No.: US 8,288,147 B2
(45) Date of Patent: *Oct. 16, 2012

(54) HOST CELLS FOR PRODUCTION OF ISOPRENOID COMPOUNDS

(75) Inventors: Jay D. Keasling, Berkeley, CA (US); Vincent J.J. Martin, Montreal (CA); Douglas J. Pitera, Oakland, CA (US); Seon-Won Kim, Sacheon (KR); Sydnor T. Withers, III, Richmond, CA (US); Yasuo Yoshikuni, Berkeley, CA (US); Jack Newman, San Francisco, CA (US); Artem Valentinovich Khlebnikov, Mountain View, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/027,517

(22) Filed: Feb. 15, 2011

(65) Prior Publication Data
US 2011/0229958 A1 Sep. 22, 2011

Related U.S. Application Data

(60) Continuation of application No. 12/576,068, filed on Oct. 8, 2009, now Pat. No. 7,915,026, which is a continuation of application No. 11/610,686, filed on Dec. 14, 2006, now Pat. No. 7,736,882, which is a division of application No. 10/006,909, filed on Dec. 6, 2001, now Pat. No. 7,172,886.

(51) Int. Cl.
C12P 1/00 (2006.01)
C12P 7/00 (2006.01)
C12N 9/00 (2006.01)
C12N 9/02 (2006.01)
C12N 9/12 (2006.01)
C12N 9/88 (2006.01)
C12N 1/20 (2006.01)
C12N 15/00 (2006.01)
C07H 21/04 (2006.01)

(52) U.S. Cl. ........ 435/252.3; 435/41; 435/132; 435/183; 435/189; 435/194; 435/232; 435/320.1; 536/23.2

(58) Field of Classification Search .................. None
See application file for complete search history.

(56) References Cited

U.S. PATENT DOCUMENTS

| 6,072,045 | A | 6/2000 | Chappell et al. |
| 6,114,160 | A | 9/2000 | Croteau et al. |
| 6,190,895 | B1 | 2/2001 | Croteau et al. |
| 6,281,017 | B1 | 8/2001 | Croteau et al. |
| 6,284,506 | B1 | 9/2001 | Hoshino et al. |
| 6,291,745 | B1 | 9/2001 | Meyer et al. |
| 6,306,633 | B1 | 10/2001 | Wilding et al. |
| 6,495,354 | B2 | 12/2002 | Chappell et al. |
| 6,531,303 | B1 | 3/2003 | Mills et al. |
| 6,916,972 | B2 | 7/2005 | Falco et al. |
| 6,989,257 | B2 | 1/2006 | Berry et al. |
| 7,129,392 | B2 | 10/2006 | Hahn et al. |
| 7,132,268 | B2 | 11/2006 | Miyake et al. |
| 7,736,882 | B2* | 6/2010 | Keasling et al. ........... 435/252.3 |
| 7,915,026 | B2* | 3/2011 | Keasling et al. ........... 435/252.3 |
| 2004/0029239 | A1 | 2/2004 | Ohto et al. |
| 2004/0063182 | A1 | 4/2004 | Ohto et al. |
| 2005/0241017 | A1 | 10/2005 | Hahn et al. |
| 2005/0266518 | A1 | 12/2005 | Berry et al. |
| 2007/0077616 | A1 | 4/2007 | Keasling et al. |

FOREIGN PATENT DOCUMENTS

| EP | 0955363 | 11/1999 |
| EP | 1360300 | 11/2003 |
| EP | 1392824 | 3/2004 |
| WO | WO 0210398 | 2/2002 |
| WO | WO 02099095 | 12/2002 |
| WO | WO 0001650 | 1/2005 |

OTHER PUBLICATIONS

Altincicek et al., "GcpE is Involved in the 2-C-Methyl-D-Erythritol 4-Phosphate Pathway of Isoprenoid Biosynthesis in *Escherichia coli*" (2001) Journal of Bacteriology, vol. 183, No. 8, pp. 2411-2416.
Amann et al., Tightly Regulated Tac Promoter Vectors Useful for the Expression of Unfused and Fused Proteins in *Escherichia coli*, (1988), Gene, vol. 69, pp. 301-315.
Balbas et al., (1996), A pBRINT family of plasmids for integration of cloned DNA into the *Escherichia coli* chromosome. Gene, vol. 172, No. 1, pp. 65-69.
Barkovich et al., "Metabolic Engineering of Isoprenoids" (2001), Metabolic Engineering, vol. 3, No. 1, pp. 27-39.
Campos et al., Identification of gcpE as a Novel Gene of the 2-C-Methyl-D-Erythritol 4-Phosphate Pathway for Isoprenoid Biosynthesis in *Escherichia coli*, (2001), FEBS Letters, vol. 488, pp. 170-173.
Campos et al., *Escherichia coli* Engineered to Synthesize Isopentenyl Diphosphate and Dimethylallyl Diphosphate from Mevalonate: A Novel System for the Genetic Analysis of the 2-C-Methyl-D-Erythritol 4-Phosphate Pathway for Isoprenoid Biosynthesis (2001) Biochemistry Journal, vol. 353, pp. 59-67.
Cunningham et al., "Molecular Structure and Enzymatic function of Lycopene Cyclase from the *Cyanobacterium synechococcus* sp Strain PCC7942, " (1994) The Plant Cell, vol. 6, pp. 1107-1121.

(Continued)

Primary Examiner — Christian Fronda
(74) Attorney, Agent, or Firm — Paula A. Borden; Bozicevic, Field & Francis LLP.

(57) ABSTRACT

Methods for synthesizing isopentenyl pyrophosphate are provided. A first method comprises introducing into a host microorganism a plurality of heterologous nucleic acid sequences, each coding for a different enzyme in the mevalonate pathway for producing isopentenyl pyrophosphate. A related method comprises introducing into a host microorganism an intermediate in the mevalonate pathway and at least one heterologous nucleic acid sequence, each sequence coding for an enzyme in the mevalonate pathway necessary for converting the intermediate into isopentenyl pyrophosphate. The invention also provides nucleic acid sequences, enzymes, expression vectors, and transformed host cells for carrying out the methods.

32 Claims, 5 Drawing Sheets

OTHER PUBLICATIONS

Dairi et al., Eubacterial Diterpene Cyclase Genes Essential for Production of the Isoprenoid Antibotic Terpentecin (2001), Journal of Bacteriology, vol. 183, No. 20, pp. 6085-6094.

Guzman et al, Tight Regulation, Modulation, and High-Level Expression by Vectors Containing the Arabinose $P_{BAD}$ Promoter, (1995), Journal of Bacteriology, vol. 177, No. 14, pp. 4121-4130.

Hahn et al., "*Escherichia coli* Open Reading Frame 696 Is idi, a Nonessential Gene Encoding Isopentenyl Diphosphate Isomerase," (1999), Journal of Bacteriology, vol. 181, No. 15, pp. 4499-4504.

Hahn et al, "I-Deoxy-D-Xylulose 5-Phosphate Syntheses, the Gene Product of Open Reading Frame (ORF) 2816 and ORF 2895 in *Rhodobacter capsulatus*" (2001), Journal of Bacteriology, vol. 183, No. 1, pp. 1-11.

Hamano et al., Cloning of a Gene Cluster encoding Enzymes Responsible for the Mevalonate Pathway from a Terpenoid-Antibioltic-Producing *Streptomyces* Strain, (2001), Biosci Biotechnol. Biochem. vol. 65, No. 7, pp. 1627-1635.

Kaneda et al., "An Unusual Isopentenyl Diphosphase Isomerase Found in the Mevalonate Pathway Gene Cluster from *Streptomyces* sp. Strain CL190" (2001), PNAS, vol. 98, No. 3, pp. 932-937.

Kim et al., "Metabolic Engineering of the Nonmevalonate Isopentenyl diphosphate Synthesis Pathway in *Escherichia coli* Enhances Lycopene Production" (2001), Biotechnology and Bioengineering, vol. 72, No. 4, pp. 408-415.

Kovach et al., "pBBRIMCS: A Broad-Host-Range Cloning Vector" (1994), BioTechniques, vol. 16, No. 5, pp. 800-802.

Kovach et al., Four New Derivatives of the Broad-Host-Range-Cloning Vector pBBRIMCS. Carrying Different Antibiotic-Resistance Cassettes, (1995), Gene, vol. 166, pp. 175-176.

Mahmoud et al., "Metabolic Engineering of Essential Oil Yield and Composition in Mint by Altering Expression of Deoxyxylulose Phosphate Reductoisomerase and Methofuran Synthase", (2001), PNAS, vol. 98, No. 15, pp. 8915-8920.

McAteer et al., "The lytb Gene of *Escherichia coli* Is Essential and Specifies a Product Needed for Isoprenoid Biosyntheis" (2001), Journal of Bacteriology, vol. 183, No. 24, pp. 7403-7407.

Oulmouden et al., "Nucleotide Sequence of the ERG12 Gene of *Saccharomyces cerevisae* Encoding Mevalonate Kinase" (1991), Current Genetics, vol. 19, pp. 9-14.

Polakowski et al., "Overexpression of a Cytosolic Hydroxymethylglutaryl-CoA Reductase Leads to Squalene Accumulation in Yeast", (1998), Appl. Microbiol. Biotechnol., vol. 49, pp. 66-71.

Rohdich et al., Studies on the Nonmevalonate Terpene Biosynthetic Pathway: Metabolic Role of IspH (LyB) Protein, (2002), PNAS, vol. 99, No. 3, pp. 1158-1163.

Rohlin et al., "Microbioal Pathway Engineering for Industrial Processes: Evolution, Combinatorial Biosynthesis and Rational Design" (2001), Current Opinion in Microbiology, vol. 4, pp. 330-335.

Rohmer et al., "Isoprenoid Biosynthesis in Bacteria: A Novel Pathway for the Early Steps Leading to Isopentenyl Diphosphate", (1993), Biochem. J., vol. 295, pp. 517-524.

Sandmann, "Carotenoid Biosynthesis and Biotechnological Application" (2001), Archives of Biochemistry and Biophysics, vol. 385, pp. 4-12.

Szkopinska et al., "The Regulation of Activity of Main Mevalonic Adic Pathway Enzymes: Farnesyl Diphosphas Synthase. 3-Hydroxy-3-Methylglutaryl-CoA Reductase, and Squalene Synthase in Yeast *Saccharomyces cerevidiae*", (2000), Biochemical and Biophysical Research Communications, vol. 267, pp. 473-477.

Takagi et al., "A Gene Cluster for the Mevalonate Pathway from *Streptomyces* sp. Strain CL190." (2000), Journal of Bacteriology, vol. 182, No. 15, pp. 4153-4157.

Tatiana et al., FEMS Microbiol Lett (1999), May 15, vol. 174, No. 2, pp. 247-250.

Toth et al., "Molecular Cloning and Expression of the cDNAs Encoding Human and Yeast Mevalonate Pyrophosphate Decarboxylase", (1996), The Journal of Biological Chemistry, vol. 271, No. 14, pp. 7895-7898.

Tsay et al., "Cloning and Characterization of ERG8, an Essential Gene of *Saccharomyces cervisiae* that Encodes Phosphomevalonate Kinase", (1991), Molecular and Cellular Biology, vol. 11, No. 2, pp. 620-631.

Wang et al., "Engineered Isoprenoid Pathway Enhances Astaxanthin Production in *Escherichia coli*", (1999), Biotechnology and Bioengineering, vol. 62, No. 2, pp. 235-241.

Wang et al., Directed Evolution of Metabolically Engineered *Escherichia coli* for Carotenoid Production, (2000), Biotechnol. Prod., vol. 16, No. 6, pp. 922-926.

66 FR 1099, Friday, Jan. 5, 2001.

BLAST 2 Sequences results. Sequence 1 gi 5531936, Sequence 2 gi 546900, printed on Jun. 24, 2005.

Hiser et al., "ERG10 from *Saccharomyces cerevisiae* Encodes Acetoacetyl-CoA Thiolase" (1994), Journal of Biological Chemistry, vol. 269, No. 50, pp. 31383-31389.

Hiser et al., Accession L20428, Feb. 23, 1995.

National Science Foundation Award Abstract No. 9911463.

Fujisaki et al., Isoprenoid synthesis in *Escherichia coli*. Separation and partial purification of four enzymes involved in the synthesis. (1986) Journal Biochemistry, vol. 99, No. 5, pp. 1327-1337.

Wilding et al. Idenfication, evolution, and essentiality of the mevalonate pathway for isopentenyl diphosphate biosynthesis in gram-positive cocci. J. Bacteriol. Aug. 2000:182(15):4319-27.

Berges, et al. The *Saccharomyces cerevisiae* mevalonate diphosphate decarboxylase is essential for viability, and a single Leu-to-Pro mutation in a conserved sequence leads to thermosensitivity. J. Bacteriol. Aug. 1997;179(15)4664-70.

Kajiwara, Expression of an exogenous isopentenyl diphosphate isomerase gene enhances isoprenoid biosynthesis in *Escherichia coli*. et al. Biochem J., Jun. 1, 1997;324 (Pt. 2):421-6.

Arkin and Fletcher, Fast, cheap and somewhat in control. Genome Biology, 2006, vol. 7, p. 114-114.6.

Hinson, et al., Post-translational regulation of mevalonate kinase by intermediates of the cholesterol and nonsterol isoprene biosynthetic pathways. J Lipid Res. Nov. 1997;38(11):2216-23.

Hiser, et al. ERG10 from *Saccharomyces cerevisiae* encodes acetoacetyl-CoA thiolase. J Biol Chem. Dec. 16, 1994;269(50):31383-9.

Alex, et al. Expression of *Brassica juncea* 3-hydroxy-3-methylglutaryl CoA synthase is developmentally regulated and stress-responsive. Plant J. Jun. 2000:22(5):415-26.

Basson, et al. Structural and functional conservation between yeast and human 3-hydroxy-3-methylglutaryl coenzyme A reductases, the rate-limiting enzyme of sterol biosynthesis. Mol Cell Biol. Sep. 1988;8(9):3797-808.

Zhu, et al. Plant Cell Physiol. Cloning and functional expression of a novel geranylgeranyl pyrophosphate synthase gene from *Arabidopsis thaliana* in *Escherichia coli*. Mar. 1997;38(3):357-61.

\* cited by examiner

SEQUENCE LISTING

<160> NUMBER OF SEQ ID NOS: 13

<210> SEQ ID NO 1
<211> LENGTH: 1185
<212> TYPE: DNA
<213> ORGANISM: Artificial Sequence
<220> FEATURE:
<223> OTHER INFORMATION: Description of Artificial Sequence: Synthetic
      Acetoacetyl-CoA thiolase nucleotide sequence

<400> SEQUENCE: 1

```
atgaaaaatt gtgtcatcgt cagtgcggta cgtactgcta tcggtagttt taacggttca        60
ctcgcttcca ccagcgccat cgacctgggg gcgacagtaa ttaaagccgc cattgaacgt       120
gcaaaaatcg attcacaaca cgttgatgaa gtgattatgg gtaacgtgtt acaagccggg       180
ctggggcaaa atccggcgcg tcaggcactg ttaaaaagcg ggctggcaga acggtgtgc        240 ggattcacgg tcaataaagt atgtggttcg ggtcttaaaa gtgtggcgct tgccgcccag       300
gccattcagg caggtcaggc gcagagcatt gtggcggggg gtatggaaaa tatgagttta       360
gccccctact tactcgatgc aaaagcacgc tctggttatc gtcttggaga cggacaggtt       420
tatgacgtaa tcctgcgcga tggcctgatg tgcgccaccc atggttatca tatggggatt       480
accgccgaaa acgtggctaa agagtacgga attacccgtg aaatgcagga tgaactggcg       540
ctacattcac agcgtaaagc ggcagccgca attgagtccg gtgcttttac agccgaaatc       600
gtcccggtaa atgttgtcac tcgaaagaaa accttcgtct tcagtcaaga cgaattcccg       660
aaagcgaatt caacggctga gcgttaggt gcattgcgcc cggccttcga taaagcagga       720
acagtcaccg ctgggaacgc gtctggtatt aacgacggtg ctgccgctct ggtgattatg       780
gaagaatctg cggcgctggc agcaggcctt accccctgg ctcgcattaa aagttatgcc        840
agcggtggcg tgccccccgc attgatgggt atggggccag tacctgccac gcaaaaagcg       900
ttacaactgg cggggctgca actggcggat attgatctca ttgaggctaa tgaagcattt       960
gctgcacagt tccttgccgt tgggaaaaac ctgggctttg attctgagaa agtgaatgtc      1020
aacggcgggg ccatcgcgct cgggcatcct atcggtgcca gtggtgctcg tattctggtc      1080
acactattac atgccatgca ggcacgcgat aaaacgctgg ggctggcaac actgtgcatt      1140
ggcggcggtc agggaattgc gatggtgatt gaacggttga attaa                     1185
```

<210> SEQ ID NO 2
<211> LENGTH: 1476
<212> TYPE: DNA
<213> ORGANISM: Artificial Sequence
<220> FEATURE:
<223> OTHER INFORMATION: Description of Artificial Sequence: Synthetic
      HMG-CoA synthase nucleotide sequence

<400> SEQUENCE: 2

```
atgaaactct caactaaact ttgttggtgt ggtattaaag gaagacttag gccgcaaaag      60
caacaacaat tacacaatac aaacttgcaa atgactgaac taaaaaaaca aaagaccgct     120
gaacaaaaaa ccagacctca aaatgtcggt attaaaggta tccaaattta catcccaact     180
caatgtgtca accaatctga gctagagaaa tttgatggcg tttctcaagg taaatacaca     240
attggtctgg gccaaaccaa catgtctttt gtcaatgaca gagaagatat ctactcgatg     300
tccctaactg ttttgtctaa gttgatcaag agttacaaca tcgacaccaa caaaattggt     360
agattagaag tcggtactga aactctgatt gacaagtcca gtctgtcaa gtctgtcttg      420
atgcaattgt ttggtgaaaa cactgacgtc gaaggtattg acacgcttaa tgcctgttac     480
ggtggtacca acgcgttgtt caactctttg aactggatta atctaacgc atgggatggt      540
agagacgcca ttgtagtttg cggtgatatt gccatctacg ataagggtgc cgcaagacca     600
accggtggtg ccggtactgt tgctatgtgg atcggtcctg atgctccaat tgtatttgac     660
tctgtaagag cttcttacat ggaacacgcc tacgattttt acaagccaga tttcaccagc     720
gaatatcctt acgtcgatgg tcattttca ttaacttgtt acgtcaaggc tcttgatcaa      780
gtttacaaga gttattccaa gaaggctatt tctaaagggt tggttagcga tcccgctggt     840
tcggatgctt tgaacgtttt gaaatatttc gactacaacg ttttccatgt tccaacctgt     900
aaattggtca caaaatcata cggtagatta ctatataacg atttcagagc caatcctcaa     960
ttgttcccag aagttgacgc cgaattagct actcgcgatt atgacgaatc tttaaccgat    1020
aagaacattg aaaaaacttt tgttaatgtt gctaagccat tccacaaaga gagagttgcc    1080
caatctttga ttgttccaac aaacacaggt aacatgtaca ccgcatctgt ttatgccgcc    1140
tttgcatctc tattaaacta tgttggatct gacgacttac aaggcaagcg tgttggttta    1200
ttttcttacg gttccggttt agctgcatct ctatattctt gcaaaattgt tggtgacgtc    1260
caacatatta tcaaggaatt agatattact aacaaattag ccaagagaat caccgaaact    1320
ccaaaggatt acgaagctgc catcgaattg agagaaaatg cccatttgaa gaagaacttc    1380
aaacctcaag gttccattga gcatttgcaa agtggtgttt actacttgac caacatcgat    1440
gacaaattta aagatctta cgatgttaaa aaataa                               1476
```

<210> SEQ ID NO 3
<211> LENGTH: 1509
<212> TYPE: DNA
<213> ORGANISM: Artificial Sequence
<220> FEATURE:
<223> OTHER INFORMATION: Description of Artificial Sequence: Synthetic HMG-CoA reductase nucleotide sequence

<400> SEQUENCE: 3

```
atggttttaa ccaataaaac agtcatttct ggatcgaaag tcaaaagttt atcatctgcg      60
caatcgagct catcaggacc ttcatcatct agtgaggaag atgattcccg cgatattgaa     120
agcttggata gaaaatacg tccttttagaa gaattagaag cattattaag tagtggaaat     180
acaaaacaat tgaagaacaa agaggtcgct gccttggtta ttcacggtaa gttacctttg     240
tacgctttgg agaaaaaatt aggtgatact acgagagcgg ttgcggtacg taggaaggct     300
ctttcaattt tggcagaagc tcctgtatta gcatctgatc gttaccata taaaaattat     360
gactacgacc gcgtatttgg cgcttgttgt gaaaatgtta taggttacat gcctttgccc     420
gttggtgtta taggccccctt ggttatcgat ggtacatctt atcatatacc aatggcaact     480
acagagggtt gtttggtagc ttctgccatg cgtggctgta aggcaatcaa tgctggcggt     540
```

```
ggtgcaacaa ctgttttaac taaggatggt atgacaagag gcccagtagt ccgtttccca      600
actttgaaaa gatctggtgc ctgtaagata tggttagact cagaagaggg acaaaacgca      660
attaaaaaag cttttaactc tacatcaaga tttgcacgtc tgcaacatat tcaaacttgt      720
ctagcaggag atttactctt catgagattt agaacaacta ctggtgacgc aatgggtatg      780
aatatgattt ctaaaggtgt cgaatactca ttaaagcaaa tggtagaaga gtatggctgg      840
gaagatatgg aggttgtctc cgtttctggt aactactgta ccgacaaaaa accagctgcc      900
atcaactgga tcgaaggtcg tggtaagagt gtcgtcgcag aagctactat tcctggtgat      960
gttgtcagaa aagtgttaaa aagtgatgtt tccgcattgg ttgagttgaa cattgctaag     1020
aatttggttg gatctgcaat ggctgggtct gttggtggat ttaacgcaca tgcagctaat     1080
ttagtgacag ctgttttctt ggcattagga caagatcctg cacaaaatgt tgaaagttcc     1140
aactgtataa cattgatgaa agaagtggac ggtgatttga gaatttccgt atccatgcca     1200
tccatcgaag taggtaccat cggtggtggt actgttctag aaccacaagg tgccatgttg     1260
gacttattag gtgtaagagg cccgcatgct accgctcctg gtaccaacgc acgtcaatta     1320
gcaagaatag ttgcctgtgc cgtcttggca ggtgaattat ccttatgtgc tgccctagca     1380
gccggccatt tggttcaaag tcatatgacc cacaacagga aacctgctga accaacaaaa     1440
cctaacaatt tggacgccac tgatataaat cgtttgaaag atgggtccgt cacctgcatt     1500
aaatcctaa                                                             1509

<210> SEQ ID NO 4
<211> LENGTH: 1332
<212> TYPE: DNA
<213> ORGANISM: Artificial Sequence
<220> FEATURE:
<223> OTHER INFORMATION: Description of Artificial Sequence: Synthetic
      Mevalonate kinase nucleotide sequence

<400> SEQUENCE: 4
atgtcattac cgttcttaac ttctgcaccg ggaaaggtta ttattttgg tgaacactct       60 gctgtgtaca caagcctgc cgtcgctgct agtgtgtctg cgttgagaac ctacctgcta      120
ataagcgagt catctgcacc agatactatt gaattggact cccggacat tagctttaat      180 cataagtggt ccatcaatga tttcaatgcc atcaccgagg atcaagtaaa ctcccaaaaa     240
ttggccaagg ctcaacaagc caccgatggc ttgtctcagg aactcgttag tcttttggat     300
ccgttgttag ctcaactatc cgaatccttc cactaccatg cagcgttttg tttcctgtat     360
atgtttgttt gcctatgccc ccatgccaag aatattaagt tttcttttaaa gtctactta     420 cccatcggtg ctgggttggg ctcaagcgcc tctatttctg tatcactggc cttagctatg     480
gcctacttgg gggggttaat aggatctaat gacttggaaa agctgtcaga aaacgataag     540
catatagtga atcaatgggc cttcataggt gaaaagtgta ttcacggtac ccttcagga      600 atagataacg ctgtggccac ttatggtaat gccctgctat tgaaaaaga ctcacataat      660 ggaacaataa acacaaacaa ttttaagttc ttagatgatt tcccagccat tccaatgatc     720
ctaacctata ctagaattcc aaggtctaca aaagatcttg ttgctcgcgt tcgtgtgttg     780
gtcaccgaga aatttcctga agttatgaag ccaattctag atgccatggg tgaatgtgcc     840
ctacaaggct tagagatcat gactaagtta agtaaatgta aaggcaccga tgacgaggct     900
gtagaaacta ataatgaact gtatgaacaa ctattggaat tgataagaat aaatcatgga     960
ctgcttgtct caatcggtgt ttctcatcct ggattagaac ttattaaaaa tctgagcgat    1020
```

```
gatttgagaa ttggctccac aaaacttacc ggtgctggtg gcggcggttg ctctttgact    1080
ttgttacgaa gagacattac tcaagagcaa attgacagct tcaaaaagaa attgcaagat    1140
gattttagtt acgagacatt tgaaacagac ttgggtggga ctggctgctg tttgttaagc    1200
gcaaaaaatt tgaataaaga tcttaaaatc aaatccctag tattccaatt atttgaaaat    1260
aaaactacca caaagcaaca aattgacgat ctattattgc caggaaacac gaatttacca    1320
tggacttcat ag                                                        1332

<210> SEQ ID NO 5
<211> LENGTH: 1356
<212> TYPE: DNA
<213> ORGANISM: Artificial Sequence
<220> FEATURE:
<223> OTHER INFORMATION: Description of Artificial Sequence: Synthetic
      Phosphomevalonate kinase nucleotide sequence

<400> SEQUENCE: 5
atgtcagagt tgagagcctt cagtgcccca gggaaagcgt tactagctgg tgatatttta     60
gttttagata caaaatatga agcatttgta gtcggattat cggcaagaat gcatgctgta    120
gcccatcctt acggttcatt gcaagggtct gataagtttg aagtgcgtgt gaaaagtaaa    180
caatttaaag atggggagtg gctgtaccat ataagtccta aaagtggctt cattcctgtt    240
tcgataggcg gatctaagaa cccttcatt gaaaaagtta tcgctaacgt atttagctac    300
tttaaaccta acatggacga ctactgcaat agaaacttgt tcgttattga tattttctct    360
gatgatgcct accattctca ggaggatagc gttaccgaac atcgtggcaa cagaagattg    420
agttttcatt cgcacagaat tgaagaagtt cccaaaacag gctgggctc ctcggcaggt    480 ttagtcacag ttttaactac agctttggcc tcctttttg tatcggacct ggaaaataat    540
gtagacaaat atagagaagt tattcataat ttagcacaag ttgctcattg tcaagctcag    600
ggtaaaattg gaagcgggtt tgatgtagcg gcggcagcat atggatctat cagatataga    660
agattcccac ccgcattaat ctctaattg ccagatattg gaagtgctac ttacggcagt    720
aaactggcgc atttggttga tgaagaagac tggaatatta cgattaaag taaccattta    780 ccttcgggat taactttatg gatgggcgat attaagaatg gttcagaaac agtaaaactg    840
gtccagaagg taaaaaattg gtatgattcg catatgccag aaagcttgaa aatatataca    900
gaactcgatc atgcaaattc tagatttatg gatggactat ctaaactaga tcgcttacac    960
gagactcatg acgattacag cgatcagata tttgagtctc ttgagaggaa tgactgtacc   1020
tgtcaaaagt atcctgaaat cacagaagtt agagatgcag ttgccacaat tagacgttcc   1080
tttagaaaaa taactaaaga atctggtgcc gatatcgaac ctcccgtaca aactagctta   1140
ttggatgatt gccagacctt aaaaggagtt cttacttgct taatacctgg tgctggtggt   1200
tatgacgcca ttgcagtgat tactaagcaa gatgttgatc ttagggctca aaccgctaat   1260
gacaaaagat tttctaaggt tcaatggctg gatgtaactc aggctgactg gggtgttagg   1320
aaagaaaaag atccggaaac ttatcttgat aaatag                              1356

<210> SEQ ID NO 6
<211> LENGTH: 1191
<212> TYPE: DNA
<213> ORGANISM: Artificial Sequence
<220> FEATURE:
<223> OTHER INFORMATION: Description of Artificial Sequence: Synthetic
      Mevalonate pyrophosphate decarboxylase nucleotide
      sequence

<400> SEQUENCE: 6
```

```
atgaccgttt acacagcatc cgttaccgca cccgtcaaca tcgcaaccct taagtattgg    60
gggaaaaggg acacgaagtt gaatctgccc accaattcgt ccatatcagt gactttatcg   120
caagatgacc tcagaacgtt gacctctgcg gctactgcac ctgagtttga acgcgacact   180
ttgtggttaa atggagaacc acacagcatc gacaatgaaa gaactcaaaa ttgtctgcgc   240
gacctacgcc aattaagaaa ggaaatggaa tcgaaggacg cctcattgcc cacattatct   300
caatggaaac tccacattgt ctccgaaaat aactttccta cagcagctgg tttagcttcc   360
tccgctgctg gctttgctgc attggtctct gcaattgcta agttatacca attaccacag   420
tcaacttcag aaatatctag aatagcaaga aaggggtctg gttcagcttg tagatcgttg   480
tttggcggat acgtggcctg ggaaatggga aaagctgaag atggtcatga ttccatggca   540
gtacaaatcg cagacagctc tgactggcct cagatgaaag cttgtgtcct agttgtcagc   600
gatattaaaa aggatgtgag ttccactcag ggtatgcaat tgaccgtggc aacctccgaa   660
ctatttaaag aaagaattga acatgtcgta ccaaagagat ttgaagtcat gcgtaaagcc   720
attgttgaaa agatttcgc cacctttgca aaggaaacaa tgatggattc caactctttc   780
catgccacat gtttggactc tttccctcca atattctaca tgaatgacac ttccaagcgt   840
atcatcagtt ggtgccacac cattaatcag ttttacggag aaacaatcgt tgcatacacg   900
tttgatgcag gtccaaatgc tgtgttgtac tacttagctg aaaatgagtc gaaactcttt   960
gcatttatct ataaattgtt tggctctgtt cctggatggg acaagaaatt tactactgag  1020
cagcttgagg ctttcaacca tcaatttgaa tcatctaact ttactgcacg tgaattggat  1080
cttgagttgc aaaaggatgt tgccagagtg attttaactc aagtcggttc aggcccacaa  1140
gaaacaaacg aatctttgat tgacgcaaag actggtctac caaggaata a             1191
```

<210> SEQ ID NO 7
<211> LENGTH: 9253
<212> TYPE: DNA
<213> ORGANISM: Artificial Sequence
<220> FEATURE:
<223> OTHER INFORMATION: Description of Artificial Sequence: Synthetic "single operon" nucleotide sequence

<400> SEQUENCE: 7

```
gacgcttttt atcgcaactc tctactgttt ctccataccc gttttttttgg gctagcagga    60
ggaattcacc atggtacccg ggaggaggat tactatatgc aaacggaaca cgtcatttta   120
ttgaatgcac agggagttcc cacgggtacg ctggaaaagt atgccgcaca cacggcagac   180
acccgcttac atctcgcgtt ctccagttgg ctgtttaatg ccaaaggaca attattagtt   240
acccgccgcg cactgagcaa aaaagcatgg cctggcgtgt ggactaactc ggtttgtggg   300
cacccacaac tgggagaaag caacgaagac gcagtgatcc gccgttgccg ttatgagctt   360
ggcgtggaaa ttacgcctcc tgaatctatc tatcctgact ttcgctaccg cgccaccgat   420
ccgagtggca ttgtggaaaa tgaagtgtgt ccggtatttg ccgcacgcac cactagtgcg   480
ttacagatca atgatgatga agtgatggat tatcaatggt gtgatttagc agatgtatta   540
cacggtattg atgccacgcc gtgggcgttc agtccgtgga tggtgatgca ggcgacaaat   600
cgcgaagcca gaaacgatt atctgcattt acccagctta ataacccgg ggatcctcta   660
gagtcgacta ggaggaatat aaaatgaaaa attgtgtcat cgtcagtgcg gtacgtactg   720
ctatcggtag ttttaacggt tcactcgctt ccaccagcgc catcgacctg ggggcgacag  780
taattaaagc cgccattgaa cgtgcaaaaa tcgattcaca acacgttgat gaagtgatta  840
```

```
tgggtaacgt gttacaagcc gggctggggc aaaatccggc gcgtcaggca ctgttaaaaa      900
gcgggctggc agaaacggtg tgcggattca cggtcaataa agtatgtggt tcgggtctta      960
aaagtgtggc gcttgccgcc caggccattc aggcaggtca ggcgcagagc attgtggcgg     1020
ggggtatgga aaatatgagt ttagccccct acttactcga tgcaaaagca cgctctggtt     1080
atcgtcttgg agacggacag gtttatgacg taatcctgcg cgatggcctg atgtgcgcca     1140
cccatggtta tcatatgggg attaccgccg aaaacgtggc taaagagtac ggaattaccc     1200
gtgaaatgca ggatgaactg gcgctacatt cacagcgtaa agcggcagcc gcaattgagt     1260
ccggtgcttt tacagccgaa atcgtcccgg taaatgttgt cactcgaaag aaaaccttcg     1320
tcttcagtca agacgaattc ccgaaagcga attcaacggc tgaagcgtta ggtgcattgc     1380
gcccggcctt cgataaagca ggaacagtca ccgctgggaa cgcgtctggt attaacgacg     1440
gtgctgccgc tctggtgatt atggaagaat ctgcggcgct ggcagcaggc cttacccccc     1500
tggctcgcat taaaagttat gccagcggtg gcgtgccccc cgcattgatg ggtatggggc     1560
cagtacctgc cacgcaaaaa gcgttacaac tggcggggct gcaactggcg gatattgatc     1620
tcattgaggc taatgaagca tttgctgcac agttccttgc cgttgggaaa aacctgggct     1680
ttgattctga gaaagtgaat gtcaacggcg gggccatcgc gctcgggcat cctatcggtg     1740
ccagtggtgc tcgtattctg gtcacactat tacatgccat gcaggcacgc gataaaacgc     1800
tggggctggc aacactgtgc attggcggcg gtcagggaat tgcgatggtg attgaacggt     1860
tgaattaagg aggacagcta aatgaaactc tcaactaaac tttgttggtg tggtattaaa     1920
ggaagactta ggccgcaaaa gcaacaacaa ttacacaata caaacttgca aatgactgaa     1980
ctaaaaaaac aaaagaccgc tgaacaaaaa accagacctc aaaatgtcgg tattaaaggt     2040
atccaaattt acatcccaac tcaatgtgtc aaccaatctg agctagagaa atttgatggc     2100
gtttctcaag gtaaatacac aattggtctg ggccaaacca acatgtcttt tgtcaatgac     2160
agagaagata tctactcgat gtccctaact gttttgtcta agttgatcaa gagttacaac     2220
atcgacacca acaaaattgg tagattagaa gtcggtactg aaactctgat tgacaagtcc     2280
aagtctgtca agtctgtctt gatgcaattg tttggtgaaa acactgacgt cgaaggtatt     2340
gacacgctta atgcctgtta cggtggtacc aacgcgttgt tcaactcttt gaactggatt     2400
gaatctaacg catgggatgg tagagacgcc attgtagttt gcggtgatat tgccatctac     2460
gataagggtg ccgcaagacc aaccggtggt gccggtactg ttgctatgtg gatcggtcct     2520
gatgctccaa ttgtatttga ctctgtaaga gcttcttaca tggaacacgc ctacgatttt     2580
tacaagccag atttcaccag cgaatatcct tacgtcgatg gtcattttc attaacttgt      2640
tacgtcaagg ctcttgatca agtttacaag agttattcca agaaggctat ttctaaaggg     2700
ttggttagcg atcccgctgg ttcggatgct ttgaacgttt tgaaatattt cgactacaac     2760
gttttccatg ttccaacctg taaattggtc acaaaatcat acggtagatt actatataac     2820
gatttcagag ccaatcctca attgttccca gaagttgacg ccgaattagc tactcgcgat     2880
tatgacgaat ctttaaccga taagaacatt gaaaaaactt tgttaatgt tgctaagcca      2940
ttccacaaag agagagttgc ccaatctttg attgttccaa caaacacagg taacatgtac     3000
accgcatctg tttatgccgc cttttgcatct ctattaaact atgttggatc tgacgactta    3060
caaggcaagc gtgttggttt attttcttac ggttccggtt tagctgcatc tctatattct     3120
tgcaaaattg ttggtgacgt ccaacatatt atcaaggaat tagatattac taacaaatta     3180
gccaagagaa tcaccgaaac tccaaaggat tacgaagctg ccatcgaatt gagagaaaat     3240
```

```
gcccatttga agaagaactt caaacctcaa ggttccattg agcatttgca aagtggtgtt    3300
tactacttga ccaacatcga tgacaaattt agaagatctt acgatgttaa aaataagga    3360 ggattacact atggttttaa ccaataaaac agtcatttct ggatcgaaag tcaaaagttt    3420
atcatctgcg caatcgagct catcaggacc ttcatcatct agtgaggaag atgattcccg    3480
cgatattgaa agcttggata agaaaatacg tcctttagaa gaattagaag cattattaag    3540
tagtggaaat acaaaacaat tgaagaacaa agaggtcgct gccttggtta ttcacggtaa    3600
gttacctttg tacgctttgg agaaaaaatt aggtgatact acgagagcgg ttgcggtacg    3660
taggaaggct cttctcaattt tggcagaagc tcctgtatta gcatctgatc gtttaccata    3720
taaaaattat gactacgacc gcgtatttgg cgcttgttgt gaaaatgtta taggttacat    3780
gcctttgccc gttggtgtta taggcccctt ggttatcgat ggtacatctt atcatatacc    3840
aatggcaact acagagggtt gtttggtagc ttctgccatg cgtggctgta aggcaatcaa    3900
tgctggcggt ggtgcaacaa ctgttttaac taaggatgat atgacaagag gcccagtagt    3960
ccgtttccca actttgaaaa gatctggtgc ctgtaagata tggttagact cagaagaggg    4020
acaaaacgca attaaaaaag cttttaactc tacatcaaga tttgcacgtc tgcaacatat    4080
tcaaacttgt ctagcaggag atttactctt catgagattt agaacaacta ctggtgacgc    4140
aatgggtatg aatatgattt ctaaaggtgt cgaatactca ttaaagcaaa tggtagaaga    4200
gtatggctgg gaagatatgg aggttgtctc cgtttctggt aactactgta ccgacaaaaa    4260
accagctgcc atcaactgga tcgaaggtcg tggtaagagt gtcgtcgcag aagctactat    4320
tcctggtgat gttgtcagaa aagtgttaaa aagtgatgtt ccgcattgg ttgagttgaa    4380 cattgctaag aatttggttg gatctgcaat ggctgggtct gttggtggat ttaacgcaca    4440
tgcagctaat ttagtgacag ctgttttctt ggcattagga caagatcctg cacaaaatgt    4500
tgaaagttcc aactgtataa cattgatgaa agaagtggac ggtgatttga gaatttccgt    4560
atccatgcca tccatcgaag taggtaccat cggtggtggt actgttctag aaccacaagg    4620
tgccatgttg gacttattag gtgtaagagg cccgcatgct accgctcctg gtaccaacgc    4680
acgtcaatta gcaagaatag ttgcctgtgc cgtcttggca ggtgaattat ccttatgtgc    4740
tgccctagca gccggccatt tggttcaaag tcatatgacc cacaacagga aacctgctga    4800
accaacaaaa cctaacaatt tggacgccac tgatataaat cgtttgaaag atgggtccgt    4860
cacctgcatt aaatcctaag tcgacctgca gtaggaggaa ttaaccatgt cattaccgtt    4920
cttaacttct gcaccgggaa aggttattat ttttggtgaa cactctgctg tgtacaacaa    4980
gcctgccgtc gctgctagtg tgtctgcgtt gagaacctac ctgctaataa gcgagtcatc    5040
tgcaccagat actattgaat tggacttccc ggacattagc tttaatcata agtggtccat    5100
caatgatttc aatgccatca ccgaggatca agtaaactcc caaaaattgg ccaaggctca    5160
acaagccacc gatggcttgt ctcaggaact cgttagtctt ttggatccgt tgttagctca    5220
actatccgaa tccttccact accatgcagc gttttgtttc ctgtatatgt ttgtttgcct    5280
atgcccccat gccaagaata ttaagttttc tttaaagtct actttaccca tcggtgctgg    5340
gttgggctca agcgcctcta tttctgtatc actggcctta gctatggcct acttgggggg    5400
gttaatagga tctaatgact tggaaaagct gtcagaaaac gataagcata tagtgaatca    5460
atgggccttc ataggtgaaa agtgtattca cggtaccccct tcaggaatag ataacgctgt    5520
ggccacttat ggtaatgccc tgctatttga aaaagactca cataatggaa caataaacac    5580
aaacaatttt aagttcttag atgatttccc agccattcca atgatcctaa cctatactag    5640
```

```
aattccaagg tctacaaaag atcttgttgc tcgcgttcgt gtgttggtca ccgagaaatt    5700
tcctgaagtt atgaagccaa ttctagatgc catgggtgaa tgtgccctac aaggcttaga    5760
gatcatgact aagttaagta aatgtaaagg caccgatgac gaggctgtag aaactaataa    5820
tgaactgtat gaacaactat tggaattgat aagaataaat catggactgc ttgtctcaat    5880
cggtgtttct catcctggat tagaacttat taaaaatctg agcgatgatt tgagaattgg    5940
ctccacaaaa cttaccggtg ctggtggcgg cggttgctct ttgactttgt tacgaagaga    6000
cattactcaa gagcaaattg acagcttcaa aaagaaattg caagatgatt ttagttacga    6060
gacatttgaa acagacttgg gtgggactgg ctgctgtttg ttaagcgcaa aaaatttgaa    6120
taaagatctt aaaatcaaat ccctagtatt ccaattattt gaaaataaaa ctaccacaaa    6180
gcaacaaatt gacgatctat tattgccagg aaacacgaat ttaccatgga cttcatagga    6240
ggcagatcaa atgtcagagt tgagagcctt cagtgcccca gggaaagcgt tactagctgg    6300
tggatattta gttttagata caaaatatga agcatttgta gtcggattat cggcaagaat    6360
gcatgctgta gcccatcctt acggttcatt gcaagggtct gataagtttg aagtgcgtgt    6420
gaaaagtaaa caatttaaag atggggagtg gctgtaccat ataagtccta aaagtggctt    6480
cattcctgtt tcgataggcg gatctaagaa ccctttcatt gaaaaagtta tcgctaacgt    6540
atttagctac tttaaaccta acatggacga ctactgcaat agaaacttgt tcgttattga    6600
tattttctct gatgatgcct accattctca ggaggatagc gttaccgaac atcgtggcaa    6660
cagaagattg agttttcatt cgcacagaat tgaagaagtt cccaaaacag gctgggctc     6720
ctcggcaggt ttagtcacag ttttaactac agctttggcc tcctttttg tatcggacct     6780
ggaaaataat gtagacaaat atagagaagt tattcataat ttagcacaag ttgctcattg    6840
tcaagctcag ggtaaaattg gaagcgggtt tgatgtagcg gcggcagcat atggatctat    6900
cagatataga agattcccac ccgcattaat ctctaatttg ccagatattg gaagtgctac    6960
ttacggcagt aaactggcgc atttggttga tgaagaagac tggaatatta cgattaaaag    7020
taaccattta ccttcgggat taactttatg gatgggcgat attaagaatg gttcagaaac    7080
agtaaaactg gtccagaagg taaaaaattg gtatgattcg catatgccag aaagcttgaa    7140
aatatataca gaactcgatc atgcaaattc tagatttatg gatggactat ctaaactaga    7200
tcgcttacac gagactcatg acgattacag cgatcagata tttgagtctc ttgagaggaa    7260
tgactgtacc tgtcaaaagt atcctgaaat cacagaagtt agagatgcag ttgccacaat    7320
tagacgttcc tttagaaaaa taactaaaga atctggtgcc gatatcgaac ctcccgtaca    7380
aactagctta ttggatgatt gccagacctt aaaaggagtt cttacttgct taatacctgg    7440
tgctggtggt tatgacgcca ttgcagtgat tactaagcaa gatgttgatc ttagggctca    7500
aaccgctaat gacaaaagat tttctaaggt tcaatggctg gatgtaactc aggctgactg    7560
gggtgttagg aagaaaaaag atccggaaac ttatcttgat aaataggagg taatactcat    7620
gaccgtttac acagcatccg ttaccgcacc cgtcaacatc gcaacccttt agtattgggg    7680
gaaaagggac acgaagttga atctgcccac caattcgtcc atatcagtga ctttatcgca    7740
agatgacctc agaacgttga cctctgcggc tactgcacct gagtttgaac gcgacacttt    7800
gtggttaaat ggagaaccac acagcatcga caatgaaaga actcaaaatt gtctgcgcga    7860
cctacgccaa ttaagaaagg aaatggaatc gaaggacgcc tcattgccca cattatctca    7920
atggaaactc cacattgtct ccgaaaataa ctttcctaca gcagctggtt tagcttcctc    7980
cgctgctggc tttgctgcat tggtctctgc aattgctaag ttataccaat taccacagtc    8040
```

-continued

```
aacttcagaa atatctagaa tagcaagaaa ggggtctggt tcagcttgta gatcgttgtt    8100
tggcggatac gtggcctggg aaatgggaaa agctgaagat ggtcatgatt ccatggcagt    8160
acaaatcgca gacagctctg actggcctca gatgaaagct tgtgtcctag ttgtcagcga    8220
tattaaaaag gatgtgagtt ccactcaggg tatgcaattg accgtggcaa cctccgaact    8280
atttaaagaa agaattgaac atgtcgtacc aaagagattt gaagtcatgc gtaaagccat    8340
tgttgaaaaa gatttcgcca cctttgcaaa ggaaacaatg atggattcca actctttcca    8400
tgccacatgt ttggactctt tccctccaat attctacatg aatgacactt ccaagcgtat    8460
catcagttgg tgccacacca ttaatcagtt ttacggagaa acaatcgttg catacacgtt    8520
tgatgcaggt ccaaatgctg tgttgtacta cttagctgaa aatgagtcga aactctttgc    8580
atttatctat aaattgtttg ctctcgttcc tggatgggac aagaaattta ctactgagca    8640
gcttgaggct ttcaaccatc aatttgaatc atctaacttt actgcacgtg aattggatct    8700
tgagttgcaa aaggatgttg ccagagtgat tttaactcaa gtcggttcag cccacaagaa    8760
aacaaacgaa tctttgattg acgcaaagac tggtctacca aaggaataac tgcaggcatg    8820
caagcttggc tgttttggcg gatgagagaa gattttcagc ctgatacaga ttaaatcaga    8880
acgcagaagc ggtctgataa aacagaattt gcctggcggc agtagcgcgg tggtcccacc    8940
tgaccccatg ccgaactcag aagtgaaacg ccgtagcgcc gatggtagtg tggggtctcc    9000
ccatgcgaga gtagggaact gccaggcatc aaataaaacg aaaggctcag tcgaaagact    9060 gggccttttcg ttttatctgt tgtttgtcgg tgaacgctct cctgagtagg acaaatccgc    9120
cgggagcgga tttgaacgtt gcgaagcaac ggcccggagg gtggcgggca ggacgcccgc    9180
cataaactgc caggcatcaa attaagcaga aggccatcct gacggatggc cttttttgcgt    9240 ttctacaaac tct                                                      9253
```

<210> SEQ ID NO 8
<211> LENGTH: 4760
<212> TYPE: DNA
<213> ORGANISM: Artificial Sequence
<220> FEATURE:
<223> OTHER INFORMATION: Description of Artificial Sequence: Synthetic
      "MEVT" operon nucleotide sequence

<400> SEQUENCE: 8

```
gacgcttttt atcgcaactc tctactgttt ctccataccc gttttttttgg gctagcagga    60 ggaattcacc atggtacccg gggatcctct agagtcgact aggaggaata taaaatgaaa    120
aattgtgtca tcgtcagtgc ggtacgtact gctatcggta gttttaacgg ttcactcgct    180
tccaccagcg ccatcgacct gggggcgaca gtaattaaag ccgccattga acgtgcaaaa    240
atcgattcac aacacgttga tgaagtgatt atgggtaacg tgttacaagc cgggctgggg    300
caaaatccgg cgcgtcaggc actgttaaaa agcgggctgg cagaaacggt gtgcggattc    360
acggtcaata agtatgtgg ttcgggtctt aaaagtgtgg cgcttgccgc ccaggccatt    420
caggcaggtc aggcgcagag cattgtggcg ggggtatgg aaaatatgag tttagccccc    480
tacttactcg atgcaaaagc acgctctggt tatcgtcttg agacggaca ggtttatgac    540 gtaatcctgc gcgatggcct gatgtgcgcc acccatggtt atcatatggg gattaccgcc    600
gaaaacgtgg ctaaagagta cggaattacc cgtgaaatgc aggatgaact ggcgctacat    660
tcacagcgta aagcggcagc cgcaattgag tccggtgctt ttacagccga atcgtcccg    720 gtaaatgttg tcactcgaaa gaaaacccttc gtcttcagtc aagacgaatt cccgaaagcg    780
aattcaacgg ctgaagcgtt aggtgcattg cgcccggcct tcgataaagc aggaacagtc    840
```

```
accgctggga acgcgtctgg tattaacgac ggtgctgccg ctctggtgat tatggaagaa    900
tctgcggcgc tggcagcagg ccttacccc ctggctcgca ttaaaagtta tgccagcggt    960
ggcgtgcccc ccgcattgat gggtatgggg ccagtacctg ccacgcaaaa agcgttacaa   1020
ctggcggggc tgcaactggc ggatattgat ctcattgagg ctaatgaagc atttgctgca   1080
cagttccttg ccgttgggaa aaacctgggc tttgattctg agaaagtgaa tgtcaacggc   1140
ggggccatcg cgctcgggca tcctatcggt gccagtggtg ctcgtattct ggtcacacta   1200
ttacatgcca tgcaggcacg cgataaaacg ctggggctgg caacactgtg cattggcggc   1260
ggtcagggaa ttgcgatggt gattgaacgg ttgaattaag gaggacagct aaatgaaact   1320
ctcaactaaa ctttgttggt gtggtattaa aggaagactt aggccgcaaa agcaacaaca   1380
attcacaat acaaacttgc aaatgactga actaaaaaaa caaagaccg ctgaacaaaa    1440
aaccagacct caaatgtcg gtattaaagg tatccaaatt tacatcccaa ctcaatgtgt    1500
caaccaatct gagctagaga aatttgatgg cgtttctcaa ggtaaataca caattggtct    1560
gggccaaacc aacatgtctt ttgtcaatga cagagaagat atctactcga tgtccctaac    1620
tgttttgtct aagttgatca agagttacaa catcgacacc aacaaaattg gtagattaga   1680
agtcggtact gaaactctga ttgacaagtc caagtctgtc aagtctgtct tgatgcaatt    1740
gtttggtgaa aacactgacg tcgaaggtat tgacacgctt aatgcctgtt acggtggtac    1800
caacgcgttg ttcaactctt tgaactggat tgaatctaac gcatgggatg gtagagacgc   1860
cattgtagtt tgcggtgata ttgccatcta cgataagggt gccgcaagac caaccggtgg    1920
tgccggtact gttgctatgt ggatcggtcc tgatgctcca attgtatttg actctgtaag    1980
agcttcttac atggaacacg cctacgattt ttacaagcca gatttcacca gcgaatatcc    2040
ttacgtcgat ggtcattttt cattaacttg ttacgtcaag gctcttgatc aagtttacaa    2100
gagttattcc aagaaggcta tttctaaagg gttggttagc gatcccgctg ttcggatgc    2160
tttgaacgtt ttgaaatatt tcgactacaa cgttttccat gttccaacct gtaaattggt    2220
cacaaaatca tacggtagat tactatataa cgatttcaga gccaatcctc aattgttccc    2280
agaagttgac gccgaattag ctactcgcga ttatgacgaa tctttaaccg ataagaacat    2340
tgaaaaaact tttgttaatg ttgctaagcc attccacaaa gagagagttg cccaatcttt   2400
gattgttcca acaaacacag gtaacatgta caccgcatct gtttatgccg cctttgcatc    2460
tctattaaac tatgttggat ctgacgactt acaaggcaag cgtgttggtt tattttctta    2520
cggttccggt ttagctgcat ctctatattc ttgcaaaatt gttggtgacg tccaacatat    2580
tatcaaggaa ttagatatta ctaacaaatt agccaagaga atcaccgaaa ctccaaagga    2640
ttacgaagct gccatcgaat tgagagaaaa tgcccatttg aagaagaact tcaaacctca    2700
aggttccatt gagcatttgc aaagtggtgt ttactacttg accacatcg atgcaaaatt   2760
tagaagatct tacgatgtta aaaataagg aggattacac tatggtttta accaataaaa    2820
cagtcatttc tggatcgaaa gtcaaaagtt tatcatctgc gcaatcgagc tcatcaggac    2880
cttcatcatc tagtgaggaa gatgattccc gcgatattga aagcttggat aagaaaatac    2940
gtcctttaga agaattagaa gcattattaa gtagtggaaa tacaaaacaa ttgaagaaca    3000
aagaggtcgc tgccttggtt attcacggta agttaccttt gtacgctttg gagaaaaat    3060
taggtgatac tacgagagcg gttgcggtac gtaggaaggc tctttcaatt ttggcagaag    3120
ctcctgtatt agcatctgat cgtttaccat ataaaaatta tgactacgac cgcgtatttg    3180
gcgcttgttg tgaaaatgtt ataggttaca tgcctttgcc cgttggtgtt ataggcccct    3240
```

```
tggttatcga tggtacatct tatcatatac caatggcaac tacagagggt tgtttggtag    3300
cttctgccat gcgtggctgt aaggcaatca atgctggcgg tggtgcaaca actgttttaa    3360
ctaaggatgg tatgacaaga ggcccagtag tccgtttccc aactttgaaa agatctggtg    3420
cctgtaagat atggttagac tcagaagagg gacaaaacgc aattaaaaaa gcttttaact    3480
ctacatcaag atttgcacgt ctgcaacata ttcaaacttg tctagcagga gatttactct    3540
tcatgagatt tagaacaact actggtgacg caatgggtat gaatatgatt tctaaaggtg    3600
tcgaatactc attaaagcaa atggtagaag agtatggctg ggaagatatg gaggttgtct    3660
ccgtttctgg taactactgt accgacaaaa aaccagctgc catcaactgg atcgaaggtc    3720
gtggtaagag tgtcgtcgca gaagctacta ttcctggtga tgttgtcaga aaagtgttaa    3780
aaagtgatgt ttccgcattg gttgagttga acattgctaa gaatttggtt ggatctgcaa    3840
tggctgggtc tgttggtgga tttaacgcac atgcagctaa tttagtgaca gctgttttct    3900
tggcattagg acaagatcct gcacaaaatg ttgaaagttc caactgtata acattgatga    3960
aagaagtgga cggtgatttg agaatttccg tatccatgcc atccatcgaa gtaggtacca    4020
tcggtggtgg tactgttcta gaaccacaag gtgccatgtt ggacttatta ggtgtaagag    4080
gcccgcatgc taccgctcct ggtaccaacg cacgtcaatt agcaagaata gttgcctgtg    4140
ccgtcttggc aggtgaatta tccttatgtg ctgccctagc agccggccat ttggttcaaa    4200
gtcatatgac ccacaacagg aaacctgctg aaccaacaaa acctaacaat tggacgcca    4260 ctgatataaa tcgtttgaaa gatgggtccg tcacctgcat aaatcctaa gtcgacctgc    4320 aggcatgcaa gcttggctgt tttggcggat gagagaagat tttcagcctg atacagatta    4380
aatcagaacg cagaagcggt ctgataaaac agaatttgcc tggcggcagt agcgcggtgg    4440
tcccacctga ccccatgccg aactcagaag tgaaacgccg tagcgccgat ggtagtgtgg    4500
ggtctcccca tgcgagagta gggaactgcc aggcatcaaa taaaacgaaa ggctcagtcg    4560
aaagactggg cctttcgttt tatctgttgt ttgtcggtga acgctctcct gagtaggaca    4620
aatccgccgg gagcggattt gaacgttgcg aagcaacggc ccggagggtg cgggcagga    4680 cgcccgccat aaactgccag gcatcaaatt aagcagaagg ccatcctgac ggatggcctt    4740
tttgcgtttc tacaaactct                                                4760
```

```
<210> SEQ ID NO 9
<211> LENGTH: 4482
<212> TYPE: DNA
<213> ORGANISM: Artificial Sequence
<220> FEATURE:
<223> OTHER INFORMATION: Description of Artificial Sequence: Synthetic
      "MEVB" operon nucleotide sequence

<400> SEQUENCE: 9
gcgcaacgca attaatgtga gttagctcac tcattaggca ccccaggctt tacactttat      60
gcttccggct cgtatgttgt gtggaattgt gagcggataa caatttcaca caggaaacag     120
ctatgaccat gattacgcca agcgcgcaat taaccctcac taaagggaac aaaagctggg     180
taccgggccc ccctcgagg tcgacggtat cgataagctt gatatcgaat tcctgcagta     240
ggaggaatta accatgtcat taccgttctt aacttctgca ccgggaaagg ttattatttt     300
tggtgaacac tctgctgtgt acaacaagcc tgccgtcgct gctagtgtgt ctgcgttgag     360
aacctacctg ctaataagcg agtcatctgc accagatact attgaattgg acttcccgga     420
cattagcttt aatcataagt ggtccatcaa tgatttcaat gccatcaccg aggatcaagt     480
```

```
aaactcccaa aaattggcca aggctcaaca agccaccgat ggcttgtctc aggaactcgt    540
tagtcttttg gatccgttgt tagctcaact atccgaatcc ttccactacc atgcagcgtt    600
ttgtttcctg tatatgtttg tttgcctatg cccccatgcc aagaatatta gtttctttt    660 aaagtctact ttacccatcg gtgctgggtt gggctcaagc gcctctattt ctgtatcact    720
ggccttagct atggcctact tgggggggtt aataggatct aatgacttgg aaaagctgtc    780
agaaaacgat aagcatatag tgaatcaatg ggccttcata ggtgaaaagt gtattcacgg    840
taccccttca ggaatagata acgctgtggc cacttatggt aatgccctgc tatttgaaaa    900
agactcacat aatggaacaa taaacacaaa caattttaag ttcttagatg atttcccagc    960
cattccaatg atcctaacct atactagaat tccaaggtct acaaaagatc ttgttgctcg   1020
cgttcgtgtg ttggtcaccg agaaatttcc tgaagttatg aagccaattc tagatgccat   1080
gggtgaatgt gccctacaag gcttagagat catgactaag ttaagtaaat gtaaaggcac   1140
cgatgacgag gctgtagaaa ctaataatga actgtatgaa caactattgg aattgataag   1200
aataaatcat ggactgcttg tctcaatcgg tgtttctcat cctggattag aacttattaa   1260
aaatctgagc gatgatttga gaattggctc cacaaaactt accggtgctg gtggcggcgg   1320
ttgctctttg actttgttac gaagagacat tactcaagag caaattgaca gcttcaaaaa   1380
gaaattgcaa gatgatttta gttacgagac atttgaaaca gacttgggtg ggactggctg   1440
ctgtttgtta agcgcaaaaa atttgaataa agatcttaaa atcaaatccc tagtattcca   1500
attatttgaa aataaaacta ccacaaagca acaaattgac gatctattat tgccaggaaa   1560
cacgaattta ccatggactt cataggaggc agatcaaatg tcagagttga gagccttcag   1620
tgccccaggg aaagcgttac tagctggtgg atatttagtt ttagatacaa aatatgaagc   1680
atttgtagtc ggattatcgg caagaatgca tgctgtagcc catccttacg gttcattgca   1740
agggtctgat aagtttgaag tgcgtgtgaa aagtaaacaa tttaaagatg gggagtggct   1800
gtaccatata agtcctaaaa gtggcttcat tcctgtttcg ataggcggat ctaagaaccc   1860
tttcattgaa aaagttatcg ctaacgtatt tagctacttt aaacctaaca tggacgacta   1920
ctgcaataga aacttgttcg ttattgatat tttctctgat gatgcctacc attctcagga   1980
ggatagcgtt accgaacatc gtggcaacag aagattgagt tttcattcgc acagaattga   2040
agaagttccc aaaacagggc tgggctcctc ggcaggttta gtcacagttt taactacagc   2100
tttggcctcc ttttttgtat cggacctgga aaataatgta gacaaatata gagaagttat   2160
tcataattta gcacaagttg ctcattgtca agctcagggt aaaattggaa gcgggtttga   2220
tgtagcggcg gcagcatatg gatctatcag atatagaaga ttcccacccg cattaatctc   2280
taatttgcca gatattggaa gtgctactta cggcagtaaa ctggcgcatt tggttgatga   2340
agaagactgg aatattacga ttaaaagtaa ccatttacct tcgggattaa ctttatggat   2400
gggcgatatt aagaatggtt cagaaacagt aaaactggtc cagaaggtaa aaattggta   2460 tgattcgcat atgccagaaa gcttgaaaat atatacagaa ctcgatcatg caaattctag   2520
atttatggat ggactatcta aactagatcg cttacgcgag actcatgacg attacagcga   2580
tcagatattt gagtctcttg agaggaatga ctgtacctgt caaaagtatc ctgaaatcac   2640
agaagttaga gatgcagttg ccacaattag acgttccttt agaaaaataa ctaaagaatc   2700
tggtgccgat atcgaacctc ccgtacaaac tagcttattg gatgattgcc agaccttaaa   2760
aggagttctt acttgcttaa tacctggtgc tggtggttat gacgccattg cagtgattac   2820
taagcaagat gttgatctta gggctcaaac cgctaatgac aaaagatttt ctaaggttca   2880
```

-continued

```
atggctggat gtaactcagg ctgactgggg tgttaggaaa gaaaaagatc cggaaactta      2940
tcttgataaa taggaggtaa tactcatgac cgtttacaca gcatccgtta ccgcacccgt      3000
caacatcgca acccttaagt attggggaa aagggacacg aagttgaatc tgcccaccaa       3060
ttcgtccata tcagtgactt tatcgcaaga tgacctcaga acgttgacct ctgcggctac      3120
tgcacctgag tttgaacgcg acactttgtg gttaaatgga gaaccacaca gcatcgacaa      3180
tgaaagaact caaaattgtc tgcgcgacct acgccaatta agaaggaaa tggaatcgaa       3240 ggacgcctca ttgcccacat tatctcaatg gaaactccac attgtctccg aaaataactt     3300
tcctacagca gctggtttag cttcctccgc tgctggcttt gctgcattgg tctctgcaat     3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taagaaaga attgaacatg tcgtaccaaa     3660
gagatttgaa gtcatgcgta aagccattgt tgaaaaagat ttcgccaccct ttgcaaagga   3720 aacaatgatg gattccaact ctttccatgc cacatgtttg gactctttcc ctccaatatt    3780
ctacatgaat gacacttcca agcgtatcat cagttggtgc cacaccatta atcagtttta    3840
cggagaaaca atcgttgcat acacgtttga tgcaggtcca aatgctgtgt tgtactactt    3900
agctgaaaat gagtcgaaac tctttgcatt tatctataaa ttgtttggct ctgttcctgg   3960
atgggacaag aaatttacta ctgagcagct tgaggctttc aaccatcaat ttgaatcatc   4020
taactttact gcacgtgaat tggatcttga gttgcaaaag gatgttgcca gagtgatttt   4080
aactcaagtc ggttcaggcc cacaagaaac aaacgaatct ttgattgacg caaagactgg   4140
tctaccaaag gaataactgc agcccggggg atccactagt tctagagcgg ccgccaccgc   4200
ggtggagctc caattcgccc tatagtgagt cgtattacgc gcgctcactg gccgtcgttt   4260
tacaacgtcg tgactgggaa aaccctggcg ttacccaact taatcgcctt gcagcacatc   4320
cccctttcgc cagctggcgt aatagcgaag aggcccgcac cgatcgccct tcccaacagt   4380
tgcgcagcct gaatggcgaa tggaaattgt aagcgttaat attttgttaa aattcgcgtt   4440
aaatttttgt taaatcagct cattttttaa ccaataggcc ga                       4482
```

<210> SEQ ID NO 10
<211> LENGTH: 549
<212> TYPE: DNA
<213> ORGANISM: Artificial Sequence
<220> FEATURE:
<223> OTHER INFORMATION: Description of Artificial Sequence: Synthetic
      Isopentenyl pyrophosphate isomerase (idi)
      nucleotide sequence

<400> SEQUENCE: 10

```
atgcaaacgg aacacgtcat tttattgaat gcacagggag ttcccacggg tacgctggaa      60
aagtatgccg cacacacggc agacacccgc ttacatctcg cgttctccag ttggctgttt     120
aatgccaaag acaattatt agttacccgc cgcgcactga gcaaaaaagc atggcctggc     180
gtgtggacta ctcggtttg tgggcaccca caactgggag aaagcaacga agacgcagtg     240
atccgccgtt gccgttatga gcttggcgtg gaaattacgc ctcctgaatc tatctatcct     300
gactttcgct accgcgccac cgatccgagt ggcattgtgg aaaatgaagt gtgtccggta     360
tttgccgcac gcaccactag tgcgttacag atcaatgatg atgaagtgat ggattatcaa     420
```

-continued

```
tggtgtgatt tagcagatgt attacacggt attgatgcca cgccgtgggc gttcagtccg    480
tggatggtga tgcaggcgac aaatcgcgaa gccagaaaac gattatctgc atttacccag    540
cttaaataa                                                            549
```

<210> SEQ ID NO 11
<211> LENGTH: 900
<212> TYPE: DNA
<213> ORGANISM: Artificial Sequence
<220> FEATURE:
<223> OTHER INFORMATION: Description of Artificial Sequence: Synthetic
      Farnesyl pyrophosphate synthase (ispA) nucleotide
      sequence

<400> SEQUENCE: 11

```
atggactttc cgcagcaact cgaagcctgc gttaagcagg ccaaccaggc gctgagccgt     60
tttatcgccc cactgccctt tcagaacact cccgtggtcg aaaccatgca gtatggcgca    120
ttattaggtg gtaagcgcct gcgacctttc ctggtttatg ccaccggtca tatgttcggc    180
gttagcacaa acacgctgga cgcacccgct gccgccgttg agtgtatcca cgcttactca    240
ttaattcatg atgatttacc ggcaatggat gatgacgatc tgcgtcgcgg tttgccaacc    300
tgccatgtga agtttggcga agcaaacgcg attctcgctg gcgacgcttt acaaacgctg    360
gcgttctcga ttttaagcga tgccgatatg ccggaagtgt cggaccgcga cagaatttcg    420
atgatttctg aactggcgag cgccagtggt attgccggaa tgtgcggtgg tcaggcatta    480
gatttagacg cggaaggcaa acacgtacct ctggacgcgc ttgagcgtat tcatcgtcat    540
aaaaccggcg cattgattcg cgccgccgtt cgccttggtg cattaagcgc cggagataaa    600
ggacgtcgtg ctctgccggt actcgacaag tatgcagaga gcatcggcct tgccttccag    660
gttcaggatg acatcctgga tgtggtggga gatactgcaa cgttgggaaa acgccagggt    720
gccgaccagc aacttggtaa agtaccctac cctgcacttc tgggtcttga gcaagcccgg    780
aagaaagccc gggatctgat cgacgatgcc cgtcagtcgc tgaaacaact ggctgaacag    840
tcactcgata cctcggcact ggaagcgcta gcggactaca tcatccagcg taataaataa    900
```

<210> SEQ ID NO 12
<211> LENGTH: 5051
<212> TYPE: DNA
<213> ORGANISM: Artificial Sequence
<220> FEATURE:
<223> OTHER INFORMATION: Description of Artificial Sequence: Synthetic
      "MBI" operon nucleotide sequence

<400> SEQUENCE: 12

```
gcgcaacgca attaatgtga gttagctcac tcattaggca ccccaggctt tacactttat     60
gcttccggct cgtatgttgt gtggaattgt gagcggataa caatttcaca caggaaacag    120
ctatgaccat gattacgcca agcgcgcaat taaccctcac taaagggaac aaaagctggg    180 tacccgggccc ccctcgagg tcgacggtat cgataagctt gatatcgaat tcctgcagta    240
ggaggaatta accatgtcat taccgttctt aacttctgca ccgggaaagg ttattatttt    300
tggtgaacac tctgctgtgt acaacaagcc tgccgtcgct gctagtgtgt ctgcgttgag    360
aacctacctg ctaataagcg agtcatctgc accagatact attgaattgg acttcccgga    420
cattagcttt aatcataagt ggtccatcaa tgatttcaat gccatcaccg aggatcaagt    480
aaactcccaa aaaattggcca aggctcaaca agccaccgat ggcttgtctc aggaactcgt    540 tagtctttg gatcgttgt tagctcaact atccgaatcc ttccactacc atgcagcgtt    600
ttgtttcctg tatatgtttg tttgcctatg cccccatgcc aagaatatta gttttctttt    660
```

```
aaagtctact ttacccatcg gtgctgggtt gggctcaagc gcctctattt ctgtatcact    720
ggccttagct atggcctact tgggggggtt aataggatct aatgacttgg aaaagctgtc    780
agaaaacgat aagcatatag tgaatcaatg ggccttcata ggtgaaaagt gtattcacgg    840
taccccttca ggaatagata acgctgtggc cacttatggt aatgccctgc tatttgaaaa    900
agactcacat aatggaacaa taaacacaaa caattttaag ttcttagatg atttcccagc    960
cattccaatg atcctaacct atactagaat tccaaggtct acaaaagatc ttgttgctcg   1020
cgttcgtgtg ttggtcaccg agaaatttcc tgaagttatg aagccaattc tagatgccat   1080
gggtgaatgt gccctacaag gcttagagat catgactaag ttaagtaaat gtaaaggcac   1140
cgatgacgag gctgtagaaa ctaataatga actgtatgaa caactattgg aattgataag   1200
aataaatcat ggactgcttg tctcaatcgg tgtttctcat cctggattag aacttattaa   1260
aaatctgagc gatgatttga gaattggctc cacaaaactt accggtgctg gtggcggcgg   1320
ttgctctttg actttgttac gaagagacat tactcaagag caaattgaca gcttcaaaaa   1380
gaaattgcaa gatgatttta gttacgagac atttgaaaca gacttgggtg ggactggctg   1440
ctgtttgtta agcgcaaaaa atttgaataa agatcttaaa atcaaatccc tagtattcca   1500
attatttgaa aataaaacta ccacaaagca acaaattgac gatctattat tgccaggaaa   1560
cacgaattta ccatggactt cataggaggc agatcaaatg tcagagttga gagccttcag   1620
tgccccaggg aaagcgttac tagctggtgg atatttagtt ttagatacaa aatatgaagc   1680
atttgtagtc ggattatcgg caagaatgca tgctgtagcc catccttacg gttcattgca   1740
agggtctgat aagtttgaag tgcgtgtgaa aagtaaacaa tttaaagatg gggagtggct   1800
gtaccatata agtcctaaaa gtggcttcat tcctgtttcg ataggcggat ctaagaaccc   1860
tttcattgaa aaagttatcg ctaacgtatt tagctacttt aaacctaaca tggacgacta   1920
ctgcaataga aacttgttcg ttattgatat tttctctgat gatgcctacc attctcagga   1980
ggatagcgtt accgaacatc gtggcaacag aagattgagt tttcattcgc acagaattga   2040
agaagttccc aaaacagggc tgggctcctc ggcaggttta gtcacagttt taactacagc   2100
tttggcctcc ttttttgtat cggacctgga aaataatgta gacaaatata gagaagttat   2160
tcataattta gcacaagttg ctcattgtca agctcagggt aaaattggaa gcgggtttga   2220
tgtagcggcg gcagcatatg gatctatcag atatagaaga ttcccacccg cattaatctc   2280
taatttgcca gatattggaa gtgctactta cggcagtaaa ctggcgcatt tggttgatga   2340
agaagactgg aatattacga ttaaaagtaa ccatttacct tcgggattaa ctttatggat   2400
gggcgatatt aagaatggtt cagaaacagt aaaactggtc cagaaggtaa aaaattggta   2460
tgattcgcat atgccagaaa gcttgaaaat atatacagaa ctcgatcatg caaattctag   2520
atttatggat ggactatcta aactagatcg cttacgcgag actcatgacg attacagcga   2580
tcagatattt gagtctcttg agaggaatga ctgtacctgt caaaagtatc ctgaaatcac   2640
agaagttaga gatgcagttg ccacaattag acgttccttt agaaaaataa ctaaagaatc   2700
tggtgccgat atcgaacctc ccgtacaaac tagcttattg gatgattgcc agaccttaaa   2760
aggagttctt acttgcttaa tacctggtgc tggtggttat gacgccattg cagtgattac   2820
taagcaagat gttgatctta gggctcaaac cgctaatgac aaaagatttt ctaaggttca   2880
atggctggat gtaactcagg ctgactgggg tgttaggaaa gaaaaagatc cggaaactta   2940
tcttgataaa taggaggtaa tactcatgac cgtttcacaca gcatccgtta ccgcacccgt   3000
caacatcgca acccttaagt attgggggaa aagggacacg aagttgaatc tgcccaccaa   3060
```

```
ttcgtccata tcagtgactt tatcgcaaga tgacctcaga acgttgacct ctgcggctac   3120
tgcacctgag tttgaacgcg acactttgtg gttaaatgga gaaccacaca gcatcgacaa   3180
tgaaagaact caaaattgtc tgcgcgacct acgccaatta agaaaggaaa tggaatcgaa   3240
ggacgcctca ttgcccacat tatctcaatg gaaactccac attgtctccg aaaataactt   3300
tcctacagca gctggtttag cttcctccgc tgctggcttt gctgcattgg tctctgcaat   3360
tgctaagtta taccaattac cacagtcaac ttcagaaata tctagaatag caagaaaggg   3420
gtctggttca gcttgtagat cgttgtttgg cggatacgtg gcctgggaaa tgggaaaagc   3480
tgaagatggt catgattcca tggcagtaca aatcgcagac agctctgact ggcctcagat   3540
gaaagcttgt gtcctagttg tcagcgatat taaaaaggat gtgagttcca ctcagggtat   3600
gcaattgacc gtggcaacct ccgaactatt taaagaaaga attgaacatg tcgtaccaaa   3660
gagatttgaa gtcatgcgta aagccattgt tgaaaaagat ttcgccacct ttgcaaagga   3720
aacaatgatg gattccaact ctttccatgc cacatgtttg gactctttcc ctccaatatt   3780
ctacatgaat gacacttcca agcgtatcat cagttggtgc cacaccatta atcagtttta   3840
cggagaaaca atcgttgcat acacgtttga tgcaggtcca aatgctgtgt tgtactactt   3900
agctgaaaat gagtcgaaac tctttgcatt tatctataaa ttgtttggct ctgttcctgg   3960
atgggacaag aaatttacta ctgagcagct tgaggctttc aaccatcaat ttgaatcatc   4020
taactttact gcacgtgaat tggatcttga gttgcaaaag gatgttgcca gagtgatttt   4080
aactcaagtc ggttcaggcc cacaagaaac aaacgaatct ttgattgacg caaagactgg   4140
tctaccaaag gaataactgc agcccgggag gaggattact atatgcaaac ggaacacgtc   4200
attttattga atgcacaggg agttcccacg ggtacgctgg aaaagtatgc cgcacacacg   4260
gcagacaccc gcttacatct cgcgttctcc agttggctgt taatgccaa aggacaatta   4320 ttagttaccc gccgcgcact gagcaaaaaa gcatggcctg gcgtgtggac taactcggtt   4380
tgtgggcacc cacaactggg agaaagcaac gaagacgcag tgatccgccg ttgccgttat   4440
gagcttggcg tggaaattac gcctcctgaa tctatctatc ctgactttcg ctaccgcgcc   4500
accgatccga gtggcattgt ggaaaatgaa gtgtgtccgg tatttgccgc acgcaccact   4560
agtgcgttac agatcaatga tgatgaagtg atggattatc aatggtgtga tttagcagat   4620
gtattacacg gtattgatgc cacgccgtgg gcgttcagtc cgtggatggt gatgcaggcg   4680
acaaatcgcg aagccagaaa acgattatct gcatttaccc agcttaaaata acccggggga   4740 tccactagtt ctagagcggc cgccaccgcg gtggagctcc aattcgccct atagtgagtc   4800
gtattacgcg cgctcactgg ccgtcgtttt acaacgtcgt gactgggaaa accctggcgt   4860
tacccaactt aatcgccttg cagcacatcc cctttcgcc agctggcgta atagcgaaga   4920
ggcccgcacc gatcgccctt cccaacagtt gcgcagcctg aatggcgaat ggaaattgta   4980
agcgttaata ttttgttaaa attcgcgtta aattttgtt aaatcagctc attttttaac   5040
caataggccg a                                                        5051
```

<210> SEQ ID NO 13
<211> LENGTH: 5963
<212> TYPE: DNA
<213> ORGANISM: Artificial Sequence
<220> FEATURE:
<223> OTHER INFORMATION: Description of Artificial Sequence: Synthetic
      "MBIS" operon nucleotide sequence

<400> SEQUENCE: 13

```
gcgcaacgca attaatgtga gttagctcac tcattaggca ccccaggctt tacactttat    60
gcttccggct cgtatgttgt gtggaattgt gagcggataa caatttcaca caggaaacag   120
ctatgaccat gattacgcca agcgcgcaat taaccctcac taaagggaac aaaagctggg   180
tacccggccc ccctcgagg tcgacggtat cgataagctt gatatcgaat tcctgcagta   240
ggaggaatta accatgtcat taccgttctt aacttctgca ccgggaaagg ttattatttt   300
tggtgaacac tctgctgtgt acaacaagcc tgccgtcgct gctagtgtgt ctgcgttgag   360
aacctacctg ctaataagcg agtcatctgc accagatact attgaattgg acttcccgga   420
cattagcttt aatcataagt ggtccatcaa tgatttcaat gccatcaccg aggatcaagt   480
aaactcccaa aaattggcca aggctcaaca agccaccgat ggcttgtctc aggaactcgt   540
tagtcttttg gatccgttgt tagctcaact atccgaatcc ttccactacc atgcagcgtt   600
ttgtttcctg tatatgtttg tttgcctatg cccccatgcc aagaatatta agttttcttt   660
aaagtctact ttacccatcg gtgctgggtt gggctcaagc gcctctattt ctgtatcact   720
ggccttagct atggcctact tgggggggtt aataggatct aatgacttgg aaaagctgtc   780
agaaaacgat aagcatatag tgaatcaatg ggccttcata ggtgaaaagt gtattcacgg   840
taccccttca ggaatagata cgctgtggc cacttatggt aatgccctgc tatttgaaaa   900
agactcacat aatggaacaa taaacacaaa caattttaag ttcttagatg atttcccagc   960
cattccaatg atcctaacct atactagaat tccaaggtct acaaaagatc ttgttgctcg  1020
cgttcgtgtg ttggtcaccg agaaatttcc tgaagttatg aagccaattc tagatgccat  1080
gggtgaatgt gccctacaag gcttagagat catgactaag ttaagtaaat gtaaaggcac  1140
cgatgacgag gctgtagaaa ctaataatga actgtatgaa caactattgg aattgataag  1200
aataaatcat ggactgcttg tctcaatcgg tgtttctcat cctggattag aacttattaa  1260
aaatctgagc gatgatttga gaattggctc cacaaaactt accggtgctg gtggcggcgg  1320
ttgctctttg actttgttac gaagagacat tactcaagag caaattgaca gcttcaaaaa  1380
gaaattgcaa gatgatttta gttacgagac atttgaaaca gacttgggtg ggactggctg  1440
ctgtttgtta agcgcaaaaa atttgaataa agatcttaaa atcaaatccc tagtattcca  1500
attatttgaa aataaaacta ccacaaagca acaaattgac gatctattat tgccaggaaa  1560
cacgaattta ccatggactt cataggaggc agatcaaatg tcagagttga gagccttcag  1620
tgccccaggg aaagcgttac tagctggtgg atatttagtt ttagatacaa aatatgaagc  1680
atttgtagtc ggattatcgg caagaatgca tgctgtagcc catccttacg gttcattgca  1740
agggtctgat aagtttgaag tgcgtgtgaa aagtaaacaa tttaaagatg gggagtggct  1800
gtaccatata agtcctaaaa gtggcttcat tcctgtttcg ataggcggat ctaagaaccc  1860
tttcattgaa aaagttatcg ctaacgtatt tagctacttt aaacctaaca tggacgacta  1920
ctgcaataga aacttgttcg ttattgatat tttctctgat gatgcctacc attctcagga  1980
ggatagcgtt accgaacatc gtggcaacag aagattgagt tttcattcgc acagaattga  2040
agaagttccc aaaacagggc tgggctcctc ggcaggttta gtcacagttt taactacagc  2100
tttggcctcc ttttttgtat cggacctgga aaataatgta gacaaatata gagaagttat  2160
tcataattta gcacaagttg ctcattgtca agctcagggt aaaattggaa gcgggtttga  2220
tgtagcggcg gcagcatatg gatctatcag atatagaaga ttcccacccg cattaatctc  2280
taatttgcca gatattggaa gtgctactta cggcagtaaa ctggcgcatt tggttgatga  2340
agaagactgg aatattacga ttaaaagtaa ccatttacct tcgggattaa ctttatggat  2400
```

```
gggcgatatt aagaatggtt cagaaacagt aaaactggtc cagaaggtaa aaaattggta    2460
tgattcgcat atgccagaaa gcttgaaaat atatacagaa ctcgatcatg caaattctag    2520
atttatggat ggactatcta aactagatcg cttacacgag actcatgacg attacagcga    2580
tcagatattt gagtctcttg agaggaatga ctgtacctgt caaaagtatc ctgaaatcac    2640
agaagttaga gatgcagttg ccacaattag acgttccttt agaaaaataa ctaaagaatc    2700
tggtgccgat atcgaacctc ccgtacaaac tagcttattg gatgattgcc agaccttaaa    2760
aggagttctt acttgcttaa tacctggtgc tggtggttat gacgccattg cagtgattac    2820
taagcaagat gttgatctta gggctcaaac cgctaatgac aaaagatttt ctaaggttca    2880
atggctggat gtaactcagg ctgactgggg tgttaggaaa gaaaaagatc cggaaactta    2940
tcttgataaa taggaggtaa tactcatgac cgtttacaca gcatccgtta ccgcacccgt    3000
caacatcgca acccttaagt attggggaa aagggacacg aagttgaatc tgcccaccaa    3060
ttcgtccata tcagtgactt tatcgcaaga tgacctcaga acgttgacct ctgcggctac    3120
tgcacctgag tttgaacgcg acactttgtg gttaaatgga gaaccacaca gcatcgacaa    3180
tgaaagaact caaaattgtc tgcgcgacct acgccaatta agaaaggaaa tggaatcgaa    3240
ggacgcctca ttgcccacat tatctcaatg gaaactccac attgtctccg aaaataactt    3300
tcctacagca gctggtttag cttcctccgc tgctggcttt gctgcattgg tctctgcaat    3360
tgctaagtta taccaattac cacagtcaac ttcagaaata tctagaatag caagaaaggg    3420
gtctggttca gcttgtagat cgttgtttgg cggatacgtg gcctgggaaa tgggaaaagc    3480
tgaagatggt catgattcca tggcagtaca aatcgcagac agctctgact ggcctcagat    3540
gaaagcttgt gtcctagttg tcagcgatat taaaaaggat gtgagttcca ctcagggtat    3600
gcaattgacc gtggcaacct ccgaactatt taagaaaga attgaacatg tcgtaccaaa    3660
gagatttgaa gtcatgcgta aagccattgt tgaaaaagat ttcgccacct ttgcaaagga    3720
aacaatgatg gattccaact cttccatgc acatgtttg gactctttcc ctccaatatt    3780
ctacatgaat gacacttcca agcgtatcat cagttggtgc cacaccatta atcagtttta    3840
cggagaaaca atcgttgcat acacgtttga tgcaggtcca aatgctgtgt tgtactactt    3900
agctgaaaat gagtcgaaac tctttgcatt tatctataaa ttgtttggct ctgttcctgg    3960
atgggacaag aaatttacta ctgagcagct tgaggctttc aaccatcaat ttgaatcatc    4020
taactttact gcacgtgaat tggatcttga gttgcaaaag gatgttgcca gagtgatttt    4080
aactcaagtc ggttcaggcc cacaagaaac aaacgaatct ttgattgacg caaagactgg    4140
tctaccaaag gaataactgc agcccgggag gaggattact atatgcaaac ggaacacgtc    4200
attttattga atgcacaggg agttcccacg ggtacgctgg aaaagtatgc cgcacacacg    4260
gcagacaccc gcttacatct cgcgttctcc agttggctgt taatgccaa aggacaatta    4320 ttagttaccc gccgcgcact gagcaaaaaa gcatggcctg gcgtgtggac taactcggtt    4380
tgtgggcacc cacaactggg agaaagcaac gaagacgcag tgatccgccg ttgccgttat    4440
gagcttggcg tggaaattac gcctcctgaa tctatctatc ctgactttcg ctaccgcgcc    4500
accgatccga gtggcattgt ggaaaatgaa gtgtgtccgg tatttgccgc acgcaccact    4560
agtgcgttac agatcaatga tgatgaagtg atggattatc aatggtgtga tttagcagat    4620
gtattacacg gtattgatgc cacgccgtgg gcgttcagtc cgtggatggt gatgcaggcg    4680
acaaatcgcg aagccagaaa acgattatct gcatttaccc agcttaaaata acccggggga    4740 tccactagtt ctagagcggc cgccaccgcg gaggaggaat gagtaatgga ctttccgcag    4800
```

```
caactcgaag cctgcgttaa gcaggccaac caggcgctga gccgttttat cgccccactg    4860 cccttcaga  acactcccgt ggtcgaaacc atgcagtatg gcgcattatt aggtggtaag    4920
cgcctgcgac ctttcctggt ttatgccacc ggtcatatgt tcggcgttag cacaaacacg    4980
ctggacgcac ccgctgccgc cgttgagtgt atccacgctt actcattaat tcatgatgat    5040
ttaccggcaa tggatgatga cgatctgcgt cgcggtttgc caacctgcca tgtgaagttt    5100
ggcgaagcaa acgcgattct cgctggcgac gctttacaaa cgctggcgtt ctcgattta    5160 agcgatgccg atatgccgga agtgtcggac cgcgacagaa tttcgatgat ttctgaactg    5220
gcgagcgcca gtggtattgc cggaatgtgc ggtggtcagg cattagattt agacgcggaa    5280
ggcaaacacg tacctctgga cgcgcttgag cgtattcatc gtcataaaac cggcgcattg    5340
attcgcgccg ccgttcgcct tggtgcatta agcgccggag ataaaggacg tcgtgctctg    5400
ccggtactcg acaagtatgc agagagcatc ggccttgcct tccaggttca ggatgacatc    5460
ctggatgtgg tgggagatac tgcaacgttg ggaaaacgcc agggtgccga ccagcaactt    5520
ggtaaaagta cctaccctgc acttctgggt cttgagcaag cccggaagaa agcccgggat    5580
ctgatcgacg atgcccgtca gtcgctgaaa caactggctg aacagtcact cgatacctcg    5640
gcactggaag cgctagcgga ctacatcatc cagcgtaata aataagagct ccaattcgcc    5700
ctatagtgag tcgtattacg cgcgctcact ggccgtcgtt ttacaacgtc gtgactggga    5760
aaaccctggc gttacccaac ttaatcgcct tgcagcacat ccccctttcg ccagctggcg    5820
taatagcgaa gaggcccgca ccgatcgccc ttcccaacag ttgcgcagcc tgaatggcga    5880
atggaaattg taagcgttaa tattttgtta aaattcgcgt taaattttg ttaaatcagc    5940 tcattttta  accaataggc cga                                            5963
```

HOST CELLS FOR PRODUCTION OF ISOPRENOID COMPOUNDS

CROSS-REFERENCE

This application is a continuation of U.S. patent application Ser. No. 12/576,068, filed Oct. 8, 2009 now U.S. Pat. No. 7,915,026, which is a continuation of U.S. patent application Ser. No. 11/610,686, filed Dec. 14, 2006, now U.S. Pat. No. 7,736,882. U.S. patent application Ser. No. 11/610,686 is a divisional application of U.S. patent application Ser. No. 10/006,909, filed Dec. 6, 2001, now U.S. Pat. No. 7,172,886. Each of the aforementioned applications is incorporated herein by reference in its entirety.

TECHNICAL FIELD

The present invention relates to the biosynthesis of isopentenyl pyrophosphate (IPP) and isoprenoids derived therefrom. More particularly, the invention relates to methods for biosynthesizing isopentenyl pyrophosphate, and to nucleic acid sequences, enzymes, expression vectors, and transformed host cells for carrying out the methods.

BACKGROUND

Isoprenoids are compounds derived from the five-carbon molecule, isopentenyl pyrophosphate. Investigators have identified over 29,000 individual isoprenoid compounds, with new ones continuously being discovered. Isoprenoids are often isolated from natural products, such as plants and microorganisms, which use isopentenyl pyrophosphate as a basic building block to form relatively complex structures. Vital to living organisms, isoprenoids serve to maintain cellular fluidity and electron transport, as well as function as natural pesticides, to name just a few of their roles in vivo. Furthermore, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Conventional means for obtaining isoprenoids include extraction from biological materials (e.g., plants, microbes, and animals) and partial or total organic synthesis in the laboratory. Such means, however, have generally proven to be unsatisfactory. For example, organic synthesis is usually complex since several steps are required to obtain the desired product. Furthermore, these steps often involve the use of toxic solvents, which require special handling and disposal. Extraction of isoprenoids from biological materials may also require toxic solvents. In addition, extraction and purification methods usually provide a low yield of the desired isoprenoid, as biological materials typically contain only small quantities of these compounds. Unfortunately, the difficulty involved in obtaining relatively large amounts of isoprenoids has limited their practical use. In fact, the lack of readily available methods by which to obtain certain isoprenoids has slowed down the progression of drug candidates through clinical trials. Furthermore, once an isoprenoid drug candidate has passed the usual regulatory scrutiny, the actual synthesis of the isoprenoid drug may not lend itself to a commercial scale.

As a solution to such problems, researchers have looked to biosynthetic production of isoprenoids. Some success has been obtained in the identification and cloning of the genes involved in isoprenoid biosynthesis. For example, U.S. Pat. No. 6,291,745 to Meyer et al. describes the production of limonene and other metabolites in plants. Although many of the genes involved in isoprenoid biosynthesis may be expressed in functional form in *Escherichia coli* and other microorganisms, yields remain relatively low as a result of minimal amounts of precursors, namely isopentenyl pyrophosphate.

In an effort to address the lack of isopentenyl pyrophosphate, some investigators have attempted to increase isopentenyl pyrophosphate production. Croteau et al. describe in U.S. Pat. No. 6,190,895 the nucleic acid sequences that code for the expression of 1-deoxyxylulose-5-phosphate synthase, an enzyme used in one biological pathway for the synthesis of isopentenyl pyrophosphate. Low yields of isopentenyl pyrophosphate remain, however, since several more enzymes are needed to catalyze other steps in this isopentenyl pyrophosphate biosynthetic pathway. Further, the reference does not address an alternative pathway for isopentenyl pyrophosphate biosynthesis, namely the mevalonate pathway.

Thus, the current invention is directed toward solving these and other disadvantages in the art by increasing the typically low yields associated with conventional synthesis of isopentenyl pyrophosphate and isoprenoids. Specifically, the current invention is directed toward identification of new methods for the synthesis of isopentenyl pyrophosphate, as isopentenyl pyrophosphate represents the universal precursor to isoprenoid synthesis.

SUMMARY OF THE INVENTION

Accordingly, it is an object of the present invention to overcome the above-mentioned disadvantages of the prior art by providing a method for synthesizing isopentenyl pyrophosphate in a host microorganism, comprising the step of introducing into the host microorganism a plurality of heterologous nucleic acid sequences, each coding for a different enzyme in the mevalonate pathway for producing isopentenyl pyrophosphate.

It is another object of the invention to provide such a method wherein the plurality of heterologous nucleic acid sequences is contained in at least one extrachromosomal expression vector.

It is still another object of the invention to provide such a method wherein the isopentenyl pyrophosphate is further synthesized into an isoprenoid.

It is yet another object of the invention to provide such a method wherein the isoprenoid is selected from the group consisting of a monoterpene, sesquiterpene, diterpene, sesterterpene, triterpene, tetraterpene, and a steroid.

It is a further object of the invention to provide such a method wherein the plurality of heterologous nucleic acid sequences further comprises a DNA fragment coding for an enzyme capable of converting isopentenyl pyrophosphate to dimethylallyl pyrophosphate.

It is still a further object of the invention to provide a method wherein the host microorganism is a prokaryote.

It is an additional object of the invention to provide a method wherein the prokaryote is *Escherichia coli*.

Is it still another object of the invention to provide a method for synthesizing isopentenyl pyrophosphate in a host microorganism, wherein the method comprises introducing into the host microorganism an intermediate in the mevalonate pathway and at least one heterologous nucleic acid sequence, each said sequence coding for an enzyme in the mevalonate pathway necessary for converting the intermediate into isopentenyl pyrophosphate.

It is still a further object of the invention to provide DNA fragments, expression vectors, and host cells for carrying out the methods described herein.

Additional objects, advantages, and novel features of the invention will be set forth in part in the description that follows, and in part will become apparent to those skilled in the art upon examination of the following, or may be learned through routine experimentation upon practice of the invention.

In one embodiment, the invention provides a method for synthesizing isopentenyl pyrophosphate in a host microorganism. The method comprises introducing into a host microorganism a plurality of heterologous nucleic acid sequences, each coding for a different enzyme in the mevalonate pathway for producing isopentenyl pyrophosphate. As will be appreciated by those skilled in the art, the mevalonate pathway involves six enzymes. The pathway starts from acetyl-CoA, proceeds through the intermediate mevalonic acid, and results in isopentenyl pyrophosphate. Of course, additional nucleotide sequences coding for other genes may be introduced as well. In particular, nucleotide sequences coding for enzymes necessary in the production of specific isoprenoids may be introduced into the host microorganism, along with those coding for enzymes in the mevalonate pathway. Preferably, at least one extrachromosomal expression vector will be used to introduce the desired nucleic acid sequence(s), although more than one (e.g., two) different expression vectors may be used. In addition, the desired nucleic acid sequence(s) may be incorporated into the host microorganism's chromosomal material.

In another embodiment, the invention provides a method for synthesizing isopentenyl pyrophosphate in a host microorganism by introducing into the host microorganism an intermediate of the mevalonate pathway and one or more heterologous nucleic acid sequences. The introduced sequence or sequences each code for an enzyme in the mevalonate pathway necessary for converting the intermediate into isopentenyl pyrophosphate. Thus, for example, if mevalonate is the introduced intermediate, the method requires introduction of nucleic acid sequences that code for the enzymes necessary to convert mevalonate into isopentenyl pyrophosphate, for example, the introduction of nucleic acid sequences coding for an enzyme that phosphorylates mevalonate to mevalonate 5-phosphate, an enzyme that converts mevalonate 5-phosphate to mevalonate 5-pyrophosphate, and an enzyme that converts mevalonate 5-pyrophosphate to isopentenyl pyrophosphate. Of course, other intermediates in the mevalonate pathway, along with the necessary nucleic acid sequences, may be introduced as well.

Although any host microorganism, e.g., a prokaryote or eukaryote, may be employed, it is preferred that a prokaryote such as *Escherichia coli* be used. Preferably, the host organism does not synthesize isopentenyl pyrophosphate through the mevalonate pathway, but rather through the deoxyxylulose-5 phosphate (DXP) pathway. In this way, side reactions involving the intermediates of the mevalonate pathway are minimized, thereby enhancing the yield and efficiency of the present methods.

In another embodiment of the invention, DNA fragments, each coding for an enzyme in the mevalonate pathway, are provided in one or more expression vectors. Thus, for the mevalonate pathway, the DNA fragments include those that code for enzymes capable of: (a) condensing two molecules of acetyl-CoA to acetoacetyl-CoA, preferably the nucleotide sequence of SEQ ID NO 1; (b) condensing acetoacetyl-CoA with acetyl-CoA to form HMG-CoA, preferably the nucleotide sequence of SEQ ID NO 2; (c) converting HMG-CoA to mevalonate, preferably the nucleotide sequence of SEQ ID NO 3; (d) phosphorylating mevalonate to mevalonate 5-phosphate, preferably the nucleotide sequence of SEQ ID NO 4; (e) converting mevalonate 5-phosphate to mevalonate 5-pyrophosphate, preferably the nucleotide sequence of SEQ ID NO 5; and (f) converting mevalonate 5-pyrophosphate to isopentenyl pyrophosphate, preferably the nucleotide sequence of SEQ ID NO 6.

In yet another embodiment, the invention provides expression vectors comprising the DNA fragments described above and elsewhere in the application, as well as host cells transformed with such expression vectors. The DNA fragments, expression vectors, and host cells transformed with the same expression vectors are useful in the present methods for synthesizing isopentenyl pyrophosphate.

BRIEF DESCRIPTION OF THE DRAWINGS

For reference.

DETAILED DESCRIPTION OF THE INVENTION

Figure 1A:
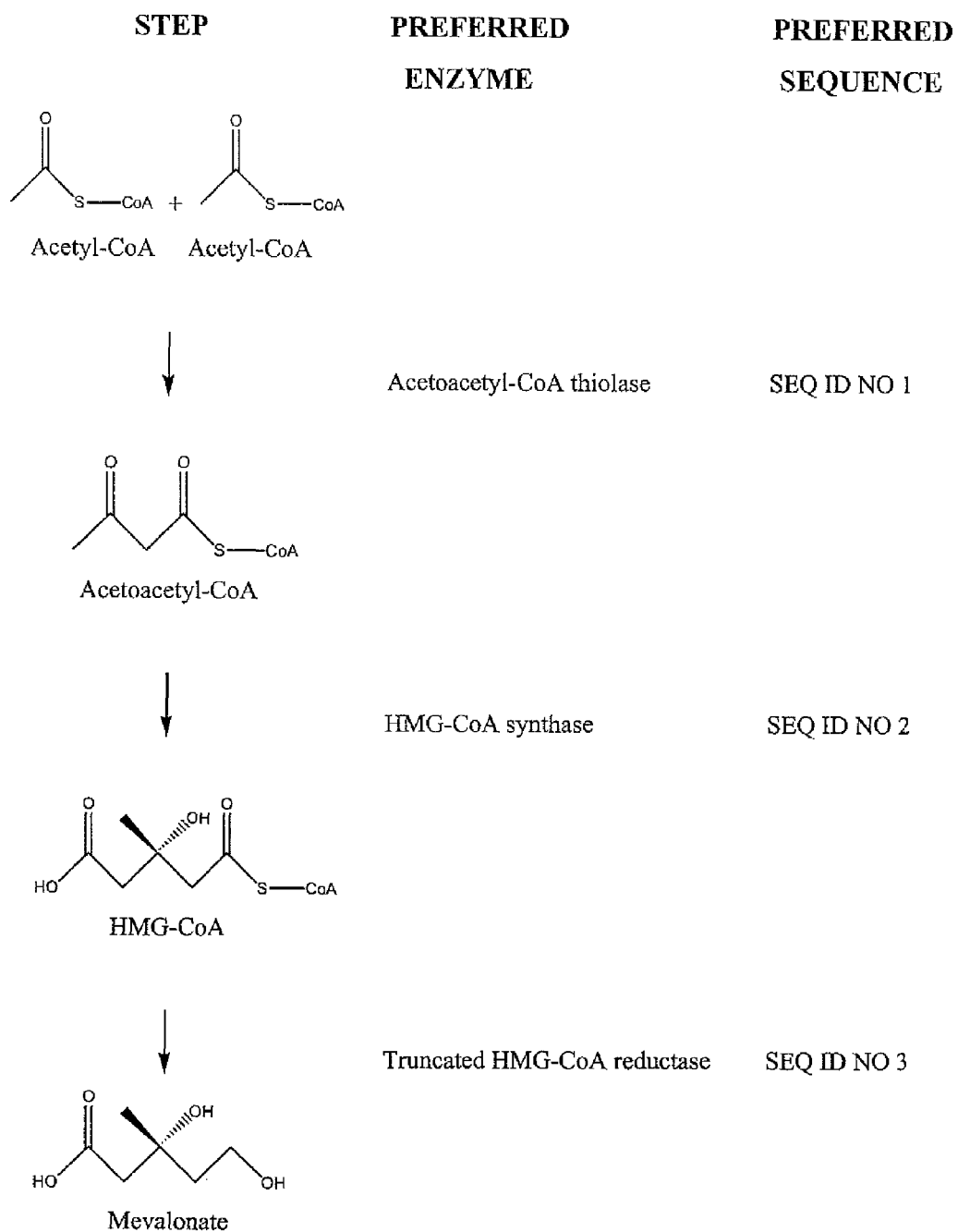
FIGS. 1A and 1B schematically illustrate the mevalonate pathway of isopentenyl pyrophosphate synthesis, along with enzymes involved and nucleic acid sequences coding for such enzymes.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "microorganism" includes a single microorganism as well as a plurality of microorganisms; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host microorganism" and "cell" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus. A preferred prokaryotic cell is *Escherichia coli*. Preferred eukaryotic cells are those derived from fungal, insect, or mammalian cell lines.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochemistry* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

In a first embodiment, the invention provides a method for synthesizing isopentenyl pyrophosphate, the fundamental building block of isoprenoids, in a host microorganism.

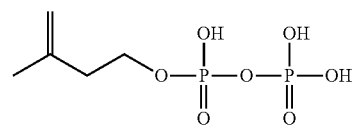

Isopentenyl pyrophosphate

Isopentenyl pyrophosphate is also known as "isopentenyl diphosphate" and is commonly abbreviated as "IPP." The method comprises introducing into the host microorganism a plurality of heterologous nucleic acid sequences each coding for a different enzyme in the mevalonate pathway for producing isopentenyl pyrophosphate. As stated previously, the mevalonate pathway for producing isopentenyl pyrophosphate in living organisms begins with acetyl-CoA and involves a mevalonate intermediate.

In another method for synthesizing isopentenyl pyrophophate, an intermediate in the mevalonate pathway is introduced into the host microorganism. Although any method for introducing the intermediate may be used, it is preferred to add the intermediate to the culture medium used to grow the host microorganism. In this way, the intermediate is transported, e.g., via passive diffusion, across the cellular membrane and into the host microorganism.

Either before or after the intermediate is introduced, nucleic acid sequence(s) are introduced that code for those enzymes of the mevalonate pathway necessary to convert the intermediate into isopentenyl pyrophosphate. As will be appreciated by one of ordinary skill in the art, the conversion from the intermediate into isopentenyl pyrophosphate may require one, two, three, or more steps. Although any of the intermediates, i.e., acetyl Co-A, acetoacetyl-CoA, HMG-CoA, mevalonate, mevalonate 5-phosphate, and mevalonate 5-diphosphate, may be used, introduction of DL-mevalonate is a particularly preferred intermediate when using this method in the production of isopentenyl pyrophosphate. Enantiomers of any of the intermediates, such as the bioactive enantiomer D-mevalonate, may be used as well.

Figure 1B:
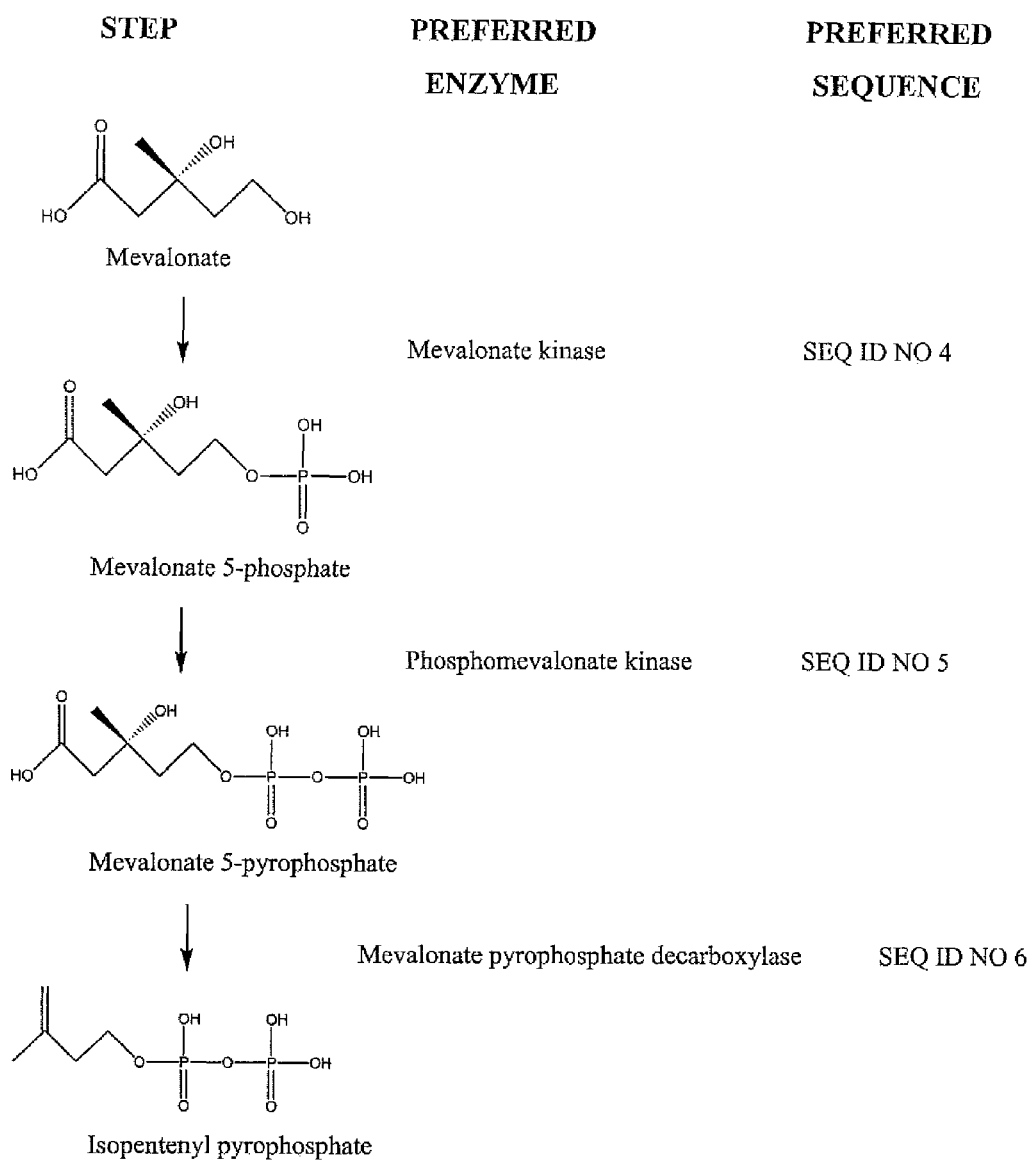

As shown in the schematic of FIGS. 1A and 1B, the mevalonate pathway comprises six steps and involves six intermediates. Initially, two molecules of acetyl-coenzyme A (more commonly referred to as "acetyl-CoA") are combined. Acetyl-CoA is produced naturally by the host microorganism when it is in the presence of a suitable carbon source. For example, eukaryotic cells naturally synthesize acetyl-CoA from compounds derived from sugars and fats. An enzyme capable of condensing two molecules of acetyl-CoA to acetoacetyl-CoA is used in this first step of synthesizing isopentenyl pyrophosphate via the mevalonate pathway.

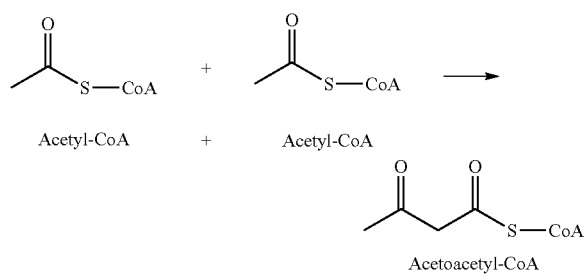

Thus, any DNA fragment coding for an enzyme capable of carrying out this step may be used in the present method. Preferably, however, the DNA fragment codes for an acetoacetyl-CoA thiolase. Genes for such thiolases are known to those of ordinary skill in the art and include, for example, the genes of acetyl-CoA thiolase from *Ralstonia eutrophus* (Peoples et al. (1989), "Poly-β-Hydroxybutyrate Biosynthesis in *Alcaligenes eutrophus* H16" and "Characterization of the Genes Encoding β-Ketothiolase and Acetoacetyl-CoA Reductase," *J. Biol. Chem.* 264 (26): 5293-15297); *Saccharomyces cerevisiae* (*S. cerevisiae*) (Hiser et al. (1994), "ERG10 From *Saccharomyces cerevisiae* Encodes Acetoacetyl-CoA Thiolase," *J. Biol. Chem.* 269 (50): 31383-31389); and *Escherichia coli*. It is particularly preferred, however, that the thiolase encoded by the nucleotide sequence of SEQ ID NO 1 be used in the present method.

The next step in the mevalonate pathway requires the condensation of acetoacetyl-CoA, formed from the preceding step, with yet another molecule of acetyl-CoA to form 3-hydroxy-3-methylglutaryl-CoA (HMG-CoA). This step is catalyzed enzymatically using an enzyme that will condense acetoacetyl-CoA with acetyl-CoA.

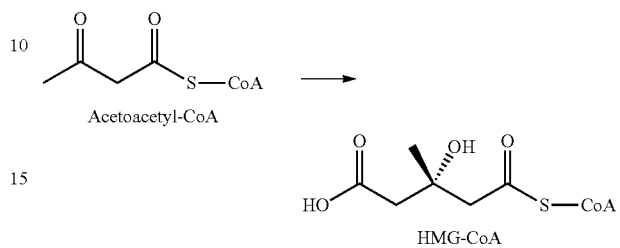

Although any DNA fragment that codes for an enzyme capable of carrying out this step may be used, it is preferred that the DNA fragment code for an HMG-CoA synthase. Known genes for HMG-CoA synthases include, without limitation, the synthases from *Blattella germanica* (Martinez-Gonzalez et al. (1993), "3-Hydroxy-3-Methylglutaryl-Coenzyme-A Synthase from *Blattella germanica*. Cloning, Expression, Developmental Pattern and Tissue Expression," *Eur. J. Biochem.* 217(2), 691-699); and *S. cerevisiae*, and thus, are preferred. A particularly preferred synthase is encoded by the nucleotide sequence of SEQ ID NO 2.

The third step converts HMG-CoA to mevalonate. As with the other steps, this conversion is enzymatically controlled.

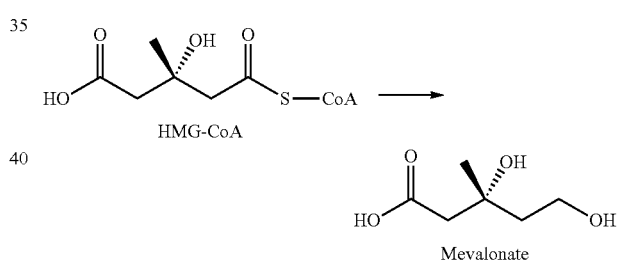

According to the present method, a DNA fragment coding for an enzyme that is capable of converting HMG-CoA into mevalonate is included in the expression vector. The HMG-CoA reductase genes from *Sulfolobus solfataricus* (Bochar (1997), "3-Hydroxy-3-Methylglutaryl-Coenzyme A Reductase of *Sulfolobus solfataricus*: DNA Sequence, Phylogeny, Expression in *Escherichia coli* of the hmgA Gene, and Purification and Kinetic Characterization of the Gene Product," *J. Bacteriol.* 179(11): 3632-3638); *Haloferax volcanii* (Bischoff et al. (1996), "3-Hydroxy-3-Methylglutaryl-Coenzyme A Reductase from *Haloferax volcanii*: Purification, Characterization, and Expression in *Escherichia coli*," *J. Bacteriol.* 178(1):19-23); and *S. cerevisiae* (Basson et al. (1988), "Structural and Functional Conservation Between Yeast and Human 3-Hydroxy-3-Methylglutaryl Coenzyme A Reductases, the Rate-Limiting Enzyme of Sterol Biosynthesis," *Mol Cell Biol.* 8(9): 3797-808) are known, and consequently preferred for the present methods. It is particularly preferred, however, that the nucleotide sequence of SEQ ID NO 3 that encodes an HMG-CoA reductase be used in the present methods.

The nucleotide sequence defined by SEQ ID NO 3 that encodes an HMG-CoA reductase is a truncated version of the *S. cerevisiae* gene coding for HMG-CoA reductase, HMG1. The protein coded for by HMG1 is an integral membrane protein located in the endoplasmic reticulum of *S. cerevisiae*; it consists of a membrane-spanning, regulatory domain in its N-terminal region (amino acids 1-552) and a catalytically active domain in its C-terminal region. (See Polakowski (1998), "Overexpression of a Cytosolic Hydroxymethylglutaryl-CoA Reductase Leads to Squalene Accumulation in Yeast," *Appl. Microbiol Biotechnol.* 49:66-71.) The nucleotide sequence defined by SEQ ID NO 3 comprises an artificial start codon, followed by nucleotides 1660-3165 of the HMG1 sequence. Therefore, the nucleotide sequence defined by SEQ ID NO 3 codes for only the catalytically active portion of *S. cervisiae* HMG-CoA reductase.

The fourth step in the mevalonate pathway involves the enzymatic phosphorylation of mevalonate to form mevalonate 5-phosphate.

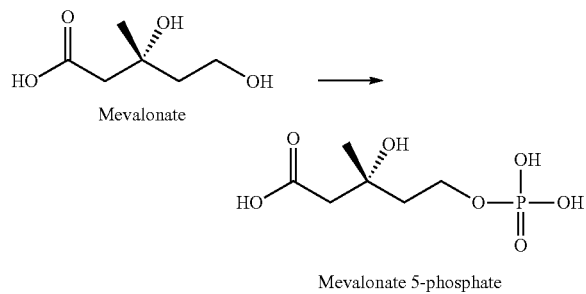

Although any DNA fragment coding for an enzyme capable of mevalonate phosphorylation may be used, it is preferred that a DNA fragment coding specifically for mevalonate kinase be used. Genes for such kinases are known to those of ordinary skill in the art and include, for example, the mevalonate kinase of *S. cerevisiae* (Oulmouden et al. (1991), "Nucleotide Sequence of the ERG12 Gene of *Saccharomyces cerevisiae* Encoding Mevalonate Kinase," Curr. Genet. 19(1): 9-14). A particularly preferred sequence that codes for this particular kinase is identified in SEQ ID NO 4.

The fifth step in the mevalonate pathway requires the addition of a second phosphate group to mevalonate 5-phosphate. An enzyme catalyzes this step.

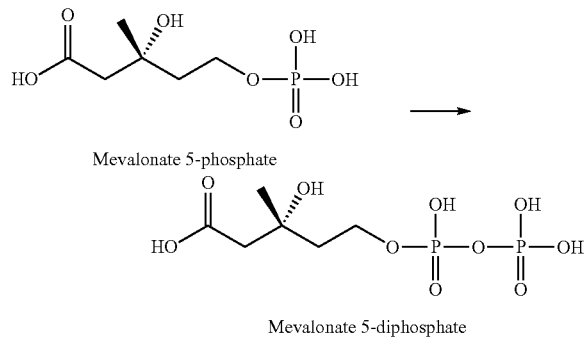

In the present method, a DNA fragment that codes for an enzyme capable of adding a second phosphate group to mevalonate 5-phosphate is used in the expression vector. Preferably, the DNA fragment codes for a phosphomevalonate kinase, such as the gene of the same name obtained from *S. cerevisiae* (Tsay et al. (1991), "Cloning and Characterization of ERG8, an Essential Gene of *Saccharomyces cerevisiae* that Encodes Phosphomevalonate Kinase," *Mol. Cell. Biol.* 11(2): 620-31). Such kinases are known to those of ordinary skill in the art and include, for example, the kinase coded by the nucleotide sequence of SEQ ID NO 5.

The sixth and final step of the mevalonate pathway is the enzymatic conversion of mevalonate 5-pyrophosphate into isopentenyl pyrophosphate.

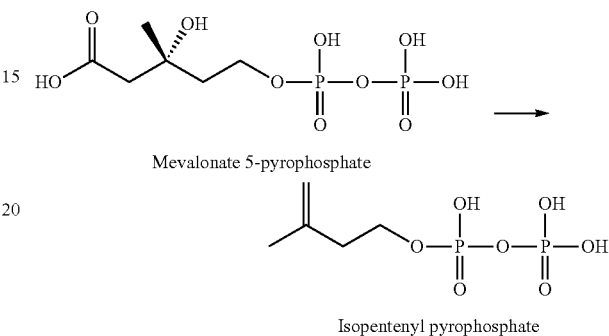

Although any DNA fragment coding for a mevalonate pyrophosphate decarboxylase may be used, it is particularly preferred that the gene from *S. cerevisiae* (Toth et al. (1996), "Molecular Cloning and Expression of the cDNAs Encoding Human and Yeast Mevalonate Pyrophosphate Decarboxylase," *J. Biol. Chem.* 271(14):7895-7898) be used. A particularly preferred DNA fragment is the nucleotide sequence of SEQ ID NO 6.

When an intermediate is introduced, the method additionally requires introduction of DNA fragments that code for enzymes responsible for catalyzing those steps of the mevalonate pathway located "downstream" from the introduced intermediate. With reference to the mevalonate pathway described above and to the biosynthetic schemes provided in FIGS. 1A and 1B, one of ordinary skill in the art can readily determine which DNA fragments and enzymatic steps are necessary when a given intermediate is introduced into the host microorganism.

The mevalonate pathway is contrasted with the mevalonate-independent (or deoxyxylulose-5-phosphate) pathway. In some organisms, isopentenyl pyrophosphate production proceeds by condensation of pyruvate and glyceraldehyde-3-phosphate, via 1-deoxyxylulose-5-phosphate (DXP) as an intermediate. (See Rohmer et al. (1993) *Biochem. J.* 295:517-524.) While some organisms have genes for only one pathway, other organisms have genes for both pathways. For a discussion of both the mevalonate and deoxyxylulose 5-phosphate pathways, reference is made to Lange et al. (2000), "Isoprenoid Biosynthesis: The Evolution of Two Ancient and Distinct Pathways Across Genomes," *Proc. Natl. Acad. Sci. USA* 97(24):13172-13177.

Any prokaryotic or eukaryotic host microorganism may be used in the present method so long as it remains viable after being transformed with a sequence of nucleic acids. Generally, although not necessarily, the host microorganism is bacterial. Examples of bacterial host microorganisms include, without limitation, those species assigned to the *Escherichia, Enterobacter, Azotobacter, Erwinia, Bacillus, Pseudomonas, Klebsielia, Proteus, Salmonella, Serratia, Shigella, Rhizobia, Vitreoscilla,* and *Paracoccus* taxonomical classes. Preferably, the host microorganism is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host microorganism's own metabolic processes and those processes involved with the mevalonate pathway.

Those of ordinary skill in the art can readily identify suitable host microorganisms. For example, cross-talk is minimized or eliminated entirely when the host microorganism relies exclusively on the "deoxyxylulose 5-phosphate" (or "DXP") pathway for synthesizing isopentenyl pyrophosphate. In such host microorganisms, the mevalonate pathway does not inherently influence (save for the additional synthesis of isopentenyl pyrophosphate) the host microorganism, since it lacks any genes that are equipped to process the proteins (i.e., enzymes) or intermediates associated with the mevalonate pathway. Such organisms relying exclusively or predominately on the deoxyxylulose 5-phosphate pathway include, for example, *Escherichia coli*. Of course, it will be recognized by those of ordinary skill in the art that the host microorganism used in the method may also conduct isopentenyl pyrophosphate synthesis via the mevalonate pathway, either exclusively or in combination with the deoxyxylulose 5-phosphate pathway.

Sequences of nucleic acids coding for the desired enzymes of the mevalonate pathway are prepared by any suitable method known to those of ordinary skill in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain; wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in D. M. Matteuci et al. (1980) *Tet. Lett.* 521:719; U.S. Pat. No. 4,500,707 to Caruthers et al.; and U.S. Pat. Nos. 5,436,327 and 5,700,637 to Southern et al.). In addition, the desired sequences may be isolated from natural sources by splitting DNA using appropriate restriction enzymes, separating the fragments using gel electrophoresis, and thereafter, recovering the desired nucleic acid sequence from the gel via techniques known to those of ordinary skill in the art, such as utilization of polymerase chain reactions. (See, for example, U.S. Pat. No. 4,683,195 to Mullis.)

Once each of the individual nucleic acid sequences necessary for carrying out the desired steps of the mevalonate pathway has been determined, each sequence must be incorporated into an expression vector. Incorporation of the individual nucleic acid sequences may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a nucleic acid sequence having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired nucleic acid sequence are often cleaved with the same restriction enzyme, thereby assuring that the ends of the expression vector and the ends of the nucleic acid sequence are complementary to each other. In addition, DNA linkers may be used to facilitate linking of nucleic acids sequences into an expression vector.

A series of individual nucleic acid sequences can also be combined by utilizing methods that are known to those having ordinary skill in the art. (See, for example, U.S. Pat. No. 4,683,195 to Minshull et al.)

For example, each of the desired nucleic acid sequences can be initially generated in a separate polymerase chain reaction (PCR). Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual nucleic acid sequences may be "spliced" together and subsequently transduced into a host microorganism simultaneously. Thus, expression of each of the plurality of nucleic acid sequences is effected.

Individual nucleic acid sequences, or "spliced" nucleic acid sequences, are then incorporated into an expression vector. The invention is not limited with respect to the process by which the nucleic acid sequence is incorporated into the expression vector. Those of ordinary skill in the art are familiar with the necessary steps for incorporating a nucleic acid sequence into an expression vector. A typical expression vector contains the desired nucleic acid sequence preceded by one or more regulatory regions, along with a ribosome binding site, e.g., a nucleotide sequence that is 3-9 nucleotides in length and located 3-11 nucleotides upstream of the initiation codon in *Escherchia coli*. See Shine et al. (1975) *Nature* 254:34 and Steitz, in *Biological Regulation and Development: Gene Expression* (ed. R. F. Goldberger), vol. 1, p. 349, 1979, Plenum Publishing, N.Y., for discussions of ribosome binding sites in *Escherichia coli*.

Regulatory regions include, for example, those regions that contain a promoter and an operator. A promoter is operably linked to the desired nucleic acid sequence, thereby initiating transcription of the nucleic acid sequence via an RNA polymerase enzyme. An operator is a sequence of nucleic acids adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example includes the tac promoter. (See deBoer et al. (1983) *Proc. Natl. Acad. Sci. U.S.A.* 80:21-25.) As will be appreciated by those of ordinary skill in the art, these and other expression vectors may be used in the present invention, and the invention is not limited in this respect.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC19; bacteriophages, such as M13 phage and λ phage; as well as mutant phages, such as λgt-λβ. Of course, such expression vectors may only be suitable for a particular host microorganism. One of ordinary skill in the art, however, can readily determine through routine experimentation whether any particular expression vector is suited for any given host microorganism. For example, the expression vector can be introduced into the host organism, which is then monitored for viability and expression of the sequences contained in the vector. In addition, reference may be made to the relevant texts and literature, which describe expression vectors and their suitability to any particular host microorganism.

The expression vectors of the invention must be introduced or transferred into the host microorganism. Such methods for transferring the expression vectors into host microorganisms are well known to those of ordinary skill in the art. For example, one method for transforming *Escherchia coli* with an expression vector involves a calcium chloride treatment wherein the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host microorganism. Also, microinjection of the nucleic acid sequence(s) provides the ability to transfect host microorganisms. Other means, such as lipid complexes, liposomes, and dendrimers, may also be employed. Those of ordinary skill in the art can transfect a host microorganism with a desired sequence using these or other methods.

For identifying a transfected host microorganism, a variety of methods are available. For example, a culture of potentially transfected host microorganisms may be separated, using a suitable dilution, into individual cells and thereafter individually grown and tested for expression of the desired nucleic acid sequence. In addition, when plasmids are used, an often-used practice involves the selection of cells based upon antimicrobial resistance that has been conferred by genes intentionally contained within the expression vector, such as the amp, gpt, neo, and hyg genes.

The host microorganism is transformed with at least one expression vector. When only a single expression vector is used (without the addition of an intermediate), the vector will contain all of the nucleic acid sequences necessary for carrying out isopentenyl pyrophosphate synthesis via the mevalonate pathway. Although such an all-encompassing expression vector may be used when an intermediate is introduced, only those nucleic acid sequence(s) necessary for converting the intermediate to isopentenyl pyrophosphate are required.

When two versions of an expression vector are used (without the addition of an intermediate), nucleic acid sequences coding for some of the six proteins (i.e., enzymes) necessary for isopentenyl synthesis via the mevalonate pathway may be contained in a first expression vector, while the remainder are contained in a second expression vector. Again, the nucleic acid sequence(s) necessary for converting an introduced intermediate into isopentenyl pyrophosphate will be contained in the expression vector(s). As will be appreciated by those of ordinary skill in the art, a number of different arrangements are possible, and the invention is not limited with respect to the particular arrangement used.

Once the host microorganism has been transformed with the expression vector, the host microorganism is allowed to grow. For microbial hosts, this process entails culturing the cells in a suitable medium. It is important that the culture medium contain an excess carbon source, such as a sugar (e.g., glucose) when an intermediate is not introduced. In this way, cellular production of acetyl-CoA, the starting material necessary for isopentenyl pyrophosphate production in the mevalonate pathway, is ensured. When added, the intermediate is present in an excess amount in the culture medium.

As the host microorganism grows and/or multiplies, expression of the proteins (i.e., enzymes) necessary for carrying out the mevalonate pathway, or for carrying out one or more steps within the pathway, is effected. Once expressed, the enzymes catalyze the steps necessary for carrying out the steps of the mevalonate pathway, i.e., converting acetyl-CoA into isopentenyl pyrophosphate. If an intermediate has been introduced, the expressed enzymes catalyze those steps necessary to convert the intermediate into isopentenyl pyrophosphate. Any means for recovering the isopentenyl pyrophosphate from the host microorganism may be used. For example, the host microorganism may be harvested and subjected to hypotonic conditions, thereby lysing the cells. The lysate may then be centrifuged and the supernatant subjected to high performance liquid chromatography (HPLC). Once the isopentenyl pyrophosphate is recovered, modification may be carried out in the laboratory to synthesize the desired isoprenoid.

If desired, the isopentenyl pyrophosphate may be left in the host microorganism for further processing into the desired isoprenoid in vivo. For example, large amounts of the isoprenoid lycopene are produced in *Escherichia coli* specially engineered with the expression vector pAC-LYC, as shown in Examples 3 and 4. Lycopene can be recovered using any art-known means, such as those discussed above with respect to recovering isopentenyl pyrophosphate. Lycopene is an antioxidant abundant in red tomatoes and may protect males from prostate cancer. (See Stahl et al. (1996) *Ach. Biochem. Biophys.* 336(1):1-9.) Of course, many other isoprenoids can be synthesized through other pathways, and the invention is not limited with respect to the particular "downstream" pathway. Thus, the present method not only provides methods for producing isopentenyl pyrophosphate, but offers methods for producing isoprenoids as well.

Optionally, when it is desired to retain isopentenyl pyrophosphate in the host microorganism for further biochemical processing, it is preferred that the heterologous nucleic acid sequences introduced into the host microorganism also include a DNA fragment coding for an enzyme capable of converting isopentenyl pyrophosphate to dimethylallyl pyrophosphate. As appreciated by those of ordinary skill in the art, a suitable isomerase will catalyze the conversion of isopentenyl pyrophosphate into dimethylallyl pyrophosphate. Such isomerases are known to those of ordinary skill and include, for example, the isopentenyl pyrophosphate isomerase (idi) coded by the nucleotide sequence of SEQ ID NO 10. Isoprenoid biosynthetic pathways require dimethylallyl pyrophosphate, and increased expression of the isomerase ensures that the conversion of isopentenyl diphosphate into dimethylallyl pyrophosphate does not represent a rate-limiting step in the overall pathway.

The present methods thus provide for the biosynthetic production of isopentenyl pyrophosphate and isoprenoids derived therefrom. As stated above, isopentenyl pyrophosphate has been available only in relatively small amounts, and the present methods provide a means for producing relatively large amounts of this important compound.

Further, the invention provides the ability to synthesize increased amounts of isoprenoids. As stated above, isoprenoids represent an important class of compounds and include, for example, food and feed supplements, flavor and odor compounds, and anticancer, antimalarial, antifungal, and antibacterial compounds. Preferred isoprenoids are those selected from the group consisting of monoterpenes, sesquiterpenes, diterpenes, sesterterpenes, triterpenes, tetraterpenes, and steroids. As a class, terpenes are classified based on the number of isoprene units comprised in the compound.

Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged terpenes.

Monoterpenes include, for example, flavors such as limonene, fragrances such as citranellol, and compounds having anticancer activity, such as geraniol. Sesquiterpenes include, without limitation: periplanone B, a cockroach hormone used to lure cockroaches into traps; artemisinin, an antimalarial drug; ginkgolide B, a platelet-activating factor antagonist; forskolin, an inhibitor of adenylate cyclase; and farnesol, a compound shown to have anticancer activity. Non-limiting examples of diterpenes include the antibacterial and antifungal compound casbene and the drug paclitaxel. Among triterpenes ($C_{30}$) and tetraterpenes ($C_{40}$) are carotenoids, which are used as antioxidants, coloring agents in food and cosmetics, and nutritional supplements (e.g., as vitamin A precursors). As pathways to these and other isoprenoids are already known, the invention can advantageously be incorporated into an overall scheme for producing relatively large amounts of a desired isoprenoid.

Conveniently, the invention also provides sequences, enzymes, expression vectors, and host cells or microorganisms for carrying out the present methods. For example, the six genes necessary for isopentenyl pyrophosphate synthesis from acetyl-CoA are conveniently provided in SEQ ID NO 7. In addition, the invention also provides sequences for the first three genes and the last three genes in SEQ ID NOs 8 and 9, respectively. These sequences can easily be included in an expression vector using techniques described herein or other techniques well known to those of ordinary skill in the art. In addition, the invention also provides host cells transformed with one or more of these expression vectors for use in carrying out the present methods.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

EXPERIMENTAL

The practice of the present invention will employ, unless otherwise indicated, conventional techniques of the biosynthetic industry and the like, which are within the skill of the art. Such techniques are explained fully in the literature.

In the following examples, efforts have been made to ensure accuracy with respect to numbers used (e.g., amounts, temperature, etc.), but some experimental error and deviation should be accounted for. Unless indicated otherwise, temperature is in degrees Celsius and pressure is at or near atmospheric pressure at sea level. All reagents, unless otherwise indicated, were obtained commercially.

Example 1

Cloning of the Mevalonate Pathway Operons

Assembly of the Mevalonate Operons

Individual genes for a mevalonate-isoprenoid pathway were assembled to form artificial complete and at least one functional operon. Cloning of the nucleic acid sequences coding for the enzymes of the mevalonate pathway was carried out and the reproduced sequences were divided into two operons. In one of the two operons, the last three genes of the biosynthetic pathway (mevalonate kinase (MK)—SEQ ID NO 4; phosphomevalonate kinase (PMK)—SEQ ID NO 5; and mevalonate pyrophosphate decarboxylase (MPD)—SEQ ID NO 6) were cloned by a polymerase chain reaction (PCR) as one operon by splicing the genes together using overlap extensions (SOEing). This operon is referred to as the mevalonate bottom (MevB) operon (SEQ ID NO 9). In the second of the two operons, the first three genes of the pathway (acetoacetyl-CoA thiolase (atoB)—SEQ ID NO 1; HMG-CoA synthase (HMGS)—SEQ ID NO 2; and a truncated version of HMG-CoA reductase (tHMGR)—SEQ ID NO 3) were cloned as a separate artificial operon using the same technique. This operon is referred to as the mevalonate top (MevT) operon (SEQ ID NO 8). The individual genes were isolated by PCR from genomic DNA of *Saccharomyces cerevisiae* and *Escherichia coli* prepared by established microbiologic protocols. (See Sambrook et al., *Molecular Cloning: a Laboratory Manual*, $3^{rd}$ ed., Cold Harbor Springs Laboratory Press.) The 100 μL PCR reactions contained 1×Pfu buffer, 1.5 mM $MgSO_4$ (Stratagene, La Jolla, Calif.), 200 μM of each dNTP (Gibco BRL™, Life Technologies, Inc., Gaithersburg, Md.), 500 μM of each primer, 100 to 500 ng of template DNA, 5% dimethyl sulfoxide (Sigma, St. Louis, Mo.), and 2.5 U of Pfu Turbo DNA polymerase (Stratagene). The reactions were carried out in a PTC-200 Peltier Thermal Cycler from MJ Research (South San Francisco, Calif.) with the following temperature cycling program: an initial heating step up to 95° C. for four minutes was followed by 30 cycles of 30 seconds of denaturing at 95° C., 30 seconds of annealing at 50° C., and 100 seconds of extension at 72° C., followed by one cycle at 72° C. for ten minutes. Once each gene of the operon was amplified from genomic DNA preparations, the operons were assembled by PCR reactions similar to the procedure described above, but using the amplified DNA of all three genes as template DNA and only the forward primer of the outermost 5' gene and the reverse primer of the outermost 3' gene. The assembled operons were isolated on 0.7% agarose gels and purified using a Qiagen gel purification kit (Valencia, Calif.) according to the manufacturer's instructions.

Cloning Mevalonate Operons into Sequencing and Expression Vectors

As expression of biochemical pathways is often suboptimal from high-copy plasmids containing strong promoters, the artificial mevalonate operon(s) were cloned in a variety of expression vectors to determine the effect of plasmid copy number and promoter strength on expression of the cloned pathway. Prior to testing for pathway expression, the assembled operons were cloned into the pCR4 TOPO vector using the Invitrogen TOPO TA cloning system (Carlsbad, Calif.) for sequencing purposes. Ligation into pCR4 TOPO vector and transformation of *Escherichia coli* TOP10 cells were carried out according to the manufacturer's instructions. The synthetic operons were excised from the sequenced pCR4 TOPO vectors using restriction enzymes and ligated into the high-copy vector pBAD24, which contains the arabinose-inducible araBAD promoter (Guzman et al. (1995) *J. Bacteriology* 177:4121-4130); pTrc99A, which contains the IPTG-inducible tac promoter (Amann et al. (1988) *Gene* 69:301-315); or into pBBR1MCS-3 (Kovach et al. (1995) *Gene* 166:175-176) or pUC19 (Yanisch-Perron et al. (1985) *Gene* 33:103-119), which contain the unregulated Lac promoters (no plasmid-encoded LacI). The MevB operon was digested with PstI and ligated using T4 DNA ligase (New England Biolabs, Inc., Beverly, Mass.) into the PstI site of the low-copy vector, pBBR1MCS-3, containing $P_{Lac}$ promoter and tetracycline resistance marker. The resulting plasmid, which encodes the enzymes responsible for the conversion of mevalonate to isopentenyl pyrophosphate, was named pBBRMevB. The MevT operon was cloned into the SalI site of pBAD24 by digesting with SalI restriction enzyme and ligating with T4 DNA ligase. The resulting plasmid, which encodes the enzymes responsible for the conversion of acetyl-CoA to mevalonate, was named pBADMevT.

Addition of Isopentenyl Pyrophosphate Isomerase to MevB Operon

The syntheses of geranyl pyrophosphate (GPP), farnesyl pyrophosphate (FPP), and geranylgeranyl pyrophosphate (GGPP) require both isopentenyl pyrophosphate (IPP) and its isomer, dimethylallyl pyrophosphate (DMAPP), to create the backbone structure of all isoprenoids. To ensure sufficient production of DMAPP from IPP, an additional gene, idi (encoding isopentenyl pyrophosphate isomerase, SEQ ID NO 10), was amplified by PCR from *Escherichia coli* genomic DNA using primers containing an XmaI restriction enzyme site at the 5' ends. Both the amplified product (containing idi) and pBBRMevB were digested with XmaI and ligated, thereby placing idi at the 3' end of the MevB artificial operon. The resulting operon, containing the MevB operon and idi, is designated MBI (SEQ ID NO 12). The resulting plasmid (containing the operon of genes that encode for enzymes that convert mevalonate to IPP and DMAPP) was named pBBRMBI-2.

Addition of Polyprenyl Pyrophosphate Synthase(s) to MBI Operon

In order to direct products of the mevalonate pathway operons to the different classes of isoprenoids (monoterpenes, sesquiterpenes, diterpenes, etc.), various polyprenyl pyrophosphate synthases were cloned into the MBI operon, such as geranyl diphosphate (GPP) synthase, farnesyl pyrophosphate (FPP) synthase, and geranylgeranyl pyrophosphate (GGPP) synthase. Polyprenyl pyrophosphate synthases were cloned by PCR using forward primers with a SacII restriction site and reverse primers with a SacI restriction site. Using restriction enzymes and T4 DNA ligase, the polyprenyl pyrophosphate synthases were cloned between the SacII and SacI sites of pBBRMBI-2. For example, farnesyl pyrophosphate synthase gene ispA (SEQ ID NO 11) was isolated by PCR from *Escherichia coli* genomic DNA and cloned between the SacII and SacI sites of pBBRMBI-2, 3' of idi and the MevB operon. The resulting operon, containing the MevB operon, idi, and ispA (SEQ ID NO 11) has been designated MBIS (SEQ ID NO 13). The plasmid, which encodes the enzymes responsible for the synthesis of farnesyl pyrophosphate (FPP) from mevalonate, was named pBBRMBIS-2.

Example 2

Functionality of the Engineered Mevalonate Operon(s) by Growth/No-Growth Phenotype Functionality of the various genetic constructs was shown by expression of the artificial mevalonate-isoprenoid pathway. The plasmids were introduced into an *Escherichia coli* host in which the mevalonate-independent (DXP) isoprenoid pathway was inactivated. *Escherichia coli* strain DMY1 (Kuzuyama et al. (1999) Biosci. Biotechnol. Biochem. 63:776-778) contains a mutation (insertion/deletion) in the gene encoding for 1-deoxyxylulose 5-phosphate reductoisomerase (or DXR, the second step of the DXP pathway) that causes inactivation of the mevalonate-independent pathway. Since this mutation is lethal to *Escherichia coli*, the strain must be propagated in Luria-Bertoni (LB) medium (available from, for example, Sigma, St. Louis, Mo.) containing 0.5 mM of methylerithrytol (ME), the product of DXR; or it must have an alternate pathway for the production of isopentenyl pyrophosphate.

Cultures of *Escherichia coli* strain DMY1 were made electrocompetent according to the method of Sambrook et al. (above) and transformed with pBBRMBI-2, or both pBBRMBI-2 and pBADMevT. Newly transformed DMY1 cells were first allowed to recover on LB agar plates overnight, and were supplemented with 0.5 mM ME and appropriate antibiotics at 37° C. prior to testing growth on media devoid of ME. DMY1 cells transformed with only pBBRMBI-2 were plated on LB agar devoid of ME, but supplemented with 1 mM DL-mevalonate prepared by incubating 1 volume of 2 M DL-mevalonic acid lactone (Sigma, St. Louis, Mo.) with 1.02 volumes of 2 M KOH at 37° C. for 30 minutes. DMY1 cells transformed with both pBBRMBI-2 and pBADMevT plasmids were plated on LB agar with antibiotics only (no ME or DL-mevalonate). All test plates were incubated for 48 hours at 37° C.

*Escherichia coli* strain DMY1 cells containing pBBRMBI-2 were able to grow on LB agar plates with 1 mM DL-mevalonate, whereas *Escherichia coli* DMY1 cells without the plasmid or with pBBR1MCS-3 (empty vector control) did not grow. The MBI operon successfully converted the supplemented mevalonate to isopentenyl pyrophosphate and dimethylallyl pyrophosphate, thereby complementing the dxr deletion.

*Escherichia coli* strain DMY1 cells containing pBADMevT and pBBRMBI-2 were able to grow on LB agar plates not supplemented with DL-mevalonate, whereas *Escherichia coli* DMY1 cells without either of the plasmids could not grow on LB agar alone. The expression of the MevT and MBI operons successfully converted acetyl-CoA to isopentenyl pyrophosphate and dimethylallyl pyrophosphate in vivo, thereby restoring growth to *Escherichia coli* strain DMY1, in which the native DXP isoprenoid pathway is inactive.

Example 3

Production of Carotenoids from Mevalonate Using the MBI Artificial Operon

The production of a carotenoid was used to demonstrate the benefits of expressing the artificial mevalonate-dependent IPP biosynthetic pathway over the native *Escherichia coli* DXP-isoprenoid pathway. The increased productivity of the mevalonate-dependent isopentenyl pyrophosphate biosynthetic pathway encoded by the synthetic operons was assayed by coupling isopentenyl pyrophosphate production to the production of lycopene. This was accomplished by co-transforming *Escherichia coli* with pAC-LYC, a low-copy broad-host plasmid that expresses the genes encoding the pathway for lycopene production from farnesyl pyrophosphate. The genes expressed from pAC-LYC are crtE (geranylgeranyl pyrophosphate synthase), crtB (phytoene synthase), and crtI (phytoene desaturase) from *Erwinia herbicola*, which were cloned into pACYC184 using methods similar to those described in Examples 1 and 2. *Escherichia coli* naturally produces farnesyl pyrophosphate from two molecules of isopentenyl pyrophosphate and one molecule of dimethylallyl pyrophosphate through the enzyme farnesyl pyrophosphate synthase, ispA (SEQ ID NO 11). Alternatively, more flux can be directed from the mevalonate pathway to the lycopene pathway by including the *Escherichia coli* gene encoding farnesyl pyrophosphate synthase into the artificial operon(s).

From previous experiments (not described herein), it was found that the production of isopentenyl pyrophosphate from the mevalonate pathway operons was greater in the *Escherichia coli* strain DH10B than in the *Escherichia coli* strain DMY1. In order to demonstrate isopentenyl pyrophosphate production from the mevalonate pathway only, the gene encoding 1-deoxyxylulose 5-phosphate reductoisomerase, dxr, was inactivated in *Escherichia coli* strain DH10B by the method detailed by Datsenko et al. (2000), "One-step Inactivation of Chromosomal Genes in *Escherichia coli* K-12 Using PCR Products," *PNAS* 97:6640-6645. In the resulting *Escherichia coli* strain, named DPDXR1, the mevalonate independent pathway (or DXP pathway) is inactive, and in order to survive, the strain must either be propagated in LB medium containing 0.5 mM of methylerithrytol (ME) or have an alternate pathway for the production of isopentenyl pyrophosphate.

Figure 2:
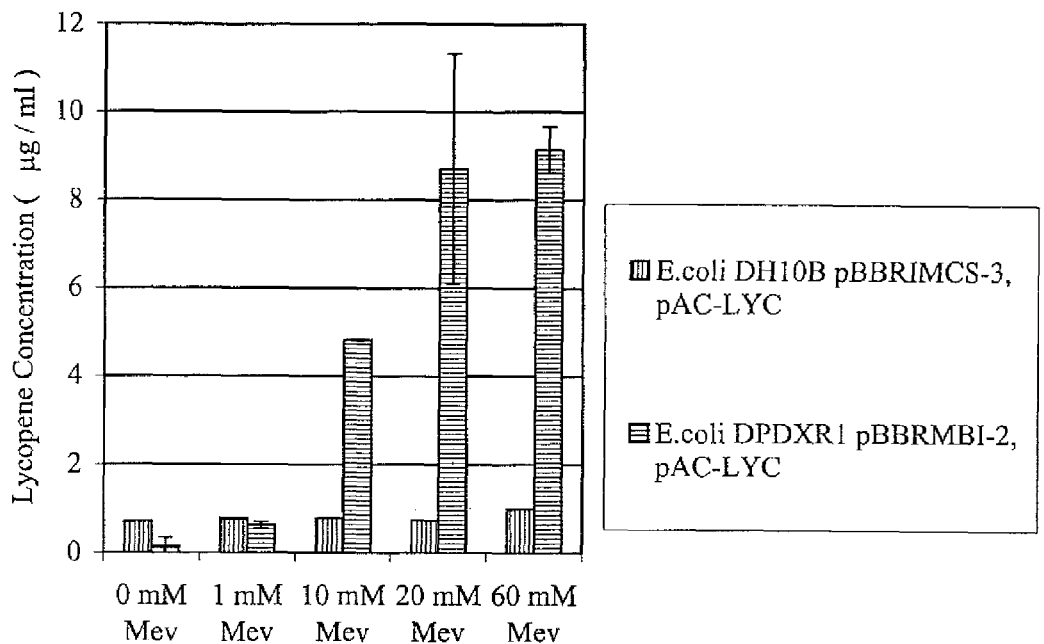
FIG. 2 is a graph illustrating the difference in the concentration of lycopene produced from natural levels of isopentenyl pyrophosphate in non-engineered *Escherichia coli* and from *Escherichia coli* engineered to overproduce isopentenyl pyrophosphate from a partial mevalonate-isoprenoid pathway, at different concentrations of mevalonate (Mev).

*Escherichia coli* strain DPDXR1 was transformed with pAC-LYC and pBBRMBI-2, while *Escherichia coli* strain DH10B was transformed with pAC-LYC and pBBR1MCS-3 (control) by electroporation. Transformants were selected on LB agar plates supplemented with 50 µg/ml chloramphenicol, 10 µg/ml tetracycline, and 1 mM DL-mevalonate by incubating overnight at 37° C. One colony of each strain (*Escherichia coli* DPDXR1 harboring pAC-LYC and pBBRMBI-2 or *Escherichia coli* DH10B harboring pAC-LYC and pBBR1MCS-3) was transferred from the LB agar selection plate to 5 ml of LB liquid medium also supplemented with 50 µg/ml chloramphenicol, 10 µg/ml tetracycline, and 1 mM DL-mevalonate. These seed cultures were incubated at 37° C. until they reached a stationary growth phase. The cell density of each seed culture was determined by measuring the optical density of the culture at a wavelength of 600 nm ($OD_{600}$). These seed cultures were then used to inoculate 5 ml test cultures of LB medium with appropriate antibiotics and increasing concentrations of DL-mevalonate. The volume of seed culture used to inoculate each fresh 5 ml culture was calculated to give an initial $OD_{600}$ value of 0.03. Test cultures were incubated for 48 hours at 30° C., after which growth was arrested by chilling the cultures on ice. The optical density of each culture was measured. One ml of each culture was harvested by centrifugation (25000×g, 30 seconds), the supernatant was removed, and cell pellets were suspended in 500 µL of acetone by rapid mixing with a Fisher Vortex Genie 2™ mixer (Scientific Industries, Inc., Bohemia, N.Y.). The acetone/cell mixtures were incubated at 55° C. for 10 minutes to aid in the extraction of lycopene from the cells. Extracted samples were centrifuged (25000×g, 7 minutes) to remove cell debris, and the cleared acetone supernatants were transferred to fresh tubes. The lycopene concentration of each acetone extraction was assayed by absorbance at 470 nm using a Beckman™ DU640 Spectrophotometer (Beckman Coulter, Inc., Fullerton, Calif.) and a 400 µL quartz cuvette. Absorbance values at 470 nm were converted to lycopene concentrations using linear regressions from a standard curve produced using pure lycopene (Sigma, St. Louis, Mo.). Final lycopene concentrations of each strain at increasing concentration of substrate is reported in FIG. 2. As shown in FIG. 2, lycopene production as a function of substrate concentration following shaking for 48 hours at 30° C. demonstrated that lycopene produced from natural levels of isopentenyl pyrophosphate in non-engineered *Escherichia coli* strain DH10B (vertical stripes) remains relatively constant, while lycopene produced from isopentenyl pyrophosphate generated by engineered *Escherichia coli* strain DPDXR1 harboring the plasmid, pBBRMBI-2 (horizontal stripes), significantly increases at mevalonate substrate concentrations of 10 mM and higher.

Example 4

Production of Carotenoids from Luria-Bertoni Broth Using the Complete Mevalonate Pathway It was demonstrated that significantly higher levels of isopentenyl pyrophosphate and isoprenoids derived therefrom were produced using the complete mevalonate-isoprenoid operon when compared to the native DXP pathway. The complete mevalonate-isoprenoid pathway was expressed using the two operons, MevT and MBI, which were expressed from pBADMevT and pBBRMBI-2, respectively, and coupled to pAC-LYC to demonstrate the in vivo production of the carotenoid lycopene, using precursors produced by primary cellular metabolism.

Figure 3:
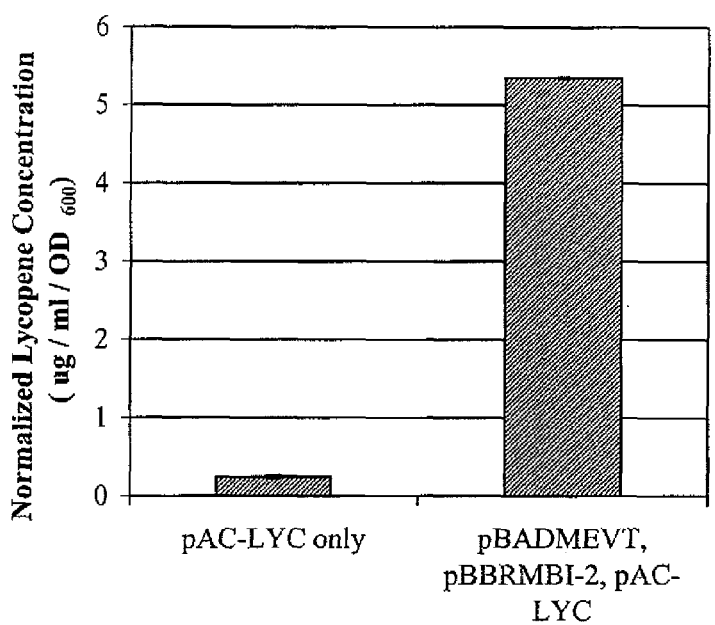
FIG. 3 is a graph illustrating the difference in normalized lycopene concentration produced from natural levels of isopentenyl pyrophosphate in non-engineered *Escherichia coli* and from *Escherichia coli* engineered to overproduce isopentenyl pyrophosphate from the complete mevalonate-isoprenoid pathway.

*Escherichia coli* strain DH10B was transformed with pBADMevT, pBBRMBI-2, and pAC-LYC by electroporation. Transformants were selected on LB agar plates containing 50 µg/ml carbenicillin, 10 µg/ml tetracycline, and 50 µg/ml chloramphenicol. A single colony of the strain was transferred from the LB agar plate to 5 ml of LB liquid medium containing the same antibiotics. This seed culture was incubated by shaking at 37° C. until growth reached a stationary phase. The cell density of each seed culture was measured at $OD_{600}$, and the cells were used to inoculate 5 ml test cultures of fresh LB medium plus the same antibiotics to give an $OD_{600}$ of 0.03. The test cultures were incubated for 48 hours at 30° C., after which growth was arrested by chilling the cultures on ice. The remainder of the experimental procedure was followed as described in Example 3. Final lycopene production (µg/ml lycopene per $OD_{600}$) of the pBADMevT, pBBRMBI-2, pAC-LYC plasmid system was compared to the lycopene production from pAC-LYC plasmid only (control) in the *Escherichia coli* DH10B strain, as shown in FIG. 3. This figure illustrates, in graph form, the amount of lycopene produced for each strain, normalized for cell density, after shaking for 48 hours at 30° C. The column on the left represents the amount of lycopene produced naturally in a non-engineered *Escherichia coli* strain (containing only pAC-LYC as a control). The column on the right represents the amount of lycopene produced from an *Escherichia coli* strain engineered to overproduce isopentenyl pyrophosphate from the mevalonate-isprenoid pathway.

Example 5

Production of Terpenes by Coupling of Artificial Mevalonate Operon(s) to Terpene Cyclases Many valuable natural products were produced from the isoprenoid biosynthetic pathways described herein. Depending on the desired isoprenoid, the described operon(s) were modified, and/or additional operons or other means for chemical synthesis were provided to produce the precursors for the various classes. The following experiments demonstrated the synthesis of sesquiterpenes using the farnesyl pyrophosphate synthase, ispA (SEQ ID NO 11), as well as the means by which other classes of isoprenoids, such as diterpenes, were synthesized by varying the synthase cloned into the operon(s) to create the desired precursor.

In vivo Production of Sesquiterpenes

Amorphadiene, a precursor to the antimalarial drug artemisinin, was produced from the co-expression of the mevalonate-isoprenoid pathway, along with a sesquiterpene cyclase-encoding amorphadiene synthesis. The MBIS operon expressed from pBBRMBIS-2 was coupled with amorpha-4,11-diene synthase (ADS) for the in vivo production of the sesquiterpene amorpha-4,11-diene in *Escherichia coli*.

A gene coding for amorpha-4,11-diene synthase (ADS) was constructed so that, upon translation, the amino acid sequence would be identical to that described by Merke et al. (2000) *Ach. Biochem. Biophys.* 381(2): 173-180. The ADS gene contains recognition sequences 5' and 3' of the coding DNA corresponding to the restriction endonucleases NcoI and XmaI, respectively. The ADS gene was digested to completion with the restriction endonucleases, along with DNA for the plasmid pTrc99A. The 1644-bp gene fragment and the 4155-bp plasmid fragment were purified using 0.7% agarose gels and a Qiagen gel purification kit (Valencia, Calif.) according to the manufacturer's instructions. The two fragments were then ligated using T4 DNA ligase from New England Biolabs (Beverly, Mass.), resulting in plasmid pTRCADS. The insert was verified by sequencing to be the amorpha-4,11-diene synthase gene.

*Escherichia coli* strain DH10B was transformed with both the pBBRMBIS-2 and pTRCADS plasmids by electroporation. Bacterial colonies were then grown on Luria-Bertoni (LB) agar containing 50 µg/ml carbenicillin and 10 µg/ml tetracycline. A single bacterial colony was transferred from the agar plates to 5 ml LB liquid medium containing the same antibiotics and cultured by shaking at 37° C. for 16-18 hours. Five hundred µL of this culture was transferred into 5 ml fresh LB liquid medium with the same antibiotics, then cultured by shaking at 37° C. to an optical density of 0.816 at 600 nm ($OD_{600}$). A 1.6 ml portion of this culture was used to inoculate a flask containing 100 ml of LB liquid medium with 50 µg/ml carbenicillin and 10 µg/ml tetracycline, which was cultured by shaking at 37° C. After 1.5 hours, 1 ml of 1 M mevalonate and 100 µL of 500 mM isopropylthio-β-D-galactoside (IPTG) were added to the culture, and it continued to be shaken at 37° C. Amorpha-4,11-diene concentration was determined by extracting 700 µl samples (taken hourly) with 700 µl of ethyl acetate in glass vials. The samples were then shaken at maximum speed on a Fisher Vortex Genie 2™ mixer (Scientific Industries, Inc., Bohemia, N.Y.) for three minutes. The samples were allowed to settle in order to separate the ethyl acetate-water emulsions. Prior to gas chromatography-mass spectrometry analysis, the ethyl acetate layer was transferred with a glass Pasteur pipette to a clean glass vial.

Ethyl acetate culture extracts were analyzed on a Hewlett-Packard 6890 gas chromatograph/mass spectrometer (GC/MS). A 1 µl sample was separated on the GC using a DB-5 column (available from, for example, Agilent Technologies, Inc., Palo Alto, Calif.) and helium carrier gas. The oven cycle for each sample was 80° C. for two minutes, increasing temperature at 30° C./minute to a temperature of 160° C., increasing temperature at 3° C./min to 170° C., increasing temperature at 50° C./minute to 300° C., and a hold at 300° C. for two minutes. The resolved samples were analyzed by a Hewlett-Packard model 5973 mass selective detector that monitored ions 189 and 204 m/z. Previous mass spectra demonstrated that the amorpha-4,11-diene synthase product was amorphadiene and that amorphadiene had a retention time of 7.9 minutes using this GC protocol. Since pure standards of amorpha-4,11-diene are not available, the concentrations must be quantified in terms of caryophyllene equivalence. A standard curve for caryophyllene has been determined previously, based on a pure standard from Sigma (St. Louis, Mo.). The amorpha-4,11-diene concentration is based on the relative abundance of 189 and 204 m/z ions to the abundance of the total ions in the mass spectra of the two compounds.

Figure 4:
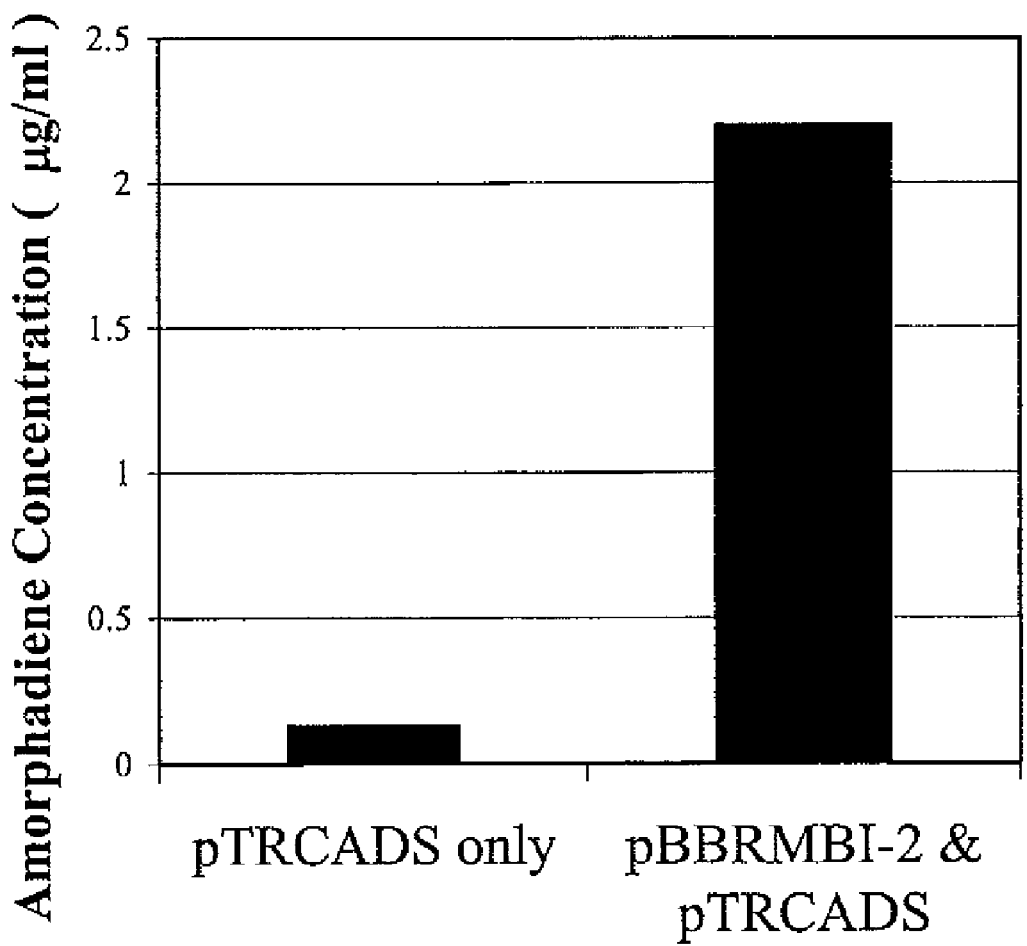
FIG. 4 is a graph illustrating the difference in amorphadiene concentration produced from natural levels of isopentenyl pyrophosphate in non-engineered *Escherichia coli* and from *Escherichia coli* engineered to overproduce isopentenyl pyrophosphate from a partial mevalonate-isoprenoid pathway.

The amorphadiene concentration of the cultures seven hours after the addition of IPTG and mevalonate is shown in FIG. 4. The figure shows the concentration of amorphadiene produced seven hours after the addition of mevalonate and isopropylthio-β-D-galactoside (IPTG). The column on the left shows the concentration of amorphadiene produced from non-engineered *Escherichia coli* harboring the pTRCADS plasmid alone. The column on the right shows the concentration of amorphadiene produced from engineered *Escherichia coli* harboring the pBBRMBIS-2 and pTRCADS plasmids. The *Escherichia coli* strain engineered to make farnesyl pyrophosphate from the mevalonate isoprenoid pathway produced 2.2 µg/ml amorphadiene, whereas the non-engineered strain (without the mevalonate isoprenoid pathway) produced only 0.13 µg/ml.

In vivo Production of Diterpenes

The plasmid pBBRMBIS-2 was modified to include a gene encoding geranylgeranyl pyrophosphate synthase (instead of farnesyl pyrophosphate synthase). To demonstrate the utility of the artificial mevalonate-isoprenoid for in viva diterpene production, this modified expression system was coupled with a plasmid expressing casbene synthase. Casbene synthase cDNA cloned into expression vector pET21-d (Hill et al. (1996), *Arch Biochem. Biophys.* 336:283-289) was cut out with SalI (New England Biolabs, Beverly, Mass.) and NcoI (New England Biolabs, Beverly, Mass.) and re-cloned into high-copy-number expression vector pTrc99A. The gene fragment and the plasmid fragment were purified with 0.7% agarose gels using a Qiagen gel purification kit (Valencia, Calif.) according to the manufacturer's instructions. The two fragments were then ligated using T4 DNA ligase from New England Biolabs (Beverly, Mass.), resulting in plasmid pTrc-CAS.

*Escherichia coli* strain DH10B was transformed with both the modified pBBRMBIS-2 and pTrcCAS plasmids by electroporation. Bacterial colonies were then grown on Luria-Bertoni (LB) agar containing 50 µg/ml carbenicillin and 10 µg/ml tetracycline. A single bacterial colony was transferred from the agar plates to 5 ml LB liquid medium containing the same antibiotics and cultured by shaking at 37° C. for 16-18 hours. Five hundred microliters of this culture was transferred into 5 ml fresh LB liquid medium with 50 µg/ml carbenicillin and 10 µg/ml tetracycline, and cultured by shaking at 37° C. to an optical density of 0.816 at 600 nm ($OD_{600}$). A 150 µL portion of this culture was used to inoculate a flask containing 25 ml of LB liquid medium with 50 µg/ml carbenicillin, 10 µg/ml tetracycline, and 20 mM mevalonate. This mixture was cultured by shaking at 37° C. After 1.5 hours, 250 µL of 100 mM IPTG were added to the culture, and it continued to be shaken at 37° C. Casbene concentration of the culture was determined hourly by extracting 450 µl samples. To these samples was added 450 µL of ethyl acetate in a glass vial. The samples were then shaken on a Fisher Vortex Genie 2™ mixer (Scientific Industries, Inc., Bohemia, N.Y.) for three minutes. The samples were allowed to settle in order to separate the ethyl acetate-water emulsion. The ethyl acetate layer was transferred with a glass Pasteur pipette to a clean vial.

Figure 5:
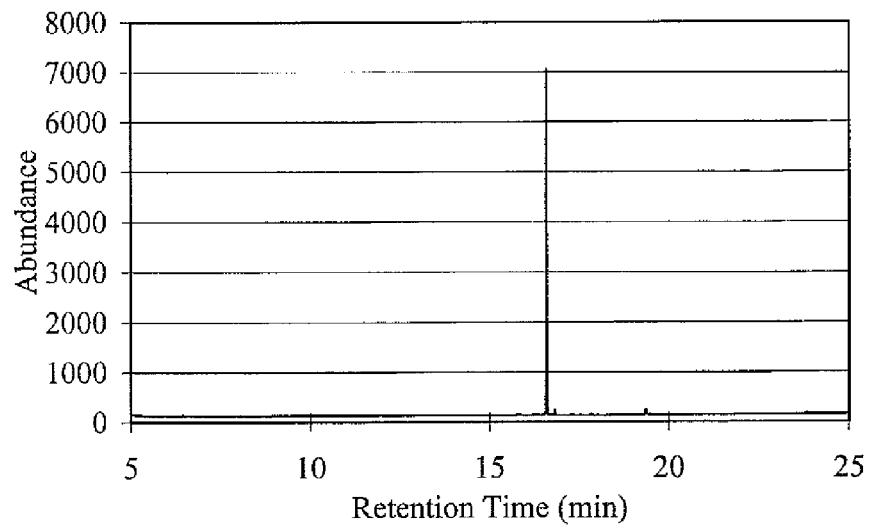
FIG. 5 is a gas chromatographic spectrum illustrating the production of diterpene using ethyl acetate extracts from *Escherichia coli* engineered to produce isoprenoids from the artificial, modified MBIS operon (a partial mevalonate-isoprenoid pathway), and expressing a casbene cyclase.
Figure 6:
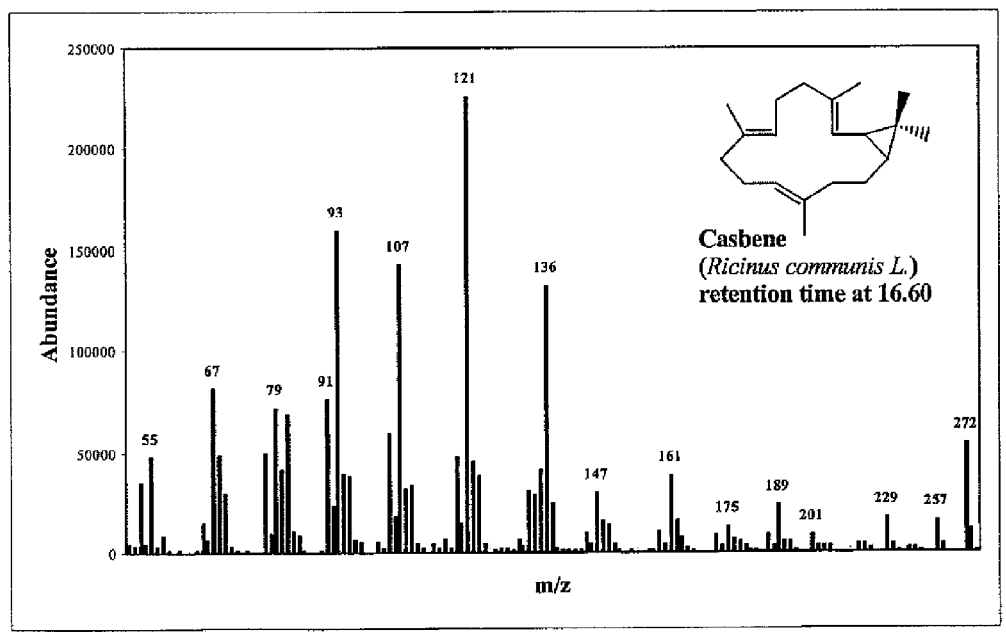
FIG. 6 is the mass spectrum of the isoprenoid casbene.

Ethyl acetate culture extracts were analyzed on a Hewlett-Packard 6890 gas chromatograph/mass spectrometer (GC/MS). A 1 µl sample was separated on the GC using a DB-5 column (available from, for example, Agilent Technologies, Inc., Palo Alto) and helium carrier gas. The oven cycle for each sample was 80° C. for two minutes, increasing temperature at 10° C./minute to a temperature of 300° C., and a hold at 300° C. for two minutes. The resolved samples were analyzed by a Hewlett-Packard model 5973 mass selective detector that monitored ions 229, 257, and 272 m/z. Previous mass spectra had demonstrated that the casbene synthase product was casbene and that casbene had a retention time of 16.6 minutes using this GC protocol. FIG. 5 shows the gas chromatographic analysis and resulting GC/MS chromatogram for the ethyl acetate extracts taken seven hours after addition of IPTG from *Escherichia coli* engineered to produce isoprenoids from the artificial modified MBIS operon, thereby expressing the casbene cyclase from the pTrcCAS plasmid. As a reference, FIG. 6 shows the spectrogram for casbene.

SEQUENCE LISTING
Assignment of SEQ ID NOS

SEQ ID NO 1   acetoacetyl-CoA thiolase nucleotide sequence
SEQ ID NO 2   HMG-CoA synthase nucleotide sequence
SEQ ID NO 3   HMG-CoA reductase nucleotide sequence
SEQ ID NO 4   mevalonate kinase nucletotide sequence
SEQ ID NO 5   phosphomevalonate kinase nucleotide sequence
SEQ ID NO 6   mevalonate pyrophosphate decarboxylase nucleotide sequence
SEQ ID NO 7   "single operon" nucleotide sequence
SEQ ID NO 8   "MEVT" operon nucleotide sequence
SEQ ID NO 9   "MEVB" operon nucleotide sequence (not including the transcription terminator)
SEQ ID NO 10  Isopentenyl pyrophosphate isomerase (idi) nucleotide sequence
SEQ ID NO 11  Farnesyl pyrophosphate synthase (ispA) nucleotide sequence
SEQ ID NO 12  "MBI" operon nucleotide sequenceF
SEQ ID NO 13  "MBIS" operon nucleotide sequence SEQ ID NO 1 Acetoacetyl-CoA thiolase nucleotide sequence
    1 ATGAAAAATT GTGTCATCGT CAGTGCGGTA CGTACTGCTA TCGGTAGTTT TAACGGTTCA
   61 CTCGCTTCCA CCAGCGCCAT CGACCTGGGG GCGACAGTAA TTAAAGCCGC CATTGAACGT
  121 GCAAAAATCG ATTCACAACA CGTTGATGAA GTGATTATGG GTAACGTGTT ACAAGCCGGG
  181 CTGGGGCAAA ATCCGGCGCG TCAGGCACTG TTAAAAAGCG GGCTGGCAGA AACGGTGTGC
  241 GGATTCACGG TCAATAAAGT ATGTGGTTCG GGTCTTAAAA GTGTGGCGCT TGCCGCCCAG
  301 GCCATTCAGG CAGGTCAGGC GCAGAGCATT GTGGCGGGGG GTATGGAAAA TATGAGTTTA
  361 GCCCCCTACT TACTCGATGC AAAAGCACGC TCTGGTTATC GTCTTGGAGA CGGACAGGTT
  421 TATGACGTAA TCCTGCGCGA TGGCCTGATG TGCGCCACCC ATGGTTATCA TATGGGGATT
  481 ACCGCCGAAA ACGTGGCTAA AGAGTACGGA ATTACCCGTG AAATGCAGGA TGAACTGGCG
  541 CTACATTCAC AGCGTAAAGC GGCAGCCGCA ATTGAGTCCG GTGCTTTTAC AGCCGAAATC
  601 GTCCCGGTAA ATGTTGTCAC TCGAAAGAAA ACCTTCGTCT TCAGTCAAGA CGAATTCCCG
  661 AAAGCGAATT CAACGGCTGA AGCGTTAGGT GCATTGCGCC CGGCCTTCGA TAAAGCAGGA
  721 ACAGTCACCG CTGGGAACGC GTCTGGTATT AACGACGGTG CTGCCGCTCT GGTGATTATG
  781 GAAGAATCTG CGGCGCTGGC AGCAGGCCTT ACCCCCCTGG CTCGCATTAA AAGTTATGCC
  841 AGCGCTGGCG TGCCCCCCGC ATTGATGGGT ATGGGGCCAG TACCTGCCAC GCAAAAAGCG
  901 TTACAACTGG CGGGGCTGCA ACTGGCGGAT ATTGATCTCA TTGAGGCTAA TGAAGCATTT
  961 GCTGCACAGT TCCTTGCCGT TGGGAAAAAC CTGGGCTTTG ATTCTGAGAA AGTGAATGTC
 1021 AACGGCGGGG CCATCGCGCT CGGGCATCCT ATCGGTGCCA GTGGTGCTCG TATTCTGGTC
 1081 ACACTATTAC ATGCCATGCA GGCACGCGAT AAAACGCTGG GGCTGGCAAC ACTGTGCATT
 1141 GGCGGCGGTC AGGGAATTGC GATGGTGATT GAACGGTTGA ATTAA SEQ ID NO 2 HMG-CoA synthase nucleotide sequence
    1 ATGAAACTCT CAACTAAACT TTGTTGGTGT GGTATTAAAG GAAGACTTAG GCCGCAAAAG
   61 CAACAACAAT TACACAATAC AAACTTGCAA ATGACTGAAC TAAAAAACA AAAGACCGCT
  121 GAACAAAAAA CCAGACCTCA AAATGTCGGT ATTAAGGTA TCCAAATTTA CATCCCAACT
  181 CAATGTGTCA ACCAATCTGA GCTAGAGAAA TTTGATGGCG TTTCTCAAGG TAAATACACA
  241 ATTGGTCTGG GCCAAACCAA CATGTCTTTT GTCAATGACA GAGAAGATAT CTACTCGATG
  301 TCCCTAACTG TTTTGTCTAA GTTGATCAAG AGTTACAACA TCGACACCAA CAAATTGGT
  361 AGATTAGAAG TCGGTACTGA AACTCTGATT GACAAGTCCA AGTCTGTCAA GTCTGTCTTG
  421 ATGCAATTGT TTGGTGAAAA CACTGACGTC GAAGGTATTG ACACGCTTAA TGCCTGTTAC
  481 GGTGGTACCA ACGCGTTGTT CAACTCTTTG AACTGGATTG AATCTAACGC ATGGGATGGT
  541 AGAGACGCCA TTGTAGTTTG CGGTGATATT GCCATCTACG ATAAGGGTGC CGCAAGACCA
  601 ACCGGTGGTG CCGGTACTGT TGCTATGTGG ATCGGTCCTG ATGCTCCAAT TGTATTTGAC
  661 TCTGTAAGAG CTTCTTACAT GGAACACGCC TACGATTTTT ACAAGCCAGA TTTCACCAGC
  721 GAATATCCTT ACGTCGATGG TCATTTTTCA TTAACTTGTT ACGTCAAGGC TCTTGATCAA
  781 GTTTACAAGA GTTATTCCAA GAAGGCTATT TCTAAAGGGT TGGTTAGCGA TCCCGCTGGT
  841 TCGGATGCTT TGAACGTTTT GAAATATTTC GACTACAACG TTTTCCATGT TCCAACCTGT
  901 AAATTGGTCA CAAAATCATA CGGTAGATTA CTATATAACG ATTTCAGAGC CAATCCTCAA
  961 TTGTTCCCAG AAGTTGACGC CGAATTAGCT ACTCGCGATT ATGACGAATC TTTAACCGAT
 1021 AAGAACATTG AAAAAACTTT TGTTAATGTT GCTAAGCCAT TCCACAAAGA GAGAGTTGCC
 1081 CAATCTTTGA TTGTTCCAAC AAACACAGGT AACATGTACA CCGCATCTGT TTATGCCGCC
 1141 TTTGCATCTC TATTAAACTA TGTTGGATCT GACGACTTAC AAGGCAAGCG TGTTGGTTTA
 1201 TTTTCTTACG GTTCCGGTTT AGCTGCATCT CTATATTCTT GCAAATTGT TGGTGACGTC
 1261 CAACATATTA TCAAGGAATT AGATATTACT AACAAATTAG CCAAGAGAAT CACCGAAACT
 1321 CCAAAGGATT ACGAAGCTGC CATCGAATTG AGAGAAAATG CCCATTTGAA GAAGAACTTC
 1381 AAACCTCAAG GTTCCATTGA GCATTTGCAA AGTGGTGTTT ACTACTTGAC CAACATCGAT
 1441 GACAAATTTA GAAGATCTTA CGATGTTAAA AAATAA

SEQUENCE LISTING
Assignment of SEQ ID NOS

SEQ ID NO 3 Truncated HMG-CoA reductase nucleotide sequence

Artificial Start Codon

```
   1 ATGGTTTTAA CCAATAAAAC AGTCATTTCT GGATCGAAAG TCAAAAGTTT ATCATCTGCG
       ↑ Base Pair 1660 of S. cervisiae HMG1

61 CAATCGAGCT CATCAGGACC TTCATCATCT AGTGAGGAAG ATGATTCCCG CGATATTGAA
 121 AGCTTGGATA AGAAAATACG TCCTTTAGAA GAATTAGAAG CATTATTAAG TAGTGGAAAT
 181 ACAAAACAAT TGAAGAACAA AGAGGTCGCT GCCTTGGTTA TTCACGGTAA GTTACCTTTG
 241 TACGCTTTGG AGAAAAAATT AGGTGATACT ACGAGAGCGG TTGCGGTACG TAGGAAGGCT
 301 CTTTCAATTT TGGCAGAAGC TCCTGTATTA GCATCTGATC GTTTACCATA TAAAAATTAT
 361 GACTACGACC GCGTATTTGG CGCTTGTTGT GAAAATGTTA TAGGTTACAT GCCTTTGCCC
 421 GTTGGTGTTA TAGGCCCCTT GGTTATCGAT GGTACATCTT ATCATATACC AATGGCAACT
 481 ACAGAGGGTT GTTTGGTAGC TTCTGCCATG CGTGGCTGTA AGGCAATCAA TGCTGGCGGT
 541 GGTGCAACAA CTGTTTTAAC TAAGGATGGT ATGACAAGAG CCCAGTAGT CCGTTTCCCA
 601 ACTTTGAAAA GATCTGGTGC CTGTAAGATA TGGTTAGACT CAGAAGAGGG ACAAAACGCA
 661 ATTAAAAAAG CTTTTAACTC TACATCAAGA TTTGCACGTC TGCAACATAT TCAAACTTGT
 721 CTAGCAGGAG ATTTACTCTT CATGAGATTT AGAACAACTA CTGGTGACGC AATGGGTATG
 781 AATATGATTT CTAAAGGTGT CGAATACTCA TTAAAGCAAA TGGTAGAAGA GTATGGCTGG
 841 GAAGATATGG AGGTTGTCTC CGTTTCTGGT AACTACTGTA CCGACAAAAA ACCAGCTGCC
 901 ATCAACTGGA TCGAAGGTCG TGGTAAGAGT GTCGTCGCAG AAGCTACTAT TCCTGGTGAT
 961 GTTGTCAGAA AAGTGTTAAA AAGTGATGTT TCCGCATTGG TTGAGTTGAA CATTGCTAAG
1021 AATTTGGTTG GATCTGCAAT GGCTGGGTCT GTTGGTGGAT TAACGCACA TGCAGCTAAT
1081 TTAGTGACAG CTGTTTTCTT GGCATTAGGA CAAGATCCTG CACAAAATGT TGAAAGTTCC
1141 AACTGTATAA CATTGATGAA AGAAGTGGAC GGTGATTTGA GAATTTCCGT ATCCATGCCA
1201 TCCATCGAAG TAGGTACCAT CGGTGGTGGT ACTGTTCTAG AACCACAAGG TGCCATGTTG
1261 GACTTATTAG GTGTAAGAGG CCCGCATGCT ACCGCTCCTG GTACCAACGC ACGTCAATTA
1321 GCAAGAATAG TTGCCTGTGC CCCGCATGCT ACCGCTCCTG GTACCAACGC ACGTCAATTA
1381 GCCGGCCATT TGGTTCAAAG TCATATGACC CACAACAGGA AACCTGCTGA ACCAACAAAA
1441 CCTAACAATT TGGACGCCAC TGATATAAAT CGTTTGAAAG ATGGGTCCGT CACCTGCATT
1501 AAATCCTAA
```

SEQ ID NO 4 Mevalonate kinase nucletotide sequence
```
   1 ATGTCATTAC CGTTCTTAAC TTCTGCACCG GGAAAGGTTA TTATTTTGG TGAACACTCT
  61 GCTGTGTACA ACAAGCCTGC CGTCGCTGCT AGTGTGTCTG CGTTGAGAAC CTACCTGCTA
 121 ATAAGCGAGT CATCTGCACC AGATACTATT GAATTGGACT TCCCGGACAT TAGCTTTAAT
 181 CATAAGTGGT CCATCAATGA TTTCAATGCC ATCACCGAGG ATCAAGTAAA CTCCCAAAAA
 241 TTGGCCAAGG CTCAACAAGC CACCGATGGC TTGTCTCAGG AACTCGTTAG TCTTTTGGAT
 301 CCGTTGTTAG CTCAACTATC CGAATCCTTC CACTACCATG GCAGCGTTTTG TTTCGTGTAT
 361 ATGTTTGTTT GCCTATGCCC CCATGCCAAG AATATTAAGT TTTCTTTAAA GTCTACTTTA
 421 CCCATCGGTG CTGGGTTGGG CTCAAGCGCC TCTATTTCTG TATCACTGGC CTTAGCTATG
 481 GCCTACTTGG GGGGGTTAAT AGGATCTAAT GACTTGGAAA AGCTGTCAGA AAACGATAAG
 541 CATATAGTGA ATCAATGGGC CTTCATAGGT GAAAAGTGTA TTCACGGTAC CCCTTCAGGA
 601 ATAGATAACG CTGTGGCCAC TTATGGTAAT GCCCTGCTAT TTGAAAAAGA CTCACATAAT
 661 GGAACAATAA ACACAAACAA TTTTAAGTTC TTAGATGATT TCCCAGCCAT TCCAATGATC
 721 CTAACCTATA CTAGAATTCC AAGGTCTACA AAAGATCTTG TTGCTCGCGT TCGTGTGTTG
 781 GTCACCGAGA AATTTCCTGA AGTTATGAAG CCAATTCTAG ATGCCATGGG TGAATGTGCC
 841 CTACAAGGCT TAGAGATCAT GACTAAGTTA AGTAAATGTA AAGCCACCGA TGACGAGGCT
 901 GTAGAAACTA ATAATGAACT GTATGAACAA CTATTGGAAT TGATAAGAAT AAATCATGGA
 961 CTGCTTGTCT CAATCGGTGT TTCTCATCCT GGATTAGAAC TTATTAAAAA TCTGAGCGAT
1021 GATTTGAGAA TTGGCTCCAC AAAACTTACC GGTGCTGGTG GCGGCGGTTG CTCTTTGACT
1081 TTGTTACGAA GAGACATTAC TCAAGAGCAA ATTGACAGCT TCAAAAAGAA ATTGCAAGAT
1141 GATTTTAGTT ACGAGACATT TGAAACAGAC TTGGGTGGGA CTGCTGCTG TTTGTTAAGC
1201 GCAAAAAATT TGAATAAAGA TCTTAAAATC AAATCCCTAG TATTCCAATT ATTTGAAAAT
1261 AAAACTACCA CAAAGCAACA AATTGACGAT CTATTATTGC CAGGAAACAC GAATTTACCA
1321 TGGACTTCAT AG
```

SEQ ID NO 5 Phosphomevalonate kinase nucleotide sequence
```
   1 ATGTCAGAGT TGAGAGCCTT CAGTGCCCCA GGGAAAGCGT TACTAGCTGG TGGATATTTA
  61 GTTTTAGATA CAAAATATGA AGCATTTGTA GTCGGATTAT CGGCAAGAAT GCATGCTGTA
 121 GCCCATCCTT ACGGTTCATT GCAAGGGTCT GATAAGTTTG AAGTGCGTGT GAAAAGTAAA
 181 CAATTTAAAG ATGGGGAGTG GCTGTACCAT ATAAGTCCTA AAGTGGCTT CATTCCTGTT
 241 TCGATAGGCG GATCTAAGAA CCCTTTCATT GAAANAGTTA TCGCTAACGT ATTTAGCTAC
 301 TTTAAACCTA ACATGACGA CTACTGCAAT AGAAACTTGT TCGTTATTGA TATTTCTCT
 361 GATGATGCCT ACCATTCTCA GGAGGATAGC GTTACCGAAC ATCGTGGCAA CAGAAGATTG
 421 AGTTTTCATT CGCACAGAAT TGAAGAAGTT CCCAAAACAG GGCTGGGCTC CTCGGCAGGT
 481 TTAGTCACAG TTTTAACTAC AGCTTTGGCC TCCTTTTTTG TATCGGACCT GGAAAATAAT
 541 GTAGACAAAT ATAGAGAAGT TATTCATAAT TTAGCACAAG TTGCTCATTG TCAAGCTCAG
 601 GGTAAAATTG GAAGCGGGTT TGATGTAGCG GCGGCAGCAT ATGGATCTAT CAGATATAGA
 661 AGATTCCCAC CCGCATTAAT CTCTAATTTG CCAGATATTG GAAGTGCTAC TTACGGCAGT
 721 AAACTGCGCG ATTTGGTTGA TGAAGAAGAC TGGAATATTA CGATTAAAAG TAACCATTTA
 781 CCTTCGGGAT TAACTTTATG GATGGGCGAT ATTAAGAATG GTTCAGAAAC AGTAAAACTG
 841 GTCCAGAAGG TAAAAAATTG GTATGATTCG CATATGCCAA AAGCTTGAA AATATATACA
 901 GAACTCGATC ATGCAAATTC TAGATTTATG GATGGACTAT CTAAACTAGA TCGCTTACAC
```

```
 961 GAGACTCATG ACGATTACAG CGATCAGATA TTTGAGTCTC TTGAGAGGAA TGACTGTACC
1021 TGTCAAAAGT ATCCTGAAAT CACAGAAGTT AGAGATGCAG TTGCCACAAT TAGACGTTCC
1081 TTTAGAAAAA TAACTAAAGA ATCTGGTGCC GATATCGAAC CTCCCGTACA AACTAGCTTA
1141 TTGGATGATT GCCAGACCTT AAAAGGAGTT CTTACTTGCT TAATACCTGG TGCTGGTGGT
1201 TATGACGCCA TTGCAGTGAT TACTAAGCAA GATGTTGATC TTAGGGCTCA AACCGCTAAT
1261 GACAAAAGAT TTTCTAAGGT TCAATGGCTG GATGTAACTC AGGCTGACTG GGGTGTTAGG
1321 AAAGAAAAAG ATCCGGAAAC TTATCTTGAT AAATAG

SEQ ID NO 6 Mevalonate pyrophosphate decarboxylase nucleotide sequence
   1 ATGACCGTTT ACACAGCATC CGTTACCGCA CCCGTCAACA TCGCAACCCT TAAGTATTGG
  61 GGGAAAAGGG ACACGAAGTT GAATCTGCCC ACCAATTCGT CCATATCAGT GACTTTATCG
 121 CAAGATGACC TCAGAACGTT GACCTCTGCG GCTACTGCAC CTGAGTTTGA ACGCGACACT
 181 TTGTGGTTAA ATGGAGAACC ACACAGCATC GACAATGAAA GAACTCAAAA TTGTCTGCGC
 241 GACCTACGCC AATTAAGAAA GGAAATGGAA TCGAAGGACG CCTCATTGCC CACATTATCT
 301 CAATGGAAAC TCCACATTGT CTCCGAAAAT AACTTTCCTA CAGCAGCTGG TTTAGCTTCC
 361 TCCGCTGCTG GCTTTGCTGC ATTGGTCTCT GCAATTGCTA AGTTATACCA ATTACCACAG
 421 TCAACTTCAG AAATATCTAG AATAGCAAGA AAGGGGTCTG GTTCAGCTTG TAGATCGTTG
 481 TTTGGCGGAT ACGTGGCCTG GGAAATGGGA AAAGCTGAAG ATGGTCATGA TTCCATGGCA
 541 GTACAAATCG CAGACAGCTC TGACTGGCCT CAGATGAAAG CTTGTGTCCT AGTTGTCAGC
 601 GATATTAAAA AGGATGTGAG TTCCACTCAG GGTATGCAAT TGACCGTTGGC AACCTCCGAA
 661 CTATTTAAAG AAAGAATTGA ACATGTCGTA CCAAAGAGAT TTGAAGTCAT GCGTAAAGCC
 721 ATTGTTGAAA AAGATTTCGC CACCTTTGCA AAGGAAACAA TGATGGATTC CAACTCTTTC
 781 CATGCCACAT GTTTGGACTC TTTCGCTCCA ATATTCTACA TGAATGACAC TTCCAAGCGT
 841 ATCATCAGTT GGTGCCACAC CATTAATCAG TTTTACGGAG AAACAATCGT TGCATACACG
 901 TTTGATGCAG GTCCAAATGC TGTGTTGTAC TACTTAGCTG AAAATGAGTC GAAACTCTTT
 961 GCATTTATCT ATAAATTGTT TGGCTCTGTT CCTGGATGGG ACAAGAAATT TACTACTGAG
1021 CAGCTTGAGG CTTTCAACCA TCAATTTGAA TCATCTAACT TTACTGCACG TGAATTGGAT
1081 CTTGAGTTGC AAAAGGATGT TGCCAGAGTG ATTTTAACTC AAGTCGGTTC AGGCCCACAA
1141 GAAACAAACG AATCTTTGAT TGACGCAAAG ACTGGTCTAC CAAAGGAATA A SEQ ID NO 7 "single operon" nucleotide sequence P_BAD Promoter
   1 GACGCTTTTT ATCGCAACTC TCTACTGTTT CTCCATACCC GTTTTTTTGG GCTAGCAGGA RBS         |—> Start Isopentyl
  61 GGAATTCACC ATGGTACCCG GGAGGAGGAT TACTATATGC AAACGGAACA CGTCATTTTA Prophosphate Isomerase
 121 TTGAATGCAC AGGGAGTTCC CACGGGTACG CTGGAAAAGT ATGCCGCACA CACGGCAGAC
 181 ACCCGCTTAC ATCTCGCGTT CTCCAGTTGG CTGTTTAATG CCAAAGGACA ATTATTAGTT
 241 ACCCGCCGCG CACTGAGCAA AAAAGCATGG CCTGGCGTGT GGACTAACTC GGTTTGTGGG
 301 CACCCACAAC TGGGAGAAAG CAACGAAGAC GCAGTGATCC GCCGTTGCCG TTATGAGCTT
 361 GGCGTGGAAA TTACGCCTCC TGAATCTATC TATCCTGACT TTCGCTACCG CGCCACCGAT
 421 CCGAGTGGCA TTGTGAAAAA TGAAGTGTGT CCGGTATTTG CCGCACGCAC CACTAGTGCG
 481 TTACAGATCA ATGATGATGA AGTGATGGAT TATCAATGGT GTGATTTAGC AGATGTATTA
 541 CACGGTATTG ATGCCACGCC GTGGGCGTTC AGTCCGTGGA TGGTGATGCA GGCGACAAAT End Isopentyl Pyrophosphate Isomerase—————|
 601 CGCGAAGCCA AAAAGCATT ATCTGCATTT ACCCAGCTTA ATAACCCGG GGATCCTCTA RBS         |—> Start Acetoacetyl-CoA Thiolaase
 661 GAGTCGACTA GGAGGAATAT AAAATGAAAA ATTGTGTCAT CGTCAGTGCG GTACGTACTG
 721 CTATCGGTAG TTTTAACGGT TCACTCGCTT CCACCAGCGC CATCGACCTG GGGGCGACAG
 781 TAATTAAAGC CGCCATTGAA CGTGCAAAAA TCGATTCACA ACACGTTGAT GAAGTGATTA
 841 TGGGTTACGT GTTACAAGCC GGGCTGGGGC AAAATCCGGC GCGTCAGGCA CTGTTAAAAA
 901 GCGGGCTGGC AGAAACGGTG TGCGGATTCA CGGTCAATAA AGTATGTGGT TCGGGTCTTA
 961 AAAGTGTGGC GCTTGCCGCC CAGGCCATTC AGGCAGGTCA GGCGCAGAGC ATTGTGGCGG
1021 GGGGTATGGA AAATATGAGT TTAGCCCCCT ACTTACTCGA TGCAAAAGCA CGCTCTGGTT
1081 ATCGTCTTGG AGACGGACAG GTTTATGACG TAATCCTGCG CGATGGCCTG ATGTGCGCCA
1141 CCCATGGTTA TCATATGGGG ATTACCGCCG AAAACGTGGC TAAAGAGTAC GGAATTACCC
```

```
1201 GTGAAATGCA GGATGAACTG GCGCTACATT CACAGCGTAA AGCGGCAGCC GCAATTGAGT
1261 CCGGTGCTTT TACAGCCGAA ATCGTCCCGG TAAATGTTGT CACTCGAAAG AAAACCTTCG
1321 TCTTCAGTCA AGACGAATTC CCGAAAGCGA ATTCAACGGC TGAAGCGTTA GGTGCATTGC
1381 GCCCGGCCTT CGATAAAGCA GGAACAGTCA CCGCTGGGAA CGCGTCTGGT ATTAACGACG
1441 GTGCTGCCGC TCTGGTGATT ATGGAAGAAT CTGCGGCGCT GGCAGCAGGC CTTACCCCCC

1501 TGGCTCGCAT TAAAAGTTAT GCCAGCGGTG GCGTGCCCCC CGCATTGATG GGTATGGGGC
1561 CAGTACCTGC CACGCAAAAA GCGTTACAAC TGGCGGGGCT GCAACTGGCG GATATTGATC
1621 TCATTGAGGC TAATGAAGCA TTTGCTGCAC AGTTCCTTGC CGTTGGGAAA AACCTGGGCT
1681 TTGATTCTGA GAAAGTGAAT GTCAACGGCG GGGCCATCGC GCAGGCACGC GATAAAACGC
1741 CCAGTGGTGC TCGTATTCTG GTCACACTAT TACATGCCAT GCAGGCACGC GATAAAACGC
1801 TGGGGCTGGC AACACTGTGC ATTGGCGGCG GTCAGGGAAT TGCGATGGTG ATTGAACGGT
Stop Acetoacetyl-CoA
Thiolase─────▶|             |────▶ Start HMG-CoA Synthase
1861 TGAATTAAGG AGGACAGCTA AATGAAACTC TCAACTAAAC TTTGTTGGTG TGGTATTAAA
1921 GGAAGACTTA GGCCGCAAAA GCAACAACAA TTACACAATA CAAACTTGCA AATGACTGAA
1981 CTAAAAAAAC AAAAGACCGC TGAACAAAAA ACCAGACCTC AAAATGTCGG TATTAAAGGT
2041 ATCCAAATTT ACATCCCAAC TCAATGTGTC AACCAATCTG AGCTAGAGAA ATTTGATGGC
2101 GTTTCTCAAG GTAAATACAC AATTGGTCTG GGCCAAACCA ACATGTCTTT TGTCAATGAC
2161 AGAGAAGATA TCTACTCGAT GTCCCTAACT GTTTTGTCTA AGTTGATCAA GAGTTACAAC
2221 ATCGACACCA ACAAAATTGG TAGATTAGAA GTCGGTACTG AAACTCTGAT TGACAAGTCC 2281 AAGTCTGTCA AGTCTGTCTT GATGCAATTG TTTGGTGAAA ACACTGACGT CGAAGGTATT
2341 GACACGCTTA ATGCCTGTTA CGGTGGTACC AACGCGTTGT TCAACTCTTT GAACTGGATT
2401 GAATCTAACG CATGGGATGG TAGAGACGCC ATTGTAGTTT GCGGTGATAT TGCCATCTAC
2461 GATAAGGGTG CCGCAAGACC AACCGGTGGT GCCGGTACTG TTGCTATGTG GATCGGTCCT
2521 GATGCTCCAA TTGTATTTGA CTCTGTAAGA GCTTCTTACA TGGAACACGC CTACGATTTT
2581 TACAAGCCAG ATTTCACCAG CGAATATCCT TACGTCGATG GTCATTTTTC ATTAACTTGT
2641 TACGTCAAGG CTCTTGATCA AGTTTACAAG AGTTATTCCA AGAAGGCTAT TTCTAAAGGG
2701 TTGGTTAGCG ATCCCGCTGG TTCGGATGCT TTGAACGTTT TGAAATATTT CGACTACAAC
2761 GTTTTCCATG TTCCAACCTG TAAATTGGTC ACAAAATCAT ACGGTAGATT ACTATATAAC 2821 GATTTCAGAG CCAATCCTCA ATTGTTCCCA GAAGTTGACG CCGAATTAGC TACTCGCGAT
2881 TATGACGAAT CTTTAACCGA TAAGAACATT GAAAAAACTT TTGTTAATGT TGCTAAGCCA
2941 TTCCACAAAG AGAGAGTTGC CCAATCTTTG ATTGTTCCAA CAAACACAGG TAACATGTAC
3001 ACCGCATCTG TTTATGCCGC CTTTGCATCT CTATTAAACT ATGTTGGATC TGACGACTTA
3061 CAAGGCAAGC GTGTTGGTTT ATTTTCTTAC GGTTCCGGTT TAGCTGCATC TCTATATTCT
3121 TGCAAAATTG TTGGTGACGT CCAACATATT ATCAAGGAAT TAGATATTAC TAACAAATTA
3181 GCCAAGAGAA TCACCGAAAC TCCAAAGGAT TACGAAGCTG CCATCGAATT GAGAGAAAAT
3241 GCCCATTTGA AGAAGAACTT CAAACCTCAA GGTTCCATTG AGCATTTGCA AAGTGGTGTT Stop HMG-CoA sythase────▶|
3301 TACTACTTGA CCAACATCGA TGACAAATTT AGAAGATCTT ACGATGTTAA AAATAAGGA

|────▶ Start Truncated HMG-CoA Reductase
3361 GGATTACACT ATGGTTTTAA CCAATAAAAC AGTCATTTCT GGATCGAAAG TCAAAGTTT
3421 ATCATCTGCG CAATCGAGCT CATCAGGACC TTCATCATCT AGTGAGGAAG ATGATTCCCG
3481 CGATATTGAA AGCTTGGATA AGAAAATACG TCCTTTAGAA GAATTAGAAG CATTATTAAG
3541 TAGTGGAAAT ACAAAACAAT TGAAGAACAA AGAGGTCGCT GCCTTGGTTA TTCACGGTAA
3601 GTTACCTTTG TACGCTTTGG AGAAAAAATT AGGTGATACT ACGAGAGCGG TTGCGGTACG
3661 TAGGAAGGCT CTTTCAATTT TGGCAGAAGC TCCTGTATTA GCATCTGATC GTTTACCATA
3721 TAAAAATTAT GACTACGACC GCGTATTTGG CGCTTGTTGT GAAAATGTTA TAGGTTACAT 3781 GCCTTTGCCC GTTGGTGTTA TAGGCCCCTT GGTTATCGAT GGTACATCTT ATCATATACC
3841 AATGGCAACT ACAGAGGGTT GTTTGGTAGC TTCTGCCATG CGTGGCTGTA AGGCAATCAA
3901 TGCTGGCGGT GGTGCAACAA CTGTTTTAAC TAAGGATGGT ATGACAAGAG CCCAGTAGT
3961 CCGTTTCCCA ACTTTGAAAA GATCTGGTGC CTGTAAGATA TGGTTAGACT CAGAAGAGGG
4021 ACAAAACGCA ATTAAAAAAG CTTTTAACTC TACATCAAGA TTTGCACGTC TGCAACATAT
4081 TCAAACTTGT CTAGCAGGAG ATTTACTCTT CATGAGATTT AGAACAACTA CTGGTGACGC
4141 AATGGGTATG AATATGATTT CTAAAGGTGT CGAATACTCA TTAAAGCAAA TGGTAGAAGA
4201 GTATGGCTGG GAAGATATGG AGGTTGTCTC CGTTTCTGGT AACTACTGTA CCGACAAAAA
4261 ACCAGCTGCC ATCAACTGGA TCGAAGGTCG TGGTAAGAGT GTCGTCGCAG AAGCTACTAT
4321 TCCTGGTGAT GTTGTCAGAA AAGTGTTAAA AAGTGATGTT CCGCATTGG TTGAGTTGAA 4381 CATTGCTAAG AATTTGGTTG GATCTGCAAT GGCTGGGTCT GTTGGTGGAT TAACGCACA
4441 TGCAGCTAAT TTAGTGACAG CTGTTTTCTT GGCATTAGGA CAAGATCCTG CACAAAATGT
4501 TGAAAGTTCC AACTGTATAA CATTGATGAA AGAAGTGGAC GGTGATTTGA GAATTTCCGT
4561 ATCCATGCCA TCCATCGAAG TAGGTACCAT CGGTGGTGGT ACTGTTCTAG AACCACAAGG
4621 TGCCATGCTTG GACTTATTAG TAGGTACCAT CGGTGGTGGT ACTGTTCTAG AACCACAAGG
4681 ACGTCAATTA GCAAGAATAG TTGCCTGTGC CGTCTTGGCA GGTGAATTAT CCTTATGTGC
4741 TGCCCTAGCA GCCGGCCATT TGGTTCAAAG TCATATGACC CACAACAGGA AACCTGCTGA
4801 ACCAACAAAA CCTAACAATT TGGACGCCAC TGATATAAAT CGTTTGAAAG ATGGGTCCGT
```

SEQUENCE LISTING
Assignment of SEQ ID NOS

```
        Stop Truncated
        HMG-CoA Reductase───▶|                    RBS          |──▶  Start
4861  CACCTGCATT AAATCCTAAG TCGACCTGCA GTAGGAGGAA TTAACCATGT CATTACCGTT Mevalonate Kinase
4921  CTTAACTTCT GCACCGGGAA AGGTTATTAT TTTTGGTGAA CACTCTGCTG TGTACAACAA
4981  GCCTGCCGTC GCTGCTAGTG TGTCTGCGTT GAGAACCTAC CTGCTAATAA GCGAGTCATC
5041  TGCACCAGAT ACTATTGAAT GGACTTCCC GGACATTAGC TTTAATCATA AGTGGTCCAT 5101  CAATGATTTC AATGCCATCA CCGAGGATCA AGTAAACTCC CAAAAATTGG CCAAGGCTCA
5161  ACAAGCCACC GATGGCTTGT CTCAGGAACT CGTTAGTCTT TTGGATCGT TGTTAGCTCA
5221  ACTATCCGAA TCCTTCCACT ACCATGCAGC GTTTTGTTTC CTGTATATGT TTGTTTGCCT
5281  ATGCCCCCAT GCCAAGAATA TTAAGTTTTC TTTAAAGTCT ACTTTACCCA TCGGTGCTGG
5341  GTTGGGCTCA AGCGCCTCTA TTTCTGTATC ACTGGCCTTA GCTATGGCCT ACTTGGGGGG
5401  GTTAATAGGA TCTAATGACT TGGAAAAGCT GTCAGAAAAC GATAAGCATA TAGTGAATCA
5461  ATGGGCCTTC ATAGGTGAAA AGTGTATTCA CGGTACCCCT TCAGGAATAG ATAACGCTGT
5521  GGCCACTTAT GGTAATGCCC TGCTATTTGA AAAAGACTCA CATAATGGAA CAATAAACAC 5581  AAACAATTTT AAGTTCTTAG ATGATTTCCC AGCCATTCCA ATGATCCTAA CCTATACTAG
5641  AATTCCAAGG TCTACAAAAG ATCTTGTTGC TCGCGTTCGT GTGTTGGTCA CCGAGAAATT
5701  TCCTGAAGTT ATGAAGCCAA TTCTAGATGC CATGGGTGAA TGTGCCCTAC AAGGCTTAGA
5761  TGAACTGTAT GAACAACTAT TGGAATTGAT AAGAATAAAT CATGGACTGC TTGTCTCAAT
5821  TGAACTGTAT GAACAACTAT TGGAATTGAT AAGAATAAAT CATGGACTGC TTGTCTCAAT
5881  CGGTGTTTCT CATCCTGGAT TAGAACTTAT TAAAAATCTG AGCGATGATT TGAGAATTGG
5941  CTCCACAAAA CTTACCGGTG CTGGTGGCGG CGGTTGCTCT TTGACTTTGT TACGAAGAGA
6001  CATTACTGCA GAGCAAATTG ACAGCTTCAA AAAGAAATTG CAAGATGATT TTAGTTACGA
6061  GACATTTGAA ACAGACTTGG GTGGGACTGG CTGCTGTTTG TTAAGCGCAA AAAATTTGAA
6121  TAAAGATCTT AAAATCAAAT CCCTAGTATT CCAATTATTT GAAAATAAAA CTACCACAAA Stop Mevalonate Kinase
                                                                        ───▶|
6181  GCAACAAATT GACGATCTAT TATTGCCAGG AAACACGAAT TTACCATGGA CTTCATAGGA
                                                                        RBS

|──▶ Start Phosphomevalonate Kinase
6241  GGCAGATCAA ATGTCAGAGT TGAGAGCCTT CAGTGCCCCA GGGAAAGCGT TACTAGCTGG
6301  TGGATATTTA GTTTTAGATA CAAAATATGA AGCATTTGTA GTCGGATTAT CGGCAAGAAT
6361  GCATGCTGTA GCCCATCCTT ACGGTTCATT GCAAGGGTCT GATAAGTTTG AAGTGCGTGT
6421  GAAAAGTAAA CAATTTAAAG ATGGGGAGTG GCTGTACCAT ATAAGTCCTA AAAGTGGCTT
6481  CATTCCTGTT TCGATAGGCG GATCTAAGAA CCCTTTCATT GAAAAAGTTA TCGCTAACGT
6541  ATTTAGCTAC TTTAAACCTA ACATGGACGA CTACTGCAAT AGAACTTGT TCGTTATTGA 6601  TATTTTCTCT GATGATGCCT ACCATTCTCA GGAGGATAGC GTTACCGAAC ATCGTGGCAA
6661  CAGAAGATTG AGTTTTCATT CGCACAGAAT TGAAGAAGTT CCCAAAACAG GGCTGGGCTC
6721  CTCGGCAGGT TTAGTCACAG TTTTAACTAC AGCTTTGGCC TCCTTTTTTG TATCGGACCT
6781  GGAAAATAAT GTAGACAAAT ATAGAGAAGT TATTCATAAT TTAGCACAAG TTGCTCATTG
6841  TCAAGCTCAG GGTAAAATTG AAGCGGGTT TGATGTAGCG GCGGCAGCAT ATGGATCTAT
6901  CAGATATAGA AGATTCCCAC CCGCATTAAT CTCTAATTTG CCAGATATTG GAAGTGCTAC
6961  TTACGGCAGT AAACTGGCGC ATTTGGTTGA TGAAGAAGAC TGGAATATTA CGATTAAAAG 7021  TAACCATTTA CCTTCGGGAT TAACTTTATG GATGGGCGAT ATTAAGAATG GTTCAGAAAC
7081  AGTAAAACTG GTCCAGAAGG TAAAAAATTG GTATGATTCG CATATGCCAG AAAGCTTGAA
7141  AATATATACA GAACTCGATC ATGCAAATTC TAGATTTATG GATGGACTAT CTAAACTAGA
7201  TCGCTTACAC GAGACTCATG ACGATTACAG CGATCAGATA TTTGAGTCTC TTGAGAGGAA
7261  TGACTGTACC TGTCAAAAGT ATCCTGAAAT CACAGAAGTT AGAGATGCAG TTGCCACAAT
7321  TAGACGTTCC TTTAGAAAAA TAACTAAAGA ATCTGGTGCC GATATCGAAC CTCCCGTACA
7381  AACTAGCTTA TTGGATGATT GCCAGACCTT AAAAGGAGTT CTTACTTGCT TAATACCTGG
7441  TGCTGGTGGT TATGACGCCA TTGCAGTGAT TACTAAGCAA GATGTTGATC TTAGGGCTCA
7501  AACCGCTAAT GACAAAAGAT TTTCTAAGGT TCAATGGCTG GATGTAACTC AGGCTGACTG Stop Phosphomevalonate Kinase───▶|              |──▶
7561  GGGTGTTAGG AAAGAAAAAG ATCCGGAAAC TTATCTTGAT AAATAGGAGG TAATACTCAT
                                                               RBS ───▶Start Mevalonate Pyrophosphate Decarboxylase
7621  GACCGTTTAC ACAGCATCCG TTACCGCACC CGTCAACATC GCAACCCTTA AGTATTGGGG
7681  GAAAAGGGAC ACGAAGTTGA ATCTGCCCAC CAATTCGTCC ATATCAGTGA CTTTATCGCA
7741  AGATGACCTC AGAACGTTGA CCTCTGCGGC TACTGCACCT GAGTTTGAAC GCGACACTTT
7801  GTGGTTAAAT GGAGAACCAC ACAGCATCGA CAATGAAAGA ACTCAAAATT GTCTGCGCGA
7861  CCTACGCCAA TTAAGAAAGG AAATGGAATC GAAGGACGCC TCATTGCCCA CATTATCTCA
7921  ATGGAAACTC CACATTGTCT CCGAAAATAA CTTTCCTACA GCAGCTGGTT TAGCTTCCTC 7981  CGCTGCTGGC TTTGCTGCAT TGGTCTCTGC AATTGCTAAG TTATACCAAT TACCACAGTC
8041  AACTTCAGAA ATATCTAGAA TAGCAAGAAA GGGGTCTGGT TCAGCTTGTA GATCGTTGTT
8101  TGGCGGATAC GTGGCCTGGG AAATGGGAAA AGCTGAAGAT GGTCATGATT CCATGGCAGT
8161  ACAAATCGCA GACAGCTCTG ACTGGCCTCA GATGAAAGCT TGTGTCCTAG TTGTCAGCGA
8221  TATTAAAAAG GATGTGAGTT CCACTCAGGG TATGCAATTG ACCGTGGCAA CCTCCGAACT
8281  ATTTAAAGAA AGAATTGAAC ATGTCGTACC AAAGAGATTT GAAGTCATGC GTAAAGCCAT
```

```
8341 TGTTGAAAAA GATTTCGCCA CCTTTCGAAA GGAAACAATG ATGGATTCCA ACTCTTTCCA
8401 TGCCACATGT TTGGACTCTT TCCCTCCAAT ATTCTACATG AATGACACTT CCAAGCGTAT
8461 CATCAGTTGG TGCCACACCA TTAATCAGTT TTACGGAGAA ACAATCGTTG CATACACGTT
8521 TGATGCAGGT CCAAATGCTG TGTTGTACTA CTTAGCTGAA AATGAGTCGA AACTCTTTGC
8581 ATTTATCTAT AAATTGTTTG GCTCTGTTCC TGGATGGGAC AAGAAATTTA CTACTGAGCA
8641 GCTTGAGGCT TTCAACCATC AATTTGAATC ATCTAACTTT ACTGCACGTG AATTGGATCT
8701 TGAGTTGCAA AAGGATGTTG CCAGAGTGAT TTTAACTCAA GTCGGTTCAG GCCCACAAGA
```

Stop Mevalonate Pyrophosphate Decarboxylase ⟶|

```
8761 AACAAACGAA TCTTTGATTG ACGCAAAGAC TGGTCTACCA AAGGAATAAC TGCAGGCATG
```

|⟶ Strong ribosomal rrnB terminators

```
8821 CAAGCTTGGC TGTTTTGGCG GATGAGAGAA GATTTTCAGC CTGATACAGA TTAAATCAGA
8881 ACGCAGAAGC GGTCTGATAA AACAGAATTT GCCTGGCGGC AGTAGCGCGG TGGTCCCACC
8941 TGACCCCATG CCGAACTCAG AAGTGAAACG CCGTAGCGCC GATGGTAGTG TGGGGTGTCC
9001 CCATGCGAGA GTAGGGAACT GCCAGGCATC AAATAAAACG AAAGGCTCAG TCGAAAGACT
9061 GGGCCTTTCG TTTTATCTGT TGTTTGTCGG TGAACGCTCT CCTGAGTAGG ACAAATCCGC
9121 CGGGAGCGGA TTTGAACGTT GCGAAGCAAC GGCCCGGAGG GTGGCGGGCA GGACGCCCGC
9181 CATAAACTGC CAGGCATCAA ATTAAGCAGA AGGCCATCCT GACGGATGGC CTTTTTGCGT
9241 TTCTACAAAC TCT
```

SEQ ID NO 8 "MEVT" operon nucleotide sequence
    P_BAD Promoter

```
   1 GACGCTTTTT ATCGCAACTC TCTACTGTTT CTCCATACCC GTTTTTTTGG GCTAGCAGGA
```

RBS        |⟶

```
  61 GGAATTCACC ATGGTACCCG GGATCCTCT AGAGTCGACT AGGAGGAATA TAAAATGAAA
```

Start Acetoacetyl-CoA thiolase

```
 121 AATTGTGTCA TCGTCAGTGC GGTACGTACT GCTATCGGTA GTTTTAACGG TTCACTCGCT

181 TCCACCAGCG CCATCGACCT GGGGGCGACA GTAATTAAAG CCGCCATTGA ACGTGCAAAA
 241 ATCGATTCAC AACACGTTGA TGAAGTGATT ATGGGTAACG TGTTACAAGC CGGGCTGGGG
 301 CAAAATCCGG CGCGTCAGGC ACTGTTAAAA AGCGGGCTGG CAGAAACGGT GTGCGGATTC
 361 ACGGTCAATA AGTATGTGG TTCGGGTCTT AAAAGTGTGG CGCTTGCCGC CCAGGCCATT
 421 CAGGCAGGTC AGGCGCAGAG CATTGTGGCG GGGGGTATGG AAAATATGAG TTTAGCCCCC
 481 TACTTACTCG ATGCAAAAGC ACGCTCTGGT TATCGTCTTG GAGACGGACA GGTTTATGAC
 541 GTAATCCTGC GCGATGGCCT GATGTGCGCC ACCCATGGTT ATCATATGGG GATTACCGCC

601 GAAAACGTGG CTAAAGAGTA CGGAATTACC CGTGAAATGC AGGATGAACT GGCGCTACAT
 661 GAAAACGTGG CTAAAGAGTA CGGAATTACC CGTGAAATGC AGGATGAACT GGCGCTACAT
 721 GTAAATGTTG TCACTCGAAA GAAAACCTTC GTCTTCAGTC AAGACGAATT CCCGAAAGCG
 781 AATTCAACGG CTGAAGCGTT AGGTGCATTG CGCCCGGCCT TCGATAAAGC AGGAACAGTC
 841 ACCGCTGGGA ACGCGTCTGG TATTAACGAC GGTGCTGCCG CTCTGGTGAT TATGGAAGAA
 901 TCTGCGCGCG TGGCAGCAGG CCTTACCCCC CTGGCTCGCA TTAAAAGTTA TGCCAGCGGT
 961 GGCGTGCCCC CCGCATTGAT GGGTATGGGG CCAGTACCTG CCACGCAAAA AGCGTTACAA

1021 CTGGCGGGGC TGCAACTGGC GGATATTGAT CTGATTGAGG CTAATGAAGC ATTTGCTGCA
1081 CAGTTCCTTG CCGTTGGGAA AAACCTGGGC TTTGATTCTG AGAAAGTGAA TGTCAACGGC
1141 GGGGCCATCG CGCTCGGGCA TCCTATCGGT GCCAGTGGTG CTCGTATTCT GGTCACACTA
1201 TTACATGCCA TGCAGGCACG CGATAAAACG CTGGGGCTGG CAACACTGTG CATTGGCGGC
```

Stop Acetoacetyl-CoA Thiolase⟶|                |⟶ Start

```
1261 GGTCAGGGAA TTGCGATGGT GATTGAACGG TTGAATTAAG GAGGACAGCT AAATGAAACT
```
                                                                   RBS

HMG-CoA Synthase

```
1321 CTCAACTAAA CTTTGTTGGT GTGGTATTAA AGGAAGACTT AGGCCGCAAA AGCAACAACA
1381 ATTACACAAT ACAAACTTGC AAATGACTGA ACTAAAAAAA CAAAGACCG CTGAACAAAA
1441 AACCAGACCT CAAAATGTCG GTATTAAAGG TATCCAAATT TACATCCCAA CTCAATGTGT
1501 CAACCAATCT GAGCTAGAGA AATTTGATGG CGTTTCTCAA GGTAAATACA CAATTGGTCT
1561 GGGCCAAACC AACATGTCTT TTGTCAATGA CAGAGAAGAT ATCTACTCGA TGTCCCTAAC
1621 TGTTTTGTCT AAGTTGATCA AGAGTTACAA CATCGACACC AACAAATTG GTAGATTAGA
1681 AGTCGGTACT GAAACTCTGA TTGACAAGTC CAAGTCTGTC AAGTCTGTCT TGATGCAATT
```

```
1741 GTTTGGTGAA AACACTGACG TCGAAGGTAT TGACACGCTT AATGCCTGTT ACGGTGGTAC
1801 CAACGCGTTG TTCAACTCTT TGAACTGGAT TGAATCTAAG GCATGGGATG GTAGAGACGC
1861 CATTGTAGTT TGCGGTGATA TTGCCATCTA CGATAAGGGT GCCGCAAGAC CAACCGGTGG
1921 TGCCGGTACT GTTGCTATGT GGATCGGTCC TGATGCTCCA ATTGTATTTG ACTCTGTAAG
1981 AGCTTCTTAC ATGGAACACG CCTACGATTT TTACAAGCCA GATTTCACCA GCGAATATCC
2041 TTACGTCGAT GGTCATTTTT CATTAACTTG TTACGTCAAG GCTCTTGATC AAGTTTACAA
2101 GAGTTATTCC AAGAAGGCTA TTTCTAAAGG GTTGGTTAGC GATCCCGCTG GTTCGGATGC
2161 TTTGAACGTT TTGAAATATT TCGACTACAA CGTTTTCCAT GTTCCAACCT GTAAATTGGT
2221 CACAAAATCA TACGGTAGAT TACTATATAA CGATTTCAGA GCCAATCCTC AATTGTTCCC
2281 AGAAGTTGAC GCCGAATTAG CTACTCGCGA TTATGACGAA TCTTTAACCG ATAAGAACAT
2341 TGAAAAAACT TTTGTTAATG TTGCTAAGCC ATTCCACAAA GAGAGAGTTG CCCAATCTTT
2401 GATTGTTCCA ACAAACACAG GTAACATGTA CACCGCATCT GTTTATGCCG CCTTTGCATC
2461 TCTATTAAAC TATGTTGGAT CTGACGACTT ACAAGGCAAG CGTGTTGGTT TATTTTCTTA
2521 CGGTTCCGGT TTAGCTGCAT CTCTATATTC TTGCAAAATT GTTGGTGACG TCCAACATAT
2581 TATCAAGGAA TTAGATATTA CTAACAAATT AGCCAAGAGA ATCACCGAAA CTCCAAAGGA
2641 TTACGAAGCT GCCATCGAAT TGAGAGAAAA TGCCCATTTG AAGAAGAACT TCAAACCTCA
2701 AGGTTCCATT GAGCATTTGC AAAGTGGTGT TTACTACTTG ACCAACATCG ATGACAAATT
```

```
           Stop HMG-CoA synthase ──▶|                |──▶  Start Truncated
2761 TAGAAGATCT TACGATGTTA AAAAATAAGG AGGATTACAC TATGGTTTTA ACCAATAAAA
                                      RBS
```

HMG-CoA reductase
```
2821 CAGTCATTTC TGGATCGAAA GTCAAAAGTT TATCATCTGC GCAATCGAGC TCATCAGGAC
2881 CTTCATCATC TAGTGAGGAA GATGATTCCC GCGATATTGA AAGCTTGGAT AAGAAAAATAC
2941 GTCCTTTAGA AGAATTAGAA GCATTATTAA GTAGTGGAAA TACAAAACAA TTGAAGAACA
3001 AAGAGGTCGC TGCCTTGGTT ATTCACGGTA AGTTACCTTT GTACGCTTTG GAGAAAAAAT
3061 TAGGTGATAC TACGAGAGCG GTTGCGGTAC GTAGGAAGGC TCTTTCAATT TTGGCAGAAG
3121 CTCCTGTATT AGCATCTGAT CGTTTACCAT ATAAAAATTA TGACTACGAC CGCGTATTTG
3181 GCGCTTGTTG TGAAAATGTT ATAGGTTACA TGCCTTTGCC CGTTGGTGTT ATAGGCCCCT
3241 TGGTTATCGA TGGTACATCT TATCATATAC CAATGGCAAC TACAGAGGGT TGTTTGGTAG
3301 CTTCTGCCAT GCGTGGCTGT AAGGCAATCA ATGCTGGCGG TGGTGCAACA ACTGTTTTAA
3361 CTAAGGATGG TATGACAAGA GGCCCAGTAG TCCGTTTCCC AACTTTGAAA AGATCTGGTG
3421 CCTGTAAGAT ATGGTTAGAC TCAGAAGAGG GACAAAACGC AATTAAAAAA GCTTTTAACT
3481 CTACATCAAG ATTTGCACGT CTGCAACATA TTCAAACTTG TCTAGCAGGA GATTTACTCT
3541 TCATGAGATT TAGAACAACT ACTGGTGACG CAATGGGTAT GAATATGATT TCTAAAGGTG
3601 TCGAATACTC ATTAAAGCAA ATGGTAGAAG AGTATGGCTG GGAAGATATG GAGGTTGTCT
3661 CCGTTTCTGG TAACTACTGT ACCGACAAAA AACCAGCTGC CATCAACTGG ATCGAAGGTC
3721 GTGGTAAGAG TGTCGTCGCA GAAGCTACTA TTCCTGGTGA TGTTGTCAGA AAAGTGTTAA
3781 AAAGTGATGT TTCCGCATTG GTTGAGTTGA ACATTGCTAA GAATTTGGTT GGATCTGCAA
3841 TGGCTGGGTC TGTTGGTGGA TTTAACGCAC ATGCAGCTAA TTTAGTGACA GCTGTTTTCT
3901 TGGCATTAGG ACAAGATCCT GCACAAAATG TTGAAAGTTC CAACTGTATA ACATTGATGA
3961 AAGAAGTGGA CGGTGATTTG AGAATTTCCG TATCCATGCC ATCCATCGAA GTAGGTACCA
3901 TGGCATTAGG ACAAGATCCT GCACAAAATG TTGAAAGTTC CAACTGTATA ACATTGATGA
3961 AAGAAGTGGA CGGTGATTTG AGAATTTCCG TATCCATGCC ATCCATCGAA GTAGGTACCA
4021 TCGGTGGTGG TACTGTTCTA GAACCACAAG GTGCCATGTT GGACTTATTA GGTGTAAGAG
4081 GCCCGCATGC TACCCGCTCC GGTACCAACG CACGTCAATT AGCAAGAATA GTTGCCTGTG
4141 CCGTCTTGGC AGGTGAATTA TCCTTATGTG CTGCCCTAGC AGCCGGCCAT TTGGTTCAAA
4201 GTCATATGAC CCACAACAGG AAACCTGCTG AACCAACAAA ACCTAACAAT TTGGACGCCA
```

```
                  Stop Truncated HMG-CoA Reductase ──▶|
4261 CTGATATAAA TCGTTTGAAA GATGGGTCCG TCACCTGCAT TAAATCCTAA GTCGACCTGC
```

```
           |──▶ Strong ribosomal rrnB terminators
4321 AGGCATGCAA GCTTGGCTGT TTTGGCGGAT GAGAGAAGAT TTTCAGCCTG ATACAGATTA
4381 AATCAGAACG CAGAAGCGGT CTGATAAAAC AGAATTTGCC TGGCGGCAGT AGCGCGGTGG
```

```
4441 TCCCACCTGA CCCCATGCCG AACTCAGAAG TGAAACGCCG TAGCGCCGAT GGTAGTGTGG
4501 GGTCTCCCCA TGCGAGAGTA GGGAACTGCC AGGCATCAAA TAAAACGAAA GGCTCAGTCG
4561 AAAGACTGGG CCTTTCGTTT TATCTGTTGT TTGTCGGTGA ACGCTCTCCT GAGTAGGACA
4621 AATCCGCCGG GAGCGGATTT GAACGTTGCG AAGCAACGGC CCGGAGGGTG GCGGGCAGGA
4741 TTTGCGTTTC TACAAACTCT
```

SEQ ID NO 9 "MEVB" operon nucleotide sequence

```
     Lac Promoter
   1 GCGCAACGCA ATTAATGTGA GTTAGCTCAC TCATTAGGCA CCCCAGGCTT TACACTTTAT
  61 GCTTCCGGCT CGTATGTTGT GTGGAATTGT GAGCGGATAA CAATTTCACA CAGGAAACAG
 121 CTATGACCAT GATTACGCCA AGCGCGCAAT TAACCCTCAC TAAAGGGAAC AAAAGCTGGG
 181 TACCGGGCCC CCCCTCGAGG TCGACGGTAT CGATAAGCTT GATATCGAAT TCCTGCAGTA
```

SEQUENCE LISTING
Assignment of SEQ ID NOS

```
        RBS           ┌─► Start Mevalonate Kinase
 241 GGAGGAATTA ACCATGTCAT TACCGTTCTT AACTTCTGCA CCGGGAAAGG TTATTATTTT 301 TGGTGAACAC TCTGCTGTGT ACAACAAGCC TGCCGTCGCT GCTAGTGTGT CTGCGTTGAG
 361 AACCTACCTG CTAATAAGCG AGTCATCTGC ACCAGATACT ATTGAATTGG ACTTCCCGGA
 421 CATTAGCTTT AATCATAAGT GGTCCATCAA TGATTTCAAT GCCATCACCG AGGATCAAGT
 481 AAACTCCCAA AAATTGGCCA AGGCTCAACA AGCCACCGAT GGCTTGTCTC AGGAACTCGT
 541 TAGTCTTTTG GATCCGTTGT TAGCTCAACT ATCCGAATCC TTCCACTACC ATGCAGCGTT
 601 TTGTTTCCTG TATATGTTTG TTTGCCTATG CCCCCATGCC AAGAATATTA AGTTTTCTTT
 661 AAAGTCTACT TTACCCATCG GTGCTGGGTT GGGCTCAAGC GCCTCTATTT CTGTATCACT
 721 GGCCTTAGCT ATGGCCTACT TGGGGGGGTT AATAGGATCT AATGACTTGG AAAAGCTGTC
 781 AGAAAACGAT AAGCATATAG TGAATCAATG GGCCTTCATA GGTGAAAAGT GTATTCACGG
 841 TACCCCTTCA GGAATAGATA ACGCTGTGGC CACTTATGGT AATGCCCTGC TATTTGAAAA
 901 AGACTCACAT AATGGAACAA TAAACACAAA CAATTTTAAG TTCTTAGATG ATTTCCCAGC
 961 CATTCCAATG ATCCTAACCT ATACTAGAAT TCCAAGGTCT ACAAAAGATC TTGTTGCTCG
1021 CGTTCGTGTG TTGGTCACCG AGAAATTTCC TGAAGTTATG AAGCCAATTC TAGATGCCAT
1081 GGGTGAATGT GCCCTACAAG GCTTAGAGAT CATGACTAGG TTAAGTAAAT GTAAAGGCAC
1141 CGATGACGAG GCTGTAGAAA CTAATAATGA ACTGTATGAA CAACTATTGG AATTGATAAG 1201 AATAAATCAT GGACTGCTTG TCTCAATCGG TGTTTCTCAT CCTGGATTAG AACTTATTAA
1261 AAATCTGAGC GATGATTTGA GAATTGGCTC CACAAAACTT ACCGGTGCTG GTGGCGGCGG
1321 TTGCTCTTTG ACTTTGTTAC GAAGAGACAT TACTCAAGAG CAAATTGACA GCTTCAAAAA
1381 GAAATTGCAA GATGATTTTA GTTACGAGAC ATTTGAAACA GACTTGGGTG GGACTGGCTG
1441 CTGTTTGTTA AGCGCAAAAA ATTTGAATAA AGACCTTAAA ATCAAATCCC TAGTATTCCA
1501 ATTATTTGAA AATAAAACTA CCACAAAGCA ACAAATTGAC GATCTATTAT TGCCAGGAAA Stop Mevalonate Kinase──►│              ┌──► Start Phosphomevalonate
1561 CACGAATTTA CCATGGACTT CATAGGAGGC AGATCAAATG TCAGAGTTGA GAGCCTTCAG
                                 RBS Kinase
1621 TGCCCCAGGG AAAGCGTTAC TAGCTGGTGG ATATTTAGTT TTAGATACAA AATATGAAGC
1681 ATTTGTAGTC GGATTATCGG CAAGAATGCA TGCTGTAGCC CATCCTTACG GTTCATTGCA
1741 AGGGTCTGAT AAGTTTGAAG TGCGTGTGAA AGTAAACAA TTTAAAGATG GGGAGTGGCT
1801 GTACCATATA AGTCCTAAAA GTGGCTTCAT TCCTGTTTCG ATAGGCGGAT CTAAGAACCC
1861 TTTCATTGAA AAAGTTATCG CTAACGTATT TAGCTACTTT AAACCTAACA TGGACGACTA
1921 CTGCAATAGA AACTTGTTCG TTATTGATAT TTTCTCTGAT GATGCCTACC ATTCTCAGGA
1981 GGATAGCGTT ACCGAACATC GTGGCAACAG AAGATTGAGT TTTCATTCGC ACAGAATTGA
2041 AGAAGTTCCC AAAACAGGGC TGGGCTCCTC GGCAGGTTTA GTCACAGTTT TAACTACAGC
2101 TTTGGCCTCC TTTTTTGTAT CGGACCTGGA AAATAATGTA GACAAATATA GAGAAGTTAT
2161 TCATAATTTA GCACAAGTTG CTCATTGTCA AGCTCAGGGT AAAATTGGTA GCGGGTTTGA
2221 TGTAGCGGCG GCAGCAATG GATCTATCAG ATATAGAAGA TTCCCACCCG CATTAATCTC
2281 TAATTTGCCA GATATTGGAA GTGCTACTTA CGGCAGTAAA CTGGCGCATT TGGTTGATGA
2341 AGAAGACTGG AATATTACGA TTAAAAGTAA CCATTTACCT TCGGGATTAA CTTTATGGAT
2401 GGGCGATATT AAGAATGGTT CAGAAACAGT AAAACTGGTC CAGAAGGTAA AAATTGGTA
2461 TGATTCGCAT ATGCCAGAAA GCTTGAAAAT ATATACAGAA CTCGATCATG CAAATTCTAG
2521 ATTTATGGAT GGACTATCTA AACTAGATCG CTTACACGAG ACTCATGACG ATTACAGCGA
2581 TCAGATATTT GAGTCTCTTG AGAGGAATGA CTGTACCTGT CAAAAGTATC CTGAAATCAC
2641 AGAAGTTAGA GATGCAGTTG CCACAATTAG ACGTTCCTTT AGAAAAATAA CTAAAGAATC
2701 TGGTGCCGAT ATCGAACCTC CCGTACAAAC TAGCTTATTG GATGATTGCC AGACCTTAAA
2761 AGGAGTTCTT ACTTGCTTAA TACCTGGTGC TGGTGGTTAT GACGCCATTG CAGTGATTAC
2821 TAAGCAAGAT GTTGATCTTA GGGCTCAAAC CGCTAATGAC AAAAGATTTT CTAAGGTTCA Stop Phosphomevalonate
2881 ATGGCTGGAT GTAACTCAGG CTGACTGGGG TGCCAGGAAA GAAAAAGATC CGGAAACTTA Kinase ──────►│              ┌──► Start Mevalonate Pyrophosphate
2941 TCTTGATAAA TAGGAGGTAA TACTCATGAC CGTTTACACA GCATCCGTTA CCGCACCCGT
                    RBS Decarbozylase
3001 CAACATCGCA ACCCTTAAGT ATTGGGGGAA AAGGGACACG AAGTTGAATC TGCCCACCAA
3061 TTCGTCCATA TCAGTGACTT TATCGCAAGA TGACCTCAGA ACGTTGACCT CTGCGGCTAC
3121 TGCACCTGAG TTTAACGCG ACACTTTGTG GTTAAATGGA GAACCACACA GCATCGACAA
3181 TGAAAGAACT CAAAATTGTC TGCGCGACCT ACGCCAATTA AGAAGGAAA TGGAATCGAA
3241 GGACGCCTCA TTGCCCACAT TATCTCAATG GAAACTCCAC ATTGTCTCCG AAAATAACTT
3301 TCCTACAGCA GCTGGTTTAG CTTCCTCCGC TGCTGGCTTT GCTGCATTGG TCTCTGCAAT 3361 TGCTAAGTTA TACCAATTAC CACAGTCAAC TTCAGAAATA TCTAGAATAC CAAGAAAGGG
3421 GTCTGGTTCA GCTTGTAGAT CGTTGTTTGG CGGATACGTG GCCTGGGAAA TGGGAAAAGC
3481 TGAAGATGGT CATGATTCCA TGGCAGTACA AATCGCAGAC TGCTCTGACT GGCCTCAGAT
3541 GAAAGCTTGT GTCCTAGTTG TCAGCGATAT TAAAAAGGAT GTGAGTTCCA CTCAGGGTAT
3601 GCAATTGACC GTGGCAACCT CCGAACTATT TAAAGAAAGA ATTGAACATG TCGTACCAAA
```

```
3661 GAGATTTGAA GTCATGCGTA AAGCCATTGT TGAAAAAGAT TTCGCCACCT TTGCAAAGGA
3721 AACAATGATG GATTCCAACT CTTTCCATGC CACATGTTTG CACTCTTTCC CTCCAATATT
3781 CTACATGAAT GACACTTCCA AGCGTATCAT CAGTTGGTGC CACACCATTA ATCAGTTTTA
3841 CGGAGAAACA ATCGTTGCAT ACACGTTTGA TGCAGGTCCA AATGCTGTGT TGTACTACTT
3901 AGCTGAAAAT GAGTCGAAAC TCTTTGCATT TATCTATAAA TTGTTTGGCT CTGTTCCTGG
3961 ATGGGACAAG AAATTTACTA CTGAGCAGCT TGAGGCTTTC AACCATCAAT TTGAATCATC
4021 TAACTTTACT GCACGTGAAT TGGATCTTGA GTTGCAAAAG GATGTTGCCA GAGTGATTTT
```

Stop Mevalonate Pyrophosphate
```
4081 AACTCAAGTC GGTTCAGGCC CACAAGAAAC AAACGAATCT TTGATTGAGC CAAAGACTGG
```

Decraboxylase ──────▶|
```
4141 TCTACCAAAG GAATAACTGC AGCCCGGGGG ATCCACTAGT TCTAGAGCGG CCGCCACCGC
4201 GGTGGAGCTC CAATTCGCCC TATAGTGAGT CGTATTACGC GCGCTCACTG GCCGTCGTTT
4261 TACAACGTCG TGACTGGGAA AACCCTGGCG TTACCCAACT TAATCGCCTT GCAGCACATC
4321 CCCCTTTCGC CAGCTGGCGT AATAGCGAAG AGGCCCGCAC CGATCGCCCT TCCCAACAGT
4381 TGCGCAGCCT GAATGGCGAA TGGAAATTGT AAGCGTTAAT ATTTTGTTAA AATTCGCGTT
4441 AAATTTTTGT TAAATCAGCT CATTTTTTAA CCAATAGGCC GA
```

SEQ ID NO 10 Isopentyl pyrophosphate isomerase (idi) nucleotide sequence
```
   1 ATGCAAACGG AACACGTCAT TTTATTGAAT GCACAGGGAG TTCCCACGGG TACGCTGGAA
  61 AAGTATGCCG CACACACGGC AGACACCCGC TTACATCTCG CGTTCTCCAG TTGGCTGTTT
 121 AATGCCAAAG GACAATTATT AGTTACCCGC CGCGCACTGA GCAAAAAAGC ATGGCCTGGC
 181 GTGTGGACTA ACTCGGTTTG TGGGCACCCA CAACTGGGAG AAAGCAACGA AGACGCAGTG
 241 ATCCGCCGTT GCCGTTATGA GCTTGGCGTG GAAATTACGC CTCCTGAATC TATCTATCCT
 301 GACTTTCGCT ACCGCGCCAC CGATCCGAGT GGCATTGTGG AAAATGAAGT GTGTCCGGTA
 361 TTTGCCGCAC GCACCACTAG TGCGTTACGA ATCAATGATG ATGAAGTGAT GGATTATCAA
 421 TGGTGTGATT TAGCAGATGT ATTACACGGT ATTGATGCCA CGCCGTGGGC GTTCAGTCCG -
 481 TGGATGGTGA TGCAGGCGAC AAATCGCGAA GCCAGAAAAC GATTATCTGC ATTTACCCAG
 541 CTTAAATAA
```

SEQ ID NO 11 Farnesyl pyrophosphate synthase (ispA) nucleotide sequence
```
   1 ATGGACTTTC CGCAGCAACT CGAAGCCTGC GTTAAGCAGG CCAACCAGGC GCTGAGCCGT
  61 TTTATCGCCC CACTGCCCTT TCAGAACACT CCCGTGGTCG AAACCATGCA GTATGGCGCA
 121 TTATTAGGTG GTAAGCGCCT GCGACCTTTC CTGGTTTATG CCACCGGTCA TATGTTCGGC
 181 GTTAGCACAA ACACGCTGGA CGCACCCGCT GCCGCCGTTG AGTGTATCCA CGCTTACTCA
 241 TTAATTCATG ATGATTTACC GGCAATGGAT GATGACGATC TGCGTCGCGG TTTGCCAACC
 301 TGCCATGTGA AGTTTGGCGA AGCAAACGCG ATTCTCGCTG GCGACGCTTT ACAAACGCTG
 361 GCGTTCTCGA TTTTAAGCGA TGCCGATATG CCGGAAGTGT CGGACCGCGA CAGAATTTCG
 421 ATGATTTCTG AACTGGCGAG CGCCAGTGGT ATTGCCGGAA TGTGCGGTGG TCAGGCATTA
 481 GATTTAGACG CGGAAGGCAA ACACGTACCT CTGGACGCGC TTGAGCGTAT TCATCGTCAT
 541 AAAACCGGCG CATTGATTCG CGCCGCCGTT CGCCTTGGTG CATTAAGCGC CGGAGATAAA
 601 GGACGTCGTG CTCTGCCGGT ACTCGACAAG TATGCAGAGA GCATCGGCCT TGCCTTCCAG
 661 GTTCAGGATG ACATCCTGGA TGTGGTGGGA GATACTGCAA CGTTGGGAAA ACGCCAGGGT
 721 GCCGACCAGC AACTTGGTAA AAGTACCTAC CCTGCACTTC TGGGTCTTGA GCAAGCCCGG
 781 AAGAAAGCCC GGGATCTGAT CGACGATGCC CGTCAGTCGC TGAAACAACT GGCTGAACAG
 841 TCACTCGATA CCTCGGCACT GGAAGCGCTA GCGGACTACA TCATCCAGCG TAATAAATAA
```

SEQ ID NO 12 "MBI" operon nucleotide sequence
      Lac Promoter
```
   1 GCGCAACGCA ATTAATGTGA GTTAGCTCAC TCATTAGGCA CCCCAGGCTT TACACTTTAT
  61 GCTTCCGGCT CGTATGTTGT GTGGAATTGT GAGCGGATAA CAATTTCACA CAGGAAACAG
 121 CTATGACCAT GATTACGCCA AGCGCGCAAT TAACCCTCAC TAAAGGGAAC AAAAGCTGGG

181 TACCGGGCCC CCCCTCGAGG TCGACGGTAT CGATAAGCTT GATATCGAAT TCCTGCAGTA
```

RBS          ┌─ Start Mevalonate Kinase
```
 241 GGAGGAATTA ACCATGTCAT TACCGTTCTT AACTTCTGCA CCGGGAAAGG TTATTATTTT 301 TGGTGAACAC TCTGCTGTGT ACAACAAGCC TGCCGTCGCT GCTAGTGTGT CTGCGTTGAG
 361 AACCTACCTG CTAATAAGCG AGTCATCTGC ACCAGATACT ATTGAATTGG ACTTCCCGGA
 421 CATTAGCTTT AATCATAAGT GGTCCATCAA TGATTTCAAT GCCATCACCG AGGATCAAGT
 481 AAACTCCCAA AAATTGGCCA AGGCTCAACA AGCCACCGAT GGCTTGTCTC AGGAACTCGT
 541 TAGTCTTTTG GATCCGTTGT TAGCTCAACT ATCCGAATCC TTCCACTACC ATGCAGCGTT
 601 TTGTTTCCTG TATATGTTTG TTTGCCTATG CCCCCATGCC AAGAATATTA AGTTTTCTTT
 661 AAAGTCTACT TTACCCATCG GTGCTGGGTT GGGCTCAAGC GCCTCTATTT CTGTATCACT
 721 GGCCTTAGCT ATGGCCTACT TGGGGGGGTT AATAGGATCT AATGACTTGG AAAAGCTGTC
 781 AGAAAACGAT AAGCATATAG TGAATCAATG GGCCTTCATA GGTGAAAAGT GTATTCACGG
 841 TACCCCTTCA GGAATAGATA ACGCTGTGGC CACTTATGGT AATGCCCTGC TATTTGAAAA
```

SEQUENCE LISTING
Assignment of SEQ ID NOS

```
 901 AGACTCACAT AATGGAACAA TAAACACAAA CAATTTTAAG TTCTTAGATG ATTTCCCAGC
 961 CATTCCAATG ATCCTAACCT ATACTAGAAT TCCAAGGTCT ACAAAAGATC TTGTTGCTCG
1021 CGTTCGTGTG TTGGTCACCG AGAAATTTCC TGAAGTTATG AAGCCAATTC TAGATGCCAT
1081 GGGTGAATGT GCCCTACAAG GCTTAGAGAT CATGACTAAG TTAAGTAAAT GTAAAGGCAC
1141 CGATGACGAG GCTGTAGAAA CTAATAATGA ACTGTATGAA CAACTATTGG AATTGATAAG
1201 AATAAATCAT GGACTGCTTG TCTCAATCGG TGTTTCTCAT CCTGGATTAG AACTTATTAA
1261 AAATCTGAGC GATGATTTGA GAATTGGCTC CACAAAACTT ACCGGTGCTG GTGGCGGCGG
1321 TTGCTCTTTG ACTTTGTTAC GAAGAGACAT TACTCAAGAG CAAATTGACA GCTTCAAAAA
1381 GAAATTGCAA GATGATTTTA GTTACGAGAC ATTTGAAACA GACTTGGGTG GGACTGGCTG
1441 CTGTTTGTTA AGCGCAAAAA ATTTGAATAA AGATCTTAAA ATCAAATCCC TAGTATTCCA
1501 ATTATTTGAA AATAAAACTA CCACAAAGCA ACAAATTGAC GATCTATTAT TGCCAGGAAA

Stop Mevalonate Kinase─▶|                |─▶ Start Phosphomevalonate
1561 CACGAATTTA CCATGGACTT CATAGGAGGC AGATCAAATG TCAGAGTTGA GAGCCTTCAG
                                  RBS Kinase
1621 TGCCCCAGGG AAAGCGTTAC TAGCTGGTGG ATATTTAGTT TTAGATACAA AATATGAAGC
1681 ATTTGTAGTC GGATTATCGG CAAGAATGCA TGCTGTAGCC CATCCTTACG GTTCATTGCA
1741 AGGGTCTGAT AAGTTTGAAG TGCGTGTGAA AAGTAAACAA TTTAAAGATG GGGAGTGGCT
1801 GTACCATATA AGTCCTAAAA GTGGCTTCAT TCCTGTTTCG ATAGGCGGAT CTAAGAACCC
1861 TTTCATTGAA AAAGTTATCG CTAACGTATT TAGCTACTTT AAACCTAACA TGGACGACTA
1921 CTGCAATAGA AACTTGTTCG TTATTGATAT TTTCTCTGAT GATGCCTACC ATTCTCAGGA
1981 GGATAGCGTT ACCGAACATC GTGGCAACAG AAGATTGAGT TTTCATTCGC ACAGAATTGA
2041 AGAAGTTCCC AAAACAGGGC TGGGCTCCTC GGCAGGTTTA GTCACAGTTT TAACTACAGC
2101 TTTGGCCTCC TTTTTTGTAT CGGACCTGGA AAATAATGTA GACAAATATA GAGAAGTTAT
2161 TCATAATTTA GCACAAGTTG CTCATTGTCA AGCTCAGGGT AAAATTGGAA GCGGGTTTGA
2221 TGTAGCGGCG GCAGCATATG GATCTATCAG ATATAGAAGA TTCCCACCCG CATTAATCTC
2281 TAATTTGCCA GATATTGGAA GTGCTACTTA CGGCAGTAAA CTGGCGCATT GGTTGATGA
234f AGAAGACTGG AATATTACGA TTAAAAGTAA CCATTTACCT TCGGGATTAA CTTTATGAT
2401 GGGCGATATT AAGAATGGTT CAGAAACAGT AAAACTGGTC CAGAAGGTAA AAATTGGTA
2461 TGATTCGCAT ATGCCAGAAA GCTTGAAAAT ATATACAGAA CTCGATCATG CAAATTCTAG
2521 ATTTATGGAT GGACTATCTA AACTAGATCG CTTACACGAG ACTCATGACG ATTACAGCGA
2581 TCAGATATTT GAGTCTCTTG AGAGGAATGA CTGTACCTGT CAAAAGTATC CTGAAATCAC
2641 AGAAGTTAGA GATGCAGTTG CCACAATTAG ACGTTCCTTT AGAAAAATAA CTAAAGAATC
2701 TGGTGCCGAT ATCGAACCTC CCGTACAAAC TAGCTTATTG GATGATTGCC AGACCTAAA
2761 AGGAGTTCTT ACTTGCTTAA TACCTGGTGC TGGTGGTTAT GACGCCATTG CAGTGATTAC
2821 TAAGCAAGAT GTTGATCTTA GGGCTCAAAC CGCTAATGAC AAAAGATTTT CTAAGGTTCA Stop Phosphomevalonate
2881 ATGGCTGGAT GTAACTCAGG CTGACTGGGG TGTTAGGAAA GAAAAAGATC CGGAAACTTA Kinase──────────▶|           |─▶ Start Mevalonate Pyrophosphate
2941 TCTTGATAAA TAGGAGGTAA TACTCATGAC CGTTTACACA GCATCCGTTA CCGCACCCGT
                      RBS Decarboxylase
3001 CAACATCGCA ACCCTTAAGT ATTGGGGGAA AAGGGACACG AAGTTGAATC TGCCCACCAA
3061 TTCGTCCATA TCAGTGACTT TATCGCAAGA TGACCTCAGA ACGTTGACCT CTGCGGCTAC
3121 TGCACCTGAG TTTGAACGCG ACACTTTGTG GTTAAATGGA GAACCACACA GCATCGACAA
3181 TGAAAGAACT CAAAATTGTC TGCGCGACCT ACGCCAATTA AGAAAGGAAA TGGAATCGAA
3241 GGACGCCTCA TTGCCCACAT TATCTCAATG GAAACTCCAC ATTGTCTCCG AAAATAACTT
3301 TCCTACAGCA GCTGGTTTAG CTTCCTCCGC TGCTGGCTTT GCTGCATTGG TCTCTGCAAT
3361 TGCTAAGTTA TACCAATTAC CACAGTCAAC TTCAGAAATA TCTAGAAAG CAAGAAAGGG
3421 GTCTGGTTCA GCTTGTAGAT CGTTGTTTGG CGGATACGTG GCCTGGGAAA TGGGAAAAGC
3481 TGAAGATGGT CATGATTCCA TGGCAGTACA AATCGCAGAC AGCTCTGACT GGCCTCAGAT
3541 GAAAGCTTGT GTCCTAGTTG TCAGCGATAT TAAAAAGGAT GTGAGTTCCA CTCAGGGTAT
3601 GCAATTGACC GTGGCAACCT CCGAACTATT TAAAGAAAGA ATTGAACATG TCGTACCAAA
3661 GAGATTTGAA GTCATGCGTA AAGCCATTGT TGAAAAAGAT TTCGCCACCT TCGCCAAAGGA
3721 AACAATGATG GATTCCAACT CTTTCCATGC CACATGTTTG GACTCTTTCC CTCCAATATT
3781 CTACATGAAT GACACTTCCA AGCGTATCAT CAGTTGGTGC CACACCATTA ATCAGTTTTA
3841 CGGAGAAACA ATCGTTGCAT ACACGTTTGA TGCAGGTCCA AATGCTGTGT TGTACTACTT
3901 AGCTGAAAAT GAGTCGAAAC TCTTTGCATT TATCTATAAA TTGTTTGGCT CTGTTCCTGG
3961 ATGGGACAAG AAATTTACTA CTGAGCAGCT TGAGGCTTTC AACCATCAAT TTGAATCATC
4021 TAACTTTACT GCACGTGAAT TGGATCTTGA GTTGCAAAAG GATGTTGCCA GAGTGATTTT Stop Mevalonate Pyrophosphate
4081 AACTCAAGTC GGTTCAGGCC CACAAGAAAC AAACGAATCT TTGATTGACG CAAAGACTGG Decarboxylase ─────▶|      RBS       |─▶ Start Isopentyl
4141 TCTACCAAAG GAATAACTGC AGCCCGGGAG GAGGATTACT ATATGCAAAC GGAACACGTC
```

-continued

SEQUENCE LISTING
Assignment of SEQ ID NOS

Pyrophosphate Isomerase
```
4201 ATTTTATTGA ATGCACAGGG AGTTCCCACG GGTACGCTGG AAAAGTATGC CGCACACACG
4261 GCAGACACCC GCTTACATCT CGCGTTCTCC AGTTGGCTGT TTAATGCCAA AGGACAATTA
4321 TTAGTTACCC GCCGCGCACT GAGAAAAAAA GCATGGCCTG GCGTGTGGAC TAACTCGGTT
4381 TGTGGGCACC CACAACTGGG AGAAAGCAAC GAAGACGCAG TGATCCGCCG TTGCCGTTAT
4441 GAGCTTGGCG TGGAAATTAC GCCTCCTGAA TCTATCTATC CTGACTTTCG CTACCGCGCC
4501 ACCGATCCGA GTGGCATTGT GGAAAATGAA GTGTGTCCGG TATTTGCCGC ACGCACCACT
4561 AGTGCGTTAC AGATCAATGA TGATGAAGTG ATGGATTATC AATGGTGTGA TTTAGCAGAT
4621 GTATTACACG GTATTGATGC CACGCCGTGG GCGTTCAGTC CGTGGATGGT GATGCAGGCG
```

Stop Isopentyl Pyrophosphate Decarboxylase ──▶|
```
4681 ACAAATCGCG AAGCCAGAAA ACGATTATCT GCATTTACCC AGCTTAAATA ACCCGGGGGA
4741 TCCACTAGTT CTAGAGCGGC CGCCACCGCG GTGGAGCTCC AATTCGCCCT ATAGTGAGTC
4801 GTATTACGCG CGCTCACTGG CCGTCGTTTT ACAACGTCGT GACTGGGAAA ACCCTGGCGT
4861 TACCCAACTT AATCGCCTTG CAGCACATCC CCCTTTCGCC AGCTGGCGTA ATAGCGAAGA
4921 GGCCCGCACC GATCGCCCTT CCCAACAGTT GCGCAGCCTG AATGGCGAAT GGAAATTGTA
4981 AGCGTTAATA TTTTGTTAAA ATTCGCGTTA AATTTTTGTT AAATCAGCTC ATTTTTTAAC
5041 CAATAGGCCG A
```

SEQ ID NO 13 "MBIS" operon nucleotide sequence
        Lac Promoter
```
   1 GCGCAACGCA ATTAATGTGA GTTAGCTCAC TCATTAGGCA CCCCAGGCTT TACACTTTAT

61 GCTTCCGGCT CGTATGTTGT GTGGAATTGT GAGCGGATAA CAATTTCACA CAGGAAACAG

121 CTATGACCAT GATTACGCCA AGCGCGCAAT TAACCCTCAC TAAAGGGAAC AAAAGCTGGG

181 TACCGGGCCC CCCCTCGAGG TCGACGGTAT CGATAAGCTT GATATCGAAT TCCTGCAGTA
```

RBS          ┌──▶ Start Mevalonate Kinase
```
 241 GGAGGAATTA ACCATGTCAT TACCGTTCTT AACTTCTGCA CCGGGAAAGG TTATTATTTT 301 TGGTGAACAC TCTGCTGTGT ACAACAAGCC TGCCGTCGCT GCTAGTGTGT CTGCGTTGAG
 361 AACCTACCTG CTAATAAGCG AGTCATCTGC ACCAGATACT ATTGAATTGG ACTTCCCGGA
 421 CATTAGCTTT AATCATAAGT GGTCCATCAA TGATTTCAAT GCCATCACCG AGGATCAAGT
 481 AAACTCCCAA AAATTGGCAA AGGCTCAACA AGCCACCGAT GGCTTGTCTC AGGAACTCGT
 541 TAGTCTTTTG GATCCGTTGT TAGCTCAACT ATCCGAATCC TTCCACTACC ATGCAGCGTT
 601 TTGTTTCCTG TATATGTTTG TTTGCCTATG CCCCCATGCC AAGAATATTA AGTTTTCTTT
 661 AAAGTCTACT TTACCCATCG GTGCTGGGTT GGGCTCAAGC GCCTCTATTT CTGTATCACT
 721 GGCCTTAGCT ATGGCCTACT TGGGGGGGTT AATAGGATCT AATGACTTGG AAAAGCTGTC
 781 AGAAAACGAT AAGCATATAG TGAATCAATG GGCCTTCATA GGTGAAAAGT GTATTCACGG
 841 TACCCCTTCA GGAATAGATA CGCTGTGGC CACTTATGGT AATGCCCTGC TATTTGAAAA
 901 AGACTCACAT AATGGAACAA TAAACACAAA CAATTTTAAG TTCTTAGATG ATTTCCCAGC
 961 CATTCCAATG ATCCTAACCT ATACTAGAAT TCCAAGGTCT ACAAAAGATC TTGTTGCTCG
1021 CGTTCGTGTG TTGGTCACCG AGAAATTTCC TGAAGTTATG AAGCCAATTC TAGATGCCAT
1081 GGGTGAATGT GCCCTACAAG GCTTAGAGAT CATGACTAAG TTAAGTAAAT GTAAAGGCAC
1141 CGATGACGAG GCTGTAGAAA CTAATAATGA ACTGTATGAA CAACTATTGG AATTGATAAG
1201 AATAAATCAT GGACTGCTTG TCTCAATCGG TGTTTCTCAT CCTGGATTAG AACTTATTAA
1261 AAATCTGAGC GATGATTTGA GAATTGGCTC CACAAAACTT ACCGGTGCTG GTGGCGGCGG
1321 TTGCTCTTTG ACTTTGTTAC GAAGAGACAT TACTCAAGAG CAAATTGACA GCTTCAAAAA
1381 GAAATTGCAA GATGATTTTA GTTACGAGAC ATTTGAAACA GACTTGGGTG GGACTGGCTG
1441 CTGTTTGTTA AGCGCAAAAA ATTTGAATAA AGATCTTAAA ATCAAATCCC TAGTATTCCA
1501 ATTATTTGAA AATAAAACTA CCACAAAGCA ACAAATTGAC GATCTATTAT TGCCAGGAAA
```

Stop Mevalonate Kinase ──▶|          |──▶ Start Phosphomevalonate
```
1561 CACGAATTTA CCATGGACTT CATAGGAGGC AGATCAAATG TCAGAGTTGA GAGCCTTCAG
                                RBS
```

Kinase
```
1621 TGCCCCAGGG AAAGCGTTAC TAGCTGGTGG ATATTTAGTT TTAGATACAA AATATGAAGC
1681 ATTTGTAGTC GGATTATCGG CAAGAATGCA TGCTGTAGCC CATCCTTACG GTTCATTGCA
1741 AGGGTCTGAT AAGTTTGAAG TGCGTGTGAA AAGTAAACAA TTTAAAGATG GGGAGTGGCT
1801 GTACCATATA AGTCCTAAAA GTGGCTTCAT TCCTGTTTCG ATAGGCGGAT CTAAGAACCC
1861 TTTCATTGAA AAAGTTATCG CTAACGTATT TAGCTACTTT AAACCTAACA TGGACGACTA
1921 CTGCAATAGA AACTTGTTCG TTATTGATAT TTTCTCTGAT GATGCCTACC ATTCTCAGGA 1981 GGATAGCGTT ACCGAACATC GTGGCAACAG AAGATTGAGT TTTCATTCGC ACAGAATTGA
2041 AGAAGTTCCC AAAACAGGGC TGGGCTCCTC GGCAGGTTTA GTCACAGTTT TAACTACAGC
2101 TTTGGCCTCC TTTTTTGTAT CGGACCTGGA AAATAATGTA GACAAATATA GAGAAGTTAT
2161 TCATAATTTA GCACAAGTTG CTCATTGTCA AGCTCAGGGT AAAATTGGAA GCGGGTTTGA
2221 TGTAGCGGCG GCAGCATATG GATCTATCAG ATATAGAAGA TTCCCACCCG CATTAATCTC
2281 TAATTTGCCA GATATTGGAA GTGCTACTTA CGGCAGTAAA CTGGCGCATT GGTTGATGA
2341 AGAAGACTGG AATATTACGA TTAAAAGTAA CCATTTACCT TCGGGATTAA CTTTATGGAT
2401 GGGCGATATT AAGAATGGTT CAGAAACAGT AAAACTGGTC CAGAAGGTAA AAATTGGTA
```

```
2461 TGATTCGCAT ATGCCAGAAA GCTTGAAAAT ATATACAGAA CTCGATCATG CAAATTCTAG
2521 ATTTATGGAT GGACTATCTA AACTAGATCG CTTACACGAG ACTCATGACG ATTACAGCGA
2581 TCAGATATTT GAGTCTCTTG AGAGGAATGA CTGTACCTGT CAAAAGTATC CTGAAATCAC
2641 AGAAGTTAGA GATGCAGTTG CCACAATTAG ACGTTCCTTT AGAAAAATAA CTAAAGAATC
2701 TGGTGCCGAT ATCGAACCTC CCGTACAAAC TAGCTTATTG GATGATTGCC AGACCTTAAA
2761 AGGAGTTCTT ACTTGCTTAA TACCTGGTGC TGGTGGTTAT GACGCCATTG CTAAGGTTCA
2821 TAAGCAAGAT GTTGATCTTA GGGCTCAAAC CGCTAATGAC AAAAGATTTT CTAAGGTTCA
```

Stop Phosphomevalonate
```
2881 ATGGCTGGAT GTAACTCAGG CTGACTGGGG TGTTAGGAAA GAAAAAGATC CGGAAACTTA
```

Kinase ─────▶|　　　　　|──▶ Start Mevalonate Pyrophosphate
```
2941 TCTTGATAAA TAGGAGGTAA TACTCATGAC CGTTTACACA GCATCCGTTA CCGCACCCGT
                 RBS
```

Decarboxylase
```
3001 CAACATCGCA ACCCTTAAGT ATTGGGGGAA AAGGGACACG AAGTTGAATC TGCCCACCAA
3061 TTCGTCCATA TCAGTGACTT TATCGCAAGA TGACCTCAGA ACGTTGACCT CTGCGGCTAC
3121 TGCACCTGAG TTTGAACGCG ACACTTTGTG GTTAAATGGA GAACCACACA GCATCGACAA
3181 TGAAAGAACT CAAAATTGTC TGCGCGACCT ACGCCAATTA AGAAAGGAAA TGGAATCGAA
3241 GGACGCCTCA TTGCCCACAT TATCTCAATG GAAACTCCAC ATTGTCTCCG AAAATAACTT
3301 TCCTACAGCA GCTGGTTTAG CTTCCTCCGC TGCTGGCTTT GCTGCATTGG TCTCTGCAAT
3361 TGCTAAGTTA TACCAATTAC CACAGTCAAC TTCAGAAATA TCTAGAATAG CAAGAAAGGG
3421 GTCTGGTTCA GCTTGTAGAT CGTTGTTTGG CGGATACGTG GCCTGGGAAA TGGGAAAAGC
3481 TGAAGATGGT CATGATTCCA TGGCAGTACA AATCGCAGAC AGCTCTGACT GGCCTCAGAT
3541 GAAAGCTTGT GTCCTAGTTG TCAGCGATAT TAAAAAGGAT GTGAGTTCCA CTCAGGGTAT
3601 GCAATTGACC GTGGCAACCT CCGAACTATT TAAAGAAAGA ATTGAACATG TCGTACCAAA
3661 GAGATTTGAA GTCATGCGTA AAGCCATTGT TGAAAAAGAT TTCGCCACCT TTGCAAAGGA
3721 AACAATGATG GATTCCAACT CTTTCCATGC ACATGTTTTG GACTCTTTCC CTCCAATATT
3781 CTACATGAAT GACACTTCCA AGCGTATCAT CAGTTGGTGC CACACCATTA ATCAGTTTTA
3841 CGGAGAAACA ATCGTTGCAT ACACGTTTGA TGCAGGTCCA AATGCTGTGT TGTACTACTT
3901 AGCTGAAAAT GAGTCGAAAC TCTTTGCATT TATCTATAAA TTGTTTGGCT CTGTTCCTGG
3961 ATGGGACAAG AAATTTACTA CTGAGCAGCT TGAGGCTTTC AACCATCAAT TGAATCATC
4021 TAACTTTACT GCACGTGAAT TGGATCTTGA GTTGCAAAAG GATGTTGCCA GAGTGATTTT
```
　　　　　　　　　　　　　　　　　　　　　　　　　Stop Mevalonate Pyrophosphate
```
4081 AACTCAAGTC GGTTCAGGCC CACAAGAAAC AAACGAATCT TGATTGACG CAAAGACTGG
```

Decarboxylase ────▶|　　　　RBS　　　　|──▶ Start isopentyl
```
4141 TCTACCAAAG GAATAACTGC AGCCCGGGAG GAGGATTACT ATATGCAAAC GGAACACGTC
```

Pyrophosphate Isomerase (idi)
```
4201 ATTTTATTGA ATGCACAGGG AGTTCCCACG GGTACGCTGG AAAAGTATGC CGCACACACG
4261 GCAGACACCC GCTTACATCT CGCGTTCTCC AGTTGGCTGT TTAATGCCAA AGGACAATTA
4321 TTAGTTACCC GCCGCGCACT GAGCAAAAAA GCATGGCCTG GCGTGTGGAC TAACTCGGTT
4381 TGTGGGCACC CACAACTGGG AGAAAGCAAC GAAGACGCAG TGATCCGCCG TTGCCGTTAT
4441 GAGCTTGGCG TGGAAATTAC GCCTCCTGAA TCTATCTATC CTGACTTTCG CTACCGCGCC
4501 ACCGATCCGA GTGGCATTGT GGAAAATGAA GTGTGTCCGG TATTTGCCGC ACGCACCACT
4561 AGTGCGTTAC AGATCAATGA TGATGAAGTG ATGGATTATC AATGGTGTGA TTTAGCAGAT
4621 GTATTACACG GTATTGATGC CACGCCGTGG GCGTTCAGTC CGTGGATGGT GATGCAGGCG
```

Stop: Isopentyl Pyrophosphate Decarboxylase ───▶|
```
4681 ACAAATCGCG AAGCCAGAAA ACGATTATCT GCATTTACCC AGCTTAAATA ACCCGGGGGA
```
　　　　　　　　　　　　　　　　　RBS　　　|──▶ Start Farnesyl
```
4741 TCCACTAGTT CTAGAGCGGC CGCCACCGCG GAGGAGGAAT GAGTAATGGA CTTTCCGCAG
```

Pyrophosphate Synthase (ispA)
```
4801 CAACTCGAAG CCTGCGTTAA GCAGGCCAAC CAGGCGCTGA GCCGTTTTAT CGCCCCACTG
4861 CCCTTTCAGA ACACTCCCGT GGTCGAAACC ATGCAGTATG GCGCATTATT AGGTGGTAAG
4921 CGCCTGCGAC CTTTCCTGGT TTATGCCACC GGTCATATGT TCGGCGTTAG CACAAACACG
4981 CTGGACGCCA CCGCTGCCGC CGTTGAGTGT ATCCACGCTT ACTCATTAAT TCATGATGAT
5041 TTACCGGCAA TGGATGATGA CGATCTGCGT CGCGGTTTGC CAACCTGCCA TGTGAAGTTT
5101 GGCGAAGCAA ACGCGATTCT CGCTGGCGAC GCTTTACAAA CGCTGGCGTT CTCGATTTTA
5161 AGCGATGCCG ATATGCCGGA AGTGTCGGAC CGCGACAGAA TTTCGATGAT TTCTGAACTG
5221 GCGAGCGCCA GTGGTATTGC CGGAATGTGC GGTGGTCAGG CATTAGATTT AGACGCGGAA
5281 GCCAAACACG TCAATCTGGA CGCGCTTGAG CGTATTCATC GTCATAAAAC CGGCGCATTG
5341 ATTCGCGCCG CCGTTCGCCT TGGTGCATTA AGCGCCGGAG ATAAAGGACG TCGTGCTCTG
5401 CCGGTACTCG ACAAGTATGC AGAGAGCATC GGCCTTGCCT TCCAGGTTCA GGATGACATC
5461 CTGGATGTGG TGGGAGATAC TGCAACGTTG GGAAAACGCC AGGGTGCCGA CCAGCAACTT
5521 GGTAAAAGTA CCTACCCTGC ACTTCTGGGT CTTGAGCAAG CCCGGAAGAA AGCCCGGGAT
5581 CTGATCGACG ATGCCCGTCA GTCGCTGAAA CAACTGGCTG AACAGTCACT CGATACCTCG
```

```
                    SEQUENCE LISTING
                 Assignment of SEQ ID NOS Stop  Farnesyl Pyrophosphate Synthase ──▶|
5641 GCACTGGAAG CGCTAGCGGA CTACATCATC CAGCGTAATA AATAAGAGCT CCAATTCGCC
5701 CTATAGTGAG TCGTATTACG CGCGCTCACT GGCCGTCGTT TTACAACGTC GTGACTGGGA
5761 AAACCCTGGC GTTACCCAAC TTAATCGCCT TGCAGCACAT CCCCCTTTCG CCAGCTGGCG
5821 TAATAGCGAA GAGGCCCGCA CCGATCGCCC TTCCCAACAG TTGCGCAGCC TGAATGGCGA
5881 ATGGAAATTG TAAGCGTTAA TATTTTGTTA AAATTCGCGT TAAATTTTTG TTAAATCAGC
5941 TCATTTTTTA ACCAATAGGC CGA
```

What is claimed is:

1. A transformed host cell that synthesizes an isoprenoid or an isoprenoid precursor via a mevalonate pathway,
wherein the transformed host cell is a prokaryote that does not normally synthesize isopentenyl pyrophosphate (IPP) through the mevalonate pathway, wherein the transformed host cell comprises one or more nucleic acids heterologous to the host cell, wherein the one or more heterologous nucleic acids comprises nucleotide sequences that encode mevalonate pathway enzymes comprising:
(a) an enzyme that condenses two molecules of acetyl-CoA to acetoacetyl-CoA as the first step in the synthesis of the isoprenoid or isoprenoid precursor;
(b) an enzyme that condenses acetoacetyl-CoA with acetyl-CoA to form 3 hydroxy 3 methylglutaryl CoA (HMG-CoA);
(c) an enzyme that converts HMG-CoA to mevalonate;
(d) an enzyme that phosphorylates mevalonate to mevalonate 5-phosphate;
(e) an enzyme that converts mevalonate 5-phosphate to mevalonate 5-pyrophosphate; and
(f) an enzyme that converts mevalonate 5-pyrophosphate to isopentenyl pyrophosphate,
wherein culturing of said transformed host cell in a suitable medium provides for synthesis of the isoprenoid or isoprenoid precursor in a recoverable amount of at least about 5 mg/L.

2. The transformed host cell of claim 1, wherein the one or more heterologous nucleic acids is integrated into the chromosome of the host cell.

3. The transformed host cell of claim 1, wherein the one or more heterologous nucleic acids is contained in at least one extrachromosomal expression vector.

4. The transformed host cell of claim 1, wherein the one or more heterologous nucleic acids is present in a single expression vector.

5. The transformed host cell of claim 1, wherein said nucleotide sequences are present in two or more operons.

6. The transformed host cell of claim 1, wherein the transformed host cell overproduces the isoprenoid or isoprenoid precursor by at least about 5 fold as compared to a control host cell that is not transformed with the one or more heterologous nucleic acids.

7. The transformed host cell of claim 1, wherein the transformed host cell further comprises a heterologous nucleic acid comprising a nucleotide sequence coding isopentenyl pyrophosphate isomerase.

8. The transformed host cell of claim 7, wherein the isoprenoid precursor is IPP, and wherein the IPP is further modified enzymatically by the action of the isopentenyl pyrophosphate isomerase to generate dimethylallyl pyrophosphate (DMAPP).

9. The transformed host cell of claim 8, wherein the transformed host cell further comprises a heterologous nucleic acid comprising a nucleotide sequence encoding one or more polyprenyl pyrophosphate synthases.

10. The transformed host cell of claim 9, wherein the DMAPP is further modified enzymatically with the one or more polyprenyl pyrophosphate synthases to provide an isoprenoid.

11. The transformed host cell of claim 10, wherein the isoprenoid is a monoterpene, a sesquiterpene, a diterpene, a triterpene, a tetraterpene, or a steroid.

12. The transformed host cell of claim 1, wherein the transformed host cell is of a genus selected from Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus.

13. The transformed host cell of claim 1, wherein said transformed host cell also synthesizes IPP via a deoxyxylulose-5 phosphate (DXP) pathway.

14. The transformed host cell of claim 1, wherein said transformed host cell comprises an inactivated deoxyxylulose-5 phosphate (DXP) pathway.

15. A transformed Escherichia coli host cell that synthesizes an isoprenoid or an isoprenoid precursor via a mevalonate pathway,
   wherein the transformed host cell is a prokaryote that does not normally synthesize isopentenyl pyrophosphate (IPP) through the mevalonate pathway, wherein the transformed host cell comprises one or more nucleic acids heterologous to the host cell, wherein the one or more heterologous nucleic acids comprises nucleotide sequences that encode mevalonate pathway enzymes comprising:
   (a) an enzyme that condenses two molecules of acetyl-CoA to acetoacetyl-CoA as the first step in the synthesis of the isoprenoid or isoprenoid precursor;
   (b) an enzyme that condenses acetoacetyl-CoA with acetyl-CoA to form 3 hydroxy 3 methylglutaryl CoA (HMG-CoA);
   (c) an enzyme that converts HMG-CoA to mevalonate;
   (d) an enzyme that phosphorylates mevalonate to mevalonate 5-phosphate;
   (e) an enzyme that converts mevalonate 5-phosphate to mevalonate 5-pyrophosphate; and
   (f) an enzyme that converts mevalonate 5-pyrophosphate to isopentenyl pyrophosphate,
   wherein culturing of said transformed host cell in a suitable medium provides for synthesis of the isoprenoid or isoprenoid precursor in a recoverable amount of at least about 5 mg/L.

16. The transformed host cell of claim 15, wherein said transformed host cell comprises an inactivated deoxyxylulose-5 phosphate (DXP) pathway.

17. The transformed host cell of claim 15, wherein the transformed host cell further comprises a heterologous nucleic acid comprising a nucleotide sequence coding isopentenyl pyrophosphate isomerase.

18. The transformed host cell of claim 17, wherein the isoprenoid precursor is IPP, and wherein the IPP is further modified enzymatically by the action of the isopentenyl pyrophosphate isomerase to generate dimethylallyl pyrophosphate (DMAPP).

19. The transformed host cell of claim 18, wherein the transformed host cell further comprises a heterologous nucleic acid comprising a nucleotide sequence encoding one or more polyprenyl pyrophosphate synthases.

20. The transformed host cell of claim 19, wherein the DMAPP is further modified enzymatically with the one or more polyprenyl pyrophosphate synthases to provide an isoprenoid.

21. The transformed host cell of claim 15, wherein the isoprenoid is a monoterpene.

22. The transformed host cell of claim 21, wherein the monoterpene is selected from limonene, citranellol, and geraniol.

23. The transformed host cell of claim 15, wherein the isoprenoid is a sesquiterpene.

24. The transformed host cell of claim 23, wherein the sesquiterpene is selected from periplanone B, artemisinin, ginkgolide B, forskolin, and farnesol.

25. The transformed host cell of claim 15, wherein the isoprenoid is a diterpene.

26. The transformed host cell of claim 15, wherein the diterpene is selected from casbene and paclitaxel.

27. The transformed host cell of claim 15, wherein the isoprenoid is a triterpene.

28. The transformed host cell of claim 15, wherein the isoprenoid is a tetraterpene.

29. The transformed host cell of claim 15, wherein the isoprenoid is a steroid.

30. The transformed host cell of claim 15, wherein the isoprenoid is lycopene.

31. The transformed host cell of claim 15, wherein the isoprenoid is casbene.

32. The transformed host cell of claim 15, wherein the isoprenoid is amorphadiene.

* * * * *